US007585985B2

(12) United States Patent
Norman et al.

(10) Patent No.: US 7,585,985 B2
(45) Date of Patent: Sep. 8, 2009

(54) SUBSTITUTED BENZOPYRANS AS SELECTIVE ESTROGEN RECEPTOR-BETA AGONISTS

(75) Inventors: Bryan Hurst Norman, Indianapolis, IN (US); Lance Allen Pfeifer, Indianapolis, IN (US); Timothy Ivo Richardson, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/184,507

(22) Filed: Aug. 1, 2008

(65) Prior Publication Data

US 2008/0312312 A1    Dec. 18, 2008

Related U.S. Application Data

(62) Division of application No. 10/552,504, filed as application No. PCT/US2004/009272 on Apr. 8, 2004, now Pat. No. 7,442,812.

(60) Provisional application No. 60/464,404, filed on Apr. 21, 2003.

(51) Int. Cl.
*C07D 311/78* (2006.01)
*A61K 31/35* (2006.01)

(52) U.S. Cl. ...................... 549/385; 514/455

(58) Field of Classification Search .............. 549/390, 549/391, 385; 514/454, 455
See application file for complete search history.

(56) References Cited

U.S. PATENT DOCUMENTS

| | | | |
|---|---|---|---|
| 6,436,923 B1 | 8/2002 | Bhagwat et al. |
| 6,518,301 B1 | 2/2003 | Barlaam et al. |
| 6,593,322 B1 | 7/2003 | Bhagwat et al. |
| 6,630,508 B1 | 10/2003 | Dodge et al. |
| 6,794,403 B2 | 9/2004 | Malamas et al. |
| 7,217,734 B2 | 5/2007 | Dodge et al. |
| 7,279,499 B2 | 10/2007 | Durst et al. |
| 7,354,951 B2 | 4/2008 | Norman et al. |

FOREIGN PATENT DOCUMENTS

| | | |
|---|---|---|
| GB | 2 361 642 | 10/2001 |
| WO | WO 97/09348 | 3/1997 |
| WO | WO 99/02512 | 1/1999 |
| WO | WO 01/49673 | 7/2001 |
| WO | WO 01/64665 | 9/2001 |
| WO | WO 01/72713 | 10/2001 |
| WO | WO 03/044006 | 5/2003 |
| WO | WO 03/051805 | 6/2003 |
| WO | WO 2006/088716 | 8/2006 |

OTHER PUBLICATIONS

Anderson, et al., "Synthesis of 6,9-bisnormethyl-8-methoxy-12,13-epoxy-6,8,10-trichothec atriene," Journal of Organic Chemistry, American Chemical Society, Easton, U.S., vol. 42, No. 6, pp. 1045-1050 (1977).
Oude-Alink, et al., "Photolysis of 2-keto-2,3-dihydrobenzofurans, o-hydroxystyrenes and 1-o-hydroxyphenyl)-1,5-hexadienes," Journal of Organic Chemistry, American Chemical Society, Easton, U.S., vol. 38, No. 11, pp. 1993-2001 (1973).
Shrestha, et al., "Facile synthesis of the fused 6-6-5 ring system containing chroman ring from 2-(1-hydroxy-5-alkenyl)phenol derivatives via intramolecular inverse-electron-demanddiels-alder reaction," Bulletin of the Chemical Society of Japan, Japan Publications Trading Co., Tokyl, JP, vol. 72, No. 1, pp. 73-83 (1999).
Welhua, et al., "A role for estrogen receptor β in the regulation of growth of the ventral prostate," PNAS, vol. 98, No. 11, pp. 6330-6335 (2001).
Mortensen, et al., "Synthesis and biological evaluation of a novel series of furans: ligands selectic for estrogen receptor α," Journal of Medicinal Chemistry, A-K, p. Est. 10:8 (2001).
Meyers, "Estrogen receptor-β potency-selective ligands: structure-activity relationship studies of diarylpropionitriles and their acetylene and polar analogues," Journal of Medicinal Chemistry, A-V, p. Est. 21:3 (2001).
Kuiper, et al., "Cloning of a novel estrogen receptor expressed in rat prostate and ovary," Proc. Natl. Acad. Sci USA, vol. 93, pp. 5925-5930 (1996).
Tremblay, et al., "Cloning, Chromosomal Localization, and Functional Analysis of the Murine Estrogen Receptor β," Molecular Endocrinology, vol. 11, No. 3, pp. 353-365.
Weihua, et al., "Estrogen receptor beta in the prostate," Molecular and Cellular Endocrinology, vol. 193, pp. 1-5 (2002).
Korach, "Insights from the study of animals lacking functional estrogen receptor," Science, vol. 266, pp. 1524-1527 (1994).
Krege, et al., "Generation and reproductive phenotypes of mice lacking estrogen receptor β," Proc. Natl. Acad. Sci. USA, vol. 95, pp. 15677-15682 (1998).
Couse, et al., "Tissue distribution and quantitative analysis of estrogen receptor-α (ERα) and estrogen receptor-β (ERβ) messenger ribonucleic acid in the wild-type and ERa-knockout mouse," Endocrinology, vol. 138, No. 11, pp. 4613-4621 (1997).
Meyers, et al., "Estrogen Receptor-β Potency-Selective Ligands: Structure-Activity Relationship Studies of Diarylpropionitriles and Their Acetylene and Polar Analogues," J. Med. Chem., vol. 44, pp. 4230-4251 (2001.

*Primary Examiner*—Rita J Desai
*Assistant Examiner*—John Mabry
(74) *Attorney, Agent, or Firm*—John C. Demeter; John A. Cleveland, Jr.

(57) ABSTRACT

The present invention relates to substituted benzopyran derivatives, stereoisomers, and pharmaceutical acceptable salts thereof useful as Estrogen Receptor beta agonists for treating Estrogen Receptor beta mediated diseases such as benign prostatic hyperplasia.

6 Claims, No Drawings

SUBSTITUTED BENZOPYRANS AS SELECTIVE ESTROGEN RECEPTOR-BETA AGONISTS

This application is a division under 35 U.S.C. Section 121 of U.S. application Ser. No. 10/552,504, filed Oct. 6, 2005 now U.S. Pat. No. 7,442,812 which is a national phase application under 35 U.S.C. Section 371 of PCT/US2004/009272, filed Apr. 8, 2004, which claims the benefit under 35 U.S.C. Section 119(e) of U.S. provisional patent application 60/464,404, filed Apr. 21, 2003.

BACKGROUND OF THE INVENTION

The present invention relates to novel cycloalkyl-benzopyrans and derivatives thereof, compositions containing those compounds, their use as selective estrogen receptor-beta agonists, and their use in the treatment of estrogen receptor-beta mediated diseases such as prostate cancer, benign prostatic hyperplasia (hypertrophy), testicular cancer, ovarian cancer, lung cancer, cardiovascular diseases, neurodegenerative disorders, urinary incontinence, central nervous system (CNS) disorders, gastrointestinal (GI) tract disorders, and osteoporosis.

Estrogens play important roles in the development and homeostasis of the reproductive, central nervous, skeletal, and cardiovascular systems of both males and females. Recently, a new ER isoform, ER-beta (also known as ER-beta1) was cloned from a rat prostatic cDNA library and is present in murine and human prostates. Consequently, the previous ER is now designated as ER-alpha. ER-alpha and ER-beta share high amino acid homology, have similar 17-β Estradiol (E2) binding affinities, and can hetero- or homodimerize to form a signaling complex; Kuiper G G, et al., Endocrinol. 138: 863-70 (1997); Kuiper G G et al., Proc. Natl. Acad. Sci. USA 93: 5925-30 (1996). Although E2 activates both ER-alpha and ER-beta, ER-alpha stimulates transcription and cellular proliferation, while ER-beta suppresses ER-alpha activation. Interestingly, 3-beta, 17-beta-androstanediol and 5-alpha-androstane have been proposed to be endogenous ligands for ER-beta; Weihua Z. et al. PNAS 98: 6330-5 (2001). 3-Beta, 17-beta-androstanediol is a major metabolite of dihydrotestosterone (DHT), the 5-alpha-reduced active intracellular androgen in male accessory sex organs. ER-beta activation also stimulates increased glutathione S-transferase and quinone reductase expression. These two enzymes have been shown to possess chemoprotective detoxification properties; Chang W Y et al., Prostate 40: 115-24 (1999); Montano M M et al., J. Biol. Chem. 273: 25443-9 (1998).

With the recent identification of ER-beta, and the recognition that ER-alpha and ER-beta have different biological roles, ER-selective modulators would similarly possess significant clinical utility. Since ER-beta is strongly expressed in a number of tissues including prostate, bladder, ovary, testis, lung, small intestine, vascular endothelium, and various parts of the brain, compounds that selectively modulate ER-beta would be of clinical importance in the treatment of a variety of disease conditions, such as prostate cancer, testicular cancer, ovarian cancer, lung cancer, cardiovascular diseases, neurodegenerative disorders, urinary incontinence, CNS disorders, GI tract disorders, and osteoporosis. Such compounds would have minimal effect on tissues that contain ER-alpha, and thus exhibit different side-effect profiles. Thus, ER-beta agonists will display different therapeutic profiles compared to ER-alpha antagonists or agonists, and would be preferentially beneficial in tissues relying on ER-beta signaling.

The prostate gland produces components that are found in the semen and blood. Some of these are regulatory peptides. The prostate gland comprises stroma and epithelium cells, the latter group consisting of columnar secretory cells and basal non-secretory cells. The proliferation of these basal cells, as well as stroma cells gives rise to benign prostatic hyperplasia (BPH), which is one common prostate disease. BPH is a progressive condition that is characterized by the nodular enlargement of the prostatic tissue resulting in obstruction of the urethra. This results in increased frequency of urination, noncuria, poor urine stream, and hesitation or delay in starting the urine flow. Consequences of BPH can include hypertrophy of bladder smooth muscle, decompensated bladder, and increased incidence of urinary tract infection. The development of BPH is considered to be an inescapable phenomenon for the aging male population. BPH is observed in approximately 70% of males over the age of 70. Drug treatment for BPH currently employs alpha andrenergic antagonists for symptomatic relief or steroid 5-alpha reductase inhibitors to reduce hyperplastic tissue bulk. These approaches are of limited therapeutic benefit.

BRIEF SUMMARY OF THE INVENTION

The present invention relates to novel benzopyran derivatives of formula (I):

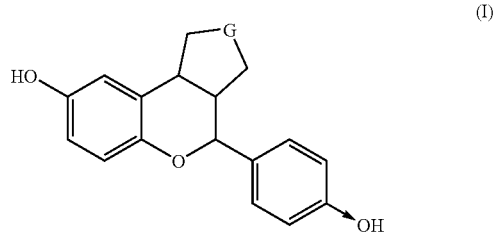

wherein
G is $CHC_1$-$C_6$ alkyl, C=O, CHOH, $CF_2$, $C(OH)CF_3$, $CHCF_3$, $CH(OH)C_1$-$C_6$alkyl, CH—$OC_1$-$C_6$alkyl, CH—$O(CO)C_1$-$C_6$alkyl, CHF, CHCN, $CHC_2$-$C_4$alkenyl, $CHC_2$-$C_4$alkynyl, CHbenzyl, difluoromethylene, O, S(O)n, wherein n is 0-2;

including their enantiomers.

Another embodiment of the invention is a compound of formula II:

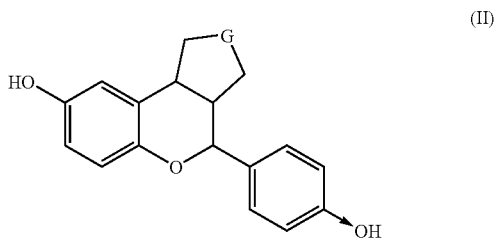

wherein
wherein G is $CHC_1$-$C_6$ alkyl, C=O, CHOH, $CF_2$, $C(OH)CF_3$, $CHCF_3$, $CH(OH)C_1$-$C_6$alkyl, CH—$OC_1$-$C_6$alkyl, CH—$O(CO)C_1$-$C_6$alkyl, CHF, O, S(O)n, wherein n is 0-2;

including the enantiomers;

and the pharmaceutically acceptable salts thereof.

Compounds of the invention include the following, which should not be construed as in any way limiting the compounds included in the invention:

a) (2S,3aS,4R,9bR)-4-(4-Hydroxy-phenyl)-2-methyl-1,2,3,3a,4,9b-hexahydro-cyclopenta[c]chromen-8-ol;
b) (2R,3aR,4S,9bS)-4-(4-Hydroxy-phenyl)-2-methyl-1,2,3,3a,4,9b-hexahydro-cyclopenta[c]chromen-8-ol;
c) (2R,3aR,4S,9bS)-2-tert-Butyl-4-(4-hydroxy-phenyl)-1,2,3,3a,4,9b-hexahydro-cyclopenta[c]chromen-8-ol;
d) (2S,3aS,4R,9bR)-2-tert-Butyl-4-(4-hydroxy-phenyl)-1,2,3,3a,4,9b-hexahydro-cyclopenta[c]chromen-8-ol;
e) (3aS,4S,9bS)-4-(4-Hydroxy-phenyl)-1,3a,4,9b-tetrahydro-3H-2,5-dioxa-cyclopenta[a]naphthalen-8-ol;
f) (3aR,4R,9bR)-4-(4-Hydroxy-phenyl)-1,3a,4,9b-tetrahydro-3H-2,5-dioxa-cyclopenta[a]naphthalen-8-ol;
g) (3aR,4S,9bS)-4-(4-Hydroxy-phenyl)-1,3a,4,9b-tetrahydro-3H-5-oxa-2-thia-cyclopenta[a]naphthalen-8-ol;
h) (3aS,4R,9bR)-4-(4-Hydroxy-phenyl)-1,3a,4,9b-tetrahydro-3H-5-oxa-2-thia-cyclopenta[a]naphthalen-8-ol;
i) (2S,3aR,4S,9bS)-4-(4-Hydroxy-phenyl)-2-oxo-1,2,3,3a,4,9b-hexahydro-5-oxa-2$\lambda^4$-thia-cyclopenta[a]naphthalen-8-ol;
j) (2R,3aS,4R,9bR)-4-(4-Hydroxy-phenyl)-2-oxo-1,2,3,3a,4,9b-hexahydro-5-oxa-2$\lambda^4$-thia-cyclopenta[a]naphthalen-8-ol;
k) (3aR,4S,9bS)-4-(4-Hydroxy-phenyl)-2,2-dioxo-1,2,3,3a,4,9b-hexahydro-5-oxa-2$\lambda^6$-thia-cyclopenta[a]naphthalen-8-ol;
l) (3aS,4R,9bR)-4-(4-Hydroxy-phenyl)-2,2-dioxo-1,2,3,3a,4,9b-hexahydro-5-oxa-2$\lambda^6$-thia-cyclopenta[a]naphthalen-8-ol;
m) (3aR,4S,9bS)-8-Hydroxy-4-(4-hydroxy-phenyl)-1,3a,4,9b-tetrahydro-3H-cyclopenta[c]chromen-2-one;
n) (3aS,4R,9bR)-8-Hydroxy-4-(4-hydroxy-phenyl)-1,3a,4,9b-tetrahydro-3H-cyclopenta[c]chromen-2-one;
o) (2S,3aR,4S,9bS)-4-(4-Hydroxy-phenyl)-1,2,3,3a,4,9b-hexahydro-cyclopenta[c]chromene-2,8-diol;
p) (2R,3aS,4R,9bR)-4-(4-Hydroxy-phenyl)-1,2,3,3a,4,9b-hexahydro-cyclopenta[c]chromene-2,8-diol;
q) (3aR,4S,9bS)-2,2-Difluoro-4-(4-hydroxy-phenyl)-1,2,3,3a,4,9b-hexahydro-cyclopenta[c]chromen-8-ol;
r) (3aS,4R,9bR)-2,2-Difluoro-4-(4-hydroxy-phenyl)-1,2,3,3a,4,9b-hexahydro-cyclopenta[c]chromen-8-ol;
s) (2S,3aR,4S,9bS)-4-(4-Hydroxy-phenyl)-2-trifluoromethyl-1,2,3,3a,4,9b-hexahydro-cyclopenta[c]chromen-8-ol;
t) (2R,3aS,4R,9bR)-4-(4-Hydroxy-phenyl)-2-trifluoromethyl-1,2,3,3a,4,9b-hexahydro-cyclopenta[c]chromen-8-ol;
u) (2R,3aS,4S,9bS)-4-(4-Hydroxy-phenyl)-2-trifluoromethyl-1,2,3,3a,4,9b-hexahydro-cyclopenta[c]chromen-8-ol;
v) (2S,3aS,4R,9bR)-4-(4-Hydroxy-phenyl)-2-trifluoromethyl-1,2,3,3a,4,9b-hexahydro-cyclopenta[c]chromen-8-ol;
w) (2R,3aR,4S,9bS)-2-Ethyl-4-(4-hydroxy-phenyl)-1,2,3,3a,4,9bR-hexahydro-cyclopenta[c]chromene-2,8-diol;
x) (2S,3aS,4R,9bR)-2-Ethyl-4-(4-hydroxy-phenyl)-1,2,3,3a,4,9bR-hexahydro-cyclopenta[c]chromene-2,8-diol;
y) (2S,3aS,4R,9bR)-2-Ethyl-4-(4-hydroxy-phenyl)-1,2,3,3a,4,9b-hexahydro-cyclopenta[c]chromen-8-ol;
z) (2S,3aR,4S,9bS)-2-Ethyl-4-(4-hydroxy-phenyl)-1,2,3,3a,4,9b-hexahydro-cyclopenta[c]chromen-8-ol;
aa) (2S,3aR,4S,9bS)-2-Ethyl-4-(4-hydroxy-phenyl)-1,2,3,3a,4,9b-hexahydro-cyclopenta[c]chromen-8-ol;
bb) (2R,3aR,4S,9bS)-2-Ethyl-4-(4-hydroxy-phenyl)-1,2,3,3a,4,9b-hexahydro-cyclopenta[c]chromen-8-ol;
cc) (2S,3aS,4R,9bR)-4-(4-Hydroxy-phenyl)-2-methoxy-1,2,3,3a,4,9b-hexahydro-cyclopenta[c]chromen-8-ol;
dd) (2R,3aR,4S,9bS)-4-(4-Hydroxy-phenyl)-2-methoxy-1,2,3,3a,4,9b-hexahydro-cyclopenta[c]chromen-8-ol;
ee) (2S,3aS,4R,9bR)-Acetic acid 8-hydroxy-4-(4-hydroxy-phenyl)-1,2,3,3a,4,9b-hexahydro-cyclopenta[c]chromen-2-yl ester;
ff) (2R,3aR,4S,9bS)-Acetic acid 8-hydroxy-4-(4-hydroxy-phenyl)-1,2,3,3a,4,9b-hexahydro-cyclopenta[c]chromen-2-yl ester;
gg) (2R,3aS,4R,9bR)-2-Fluoro-4-(4-hydroxy-phenyl)-1,2,3,3a,4,9b-hexahydro-cyclopenta[c]chromen-8-ol;
hh) (2S,3aR,4S,9bS)-2-Fluoro-4-(4-hydroxy-phenyl)-1,2,3,3a,4,9b-hexahydro-cyclopenta[c]chromen-8-ol;
ii) (2S,3aS,4R,9bR)-2-Fluoro-4-(4-hydroxy-phenyl)-1,2,3,3a,4,9b-hexahydro-cyclopenta[c]chromen-8-ol;
jj) (2R,3aR,4S,9bS)-2-Fluoro-4-(4-hydroxy-phenyl)-1,2,3,3a,4,9b-hexahydro-cyclopenta[c]chromen-8-ol;
kk) (2R,3aR,4S,9bS)- and (2S,3aS,4R,9bR)-8-Hydroxy-4-(4-hydroxy-phenyl)-1,2,3,3a,4,9b-hexahydro-cyclopenta[c]chromene-2-carbonitrile;
ll) (2S,3aR,4S,9bS)- and (2R,3aS,4R,9bR)-8-Hydroxy-4-(4-hydroxy-phenyl)-1,2,3,3a,4,9b-hexahydro-cyclopenta[c]chromene-2-carbonitrile;
mm) (3aR,4S,9bS)- and (3aS,4R,9bR)-4-(4-Hydroxy-phenyl)-2-methylene-1,2,3,3a,4,9b-hexahydro-cyclopenta[c]chromen-8-ol;
nn) (3aR,4S,9bS)- and (3aS,4R,9bR)-2-Difluoromethylene-4-(4-hydroxy-phenyl)-1,2,3,3a,4,9b-hexahydro-cyclopenta[c]chromen-8-ol;
oo) (3aR,4S,9bS)- and (3aS,4R,9bR)-2-Ethynyl-4-(4-hydroxy-phenyl)-1,2,3,3a,4,9b-hexahydro-cyclopenta[c]chromen-8-ol;
pp) 2-Butyl-4-(4-hydroxy-phenyl)-1,2,3,3a,4,9b-hexahydro-cyclopenta[c]chromen-8-ol;
qq) 4-(4-Hydroxy-phenyl)-2-propyl-1,2,3,3a,4,9b-hexahydro-cyclopenta[c]chromen-8-ol;
rr) 2-Ethyl-4-(4-hydroxy-phenyl)-1,2,3,3a,4,9b-hexahydro-cyclopenta[c]chromen-8-ol;
ss) 2-Benzyl-4-(4-hydroxy-phenyl)-1,2,3,3a,4,9b-hexahydro-cyclopenta[c]chromen-8-ol;

including the enantiomers thereof.

The present invention also relates to novel benzopyran derivatives of formula (II):

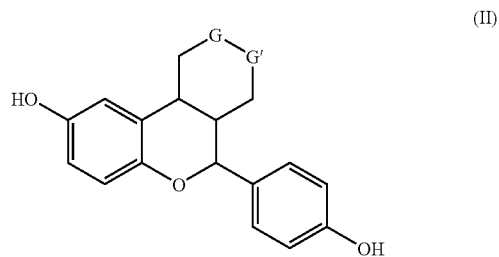

wherein:

G and G' are $CH_2$, C=O, C=$CH_2$, CH$C_1$-$C_6$alkyl or $CF_2$, with the proviso that when G' is other than $CH_2$, G must be $CH_2$ and that when G is other than $CH_2$, G' must be $CH_2$;

including the enantiomers thereof, and the pharmaceutically acceptable salts thereof.

Compounds of the invention include the following, which should not be construed as in any way limiting the compounds included in the invention:
a) (6S,6aR,10aS)-2-Hydroxy-6-(4-hydroxy-phenyl)-6,6a,7,8,10,10a-hexahydro-benzo[c]chromen-9-one;
b) (6aR,6S,10aS)-6-(4-Hydroxy-phenyl)-9-methylene-6a,7,8,9,10,10a-hexahydro-6H-benzo[c]chromen-2-ol;
c) (6aR,6S,9S,10aS)-6-(4-Hydroxy-phenyl)-9-methyl-6a,7,8,9,10,10a-hexahydro-6H-benzo[c]chromen-2-ol;
d) (6aR,6S,9R,10aS)-6-(4-Hydroxy-phenyl)-9-methyl-6a,7,8,9,10,10a-hexahydro-6H-benzo[c]chromen-2-ol;
e) (6aR,6S,10aS)-9,9-Difluoro-6-(4-hydroxy-phenyl)-6a,7,8,9,10,10a-hexahydro-6H-benzo[c]chromen-2-ol;
f) (6aR,6S,10aS)-2-Hydroxy-6-(4-hydroxy-phenyl)-6a,9,10,10a-tetrahydro-6H,7H-benzo[c]chromen-8-one;

including the enantiomers and the pharmaceutically acceptable salts thereof.

In a second embodiment, the present invention provides a pharmaceutical composition comprising a therapeutically effective amount of a compound of formula (I) and a pharmaceutically acceptable carrier.

In a further embodiment, the present invention provides medical methods of employing compounds formula (I) as agonists of estrogen receptor ("ER") beta, further utilized for the treatment of ER beta-mediated diseases such as prostate cancer, benign prostatic hyperplasia, testicular cancer, cardiovascular diseases, neurodegenerative disorders, urinary incontinence, central nervous system (CNS) disorders, gastrointestinal (GI) tract disorders, and osteoporosis.

DETAILED DESCRIPTION OF THE INVENTION

As used in this application:
a) the term "$C_1$-$C_6$ alkyl" refers to a branched or straight chained alkyl radical containing from 1 to 6 carbon atoms, such as methyl (Me), ethyl (Et), n-propyl, isopropyl, n-butyl, isobutyl, sec butyl (s-Bu), tert-butyl (t-Bu), pentyl, hexyl, etc.;
b) the term "$C_2$-$C_4$ alkenyl" refers to a straight or branched hydrocarbon chain of 2 to 4 carbon atoms with at least one carbon-carbon double bond. Examples of $C_2$-$C_4$ alkenyl groups include, but are not limited to, ethenyl(vinyl), propen-1-yl, propen-2-yl(isoprenyl), propen-3-yl(allyl), 2-methyl-propen-3-yl, 2-buten-4-yl, 2-methyl-propen-1-yl, and 1-buten-1-yl;
c) the term "$C_2$-$C_4$ alkynyl" refers to a straight or branched\ hydrocarbon chain of 2 to 4 carbon atoms with at least one carbon-carbon triple bond. Examples of $C_2$-$C_4$ alkynyl groups include, but are not limited to, ethynyl, propyn-1-yl, propyn-2-yl(isoprynyl), propyn-3-yl, 2-methyl-propyn-3-yl, 2-butyn-4-yl, 2-methyl-propyn-1-yl, and 1-butyn-1-yl;
d) the term "halide" refers to a fluorine atom, chlorine atom, bromine atom, or iodine atom;
e) the designation " ∼∼ "refers to a bond for which the stereochemistry is not designated;
f) the designation " ▬ "refers to a bond that protrudes forward out of the plane of the page;
g) the designation " ⋯⋯ "refers to a bond that protrudes backward out of the plane of the page;
h) as used in the preparations and examples the following terms have the indicated meanings; "ng" refers to nanograms; "µg" refers to micrograms; "mg" refers to milligrams; "g" refers to grams; "kg" refers to kilograms; "nmole" refers to nanomoles; "mmol" refers to millimoles; "mol" refers to moles; "µL" refers to microliters; "mL" refers to milliliters; "L" refers to liters; "$R_f$" refers to retention factor; "° C." refers to degrees Celsius; "bp" refers to boiling point; "mm of Hg" refers to pressure in millimeters of mercury; "mp" refers to melting point; "dec" refers to decomposition; "$[\alpha]^{20}_D$" refer to specific rotation of the D line of sodium at 20° C. obtained in a 1 decimeter cell; "c" refers to concentration in g/mL; "nM" refers to nanomolar; "µM" refers to micromolar; "mM" refers to millimolar; "M" refers to molar; "$K_i$" refers to inhibition constant; "$K_d$" refers to dissociation constant; "psi" refers to pounds per square inch; "rpm" refers to revolutions per minute; "HPLC" refers to high performance liquid chromatography; "HRMS" refers to high resolution mass spectrum; "THF" refers to tetrahydrofuran; "brine" refers to a saturated aqueous solution of sodium chloride; "L.O.D." refers to loss on drying; "µCi" refers to microcuries; "i.p." refers to intraperitoneally; "i.v." refers to intravenously; and "DPM" refers to disintegrations per minute;
i) the term "enantiomeric excess" or "ee" refers to the percent by which one enantiomer, E1, is in excess in a mixture of the two enantiomers, E1 plus E2, such that {(E1−E2)÷(E1+E2)}×100=ee;

The compounds used in the method of the present invention may have one or more asymmetric centers. As a consequence of these chiral centers, the compounds of the present invention occur as racemates and as individual enantiomers, as well as diastereomers and mixtures of diastereomers. All asymmetric forms, individual isomers and combinations thereof, are within the scope of the present invention.

In order to preferentially prepare one optical isomer over its enantiomer, a number of routes are available. As an example, a mixture of enantiomers may be prepared, and then the two enantiomers may be separated. A commonly employed method for the separation of a racemic mixture is the use of chiral high pressure liquid chromatography. Further details regarding resolution of enantiomeric mixtures may be found in J. Jacques, et al., Enantiomers, Racemates, and Resolutions, (1991).

The term "pharmaceutically acceptable salts thereof" refers to either an acid addition salt or a basic addition salt.

The expression "pharmaceutically acceptable acid addition salts" is intended to apply to any non-toxic organic or inorganic acid addition salt of the base compounds represented by formula (I). Illustrative inorganic acids that form suitable salts include hydrochloric, hydrobromic, sulphuric, and phosphoric acid and acid metal salts such as sodium monohydrogen orthophosphate, and potassium hydrogen sulfate. Illustrative organic acids that form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as benzenesulfonic acid, methanesulfonic acid, and 2-hydroxyethanesulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (I). Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

Illustrative examples of the compounds encompassed by the present invention include the racemic mixtures and specific enantiomers of the following compounds:

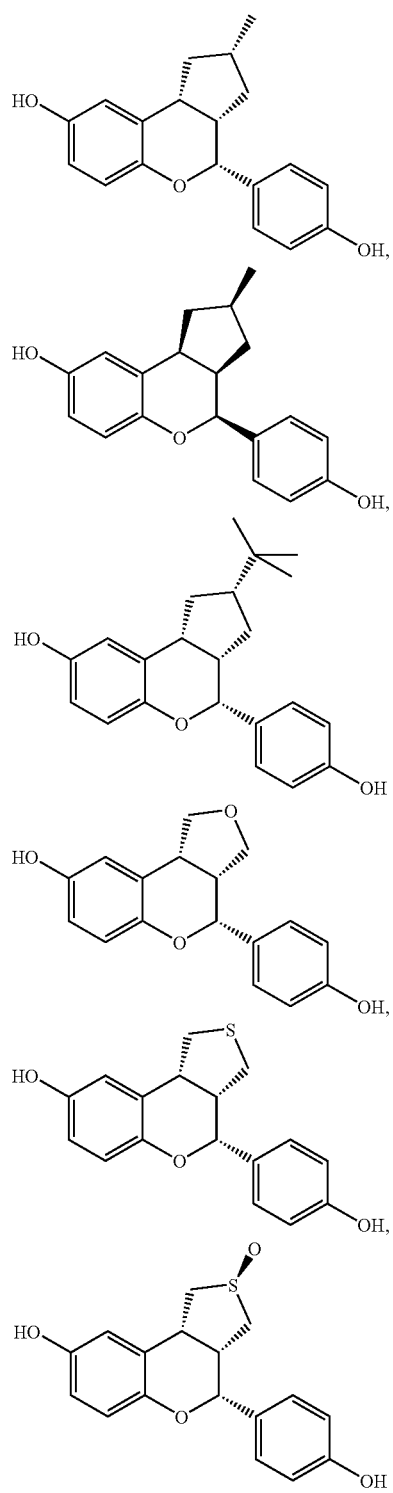

-continued

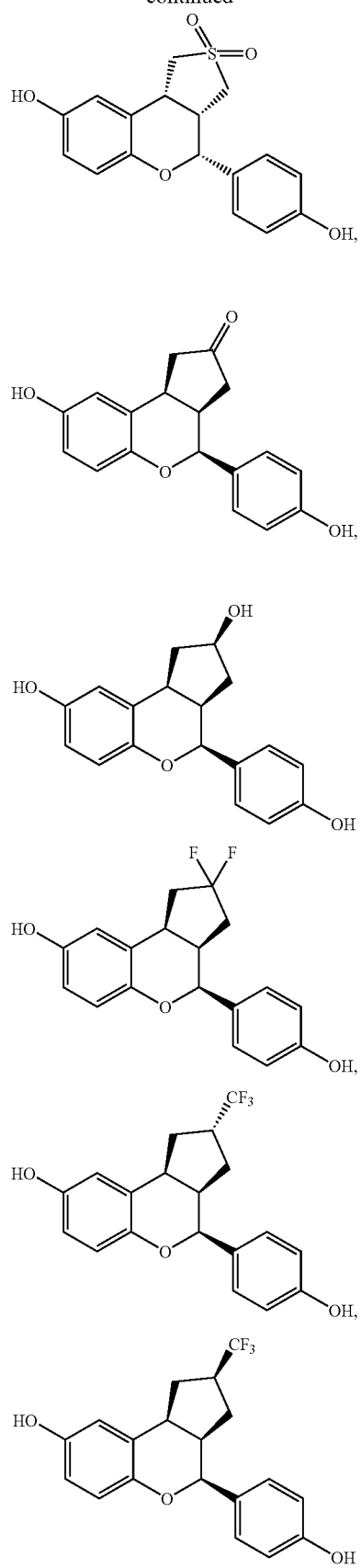

-continued
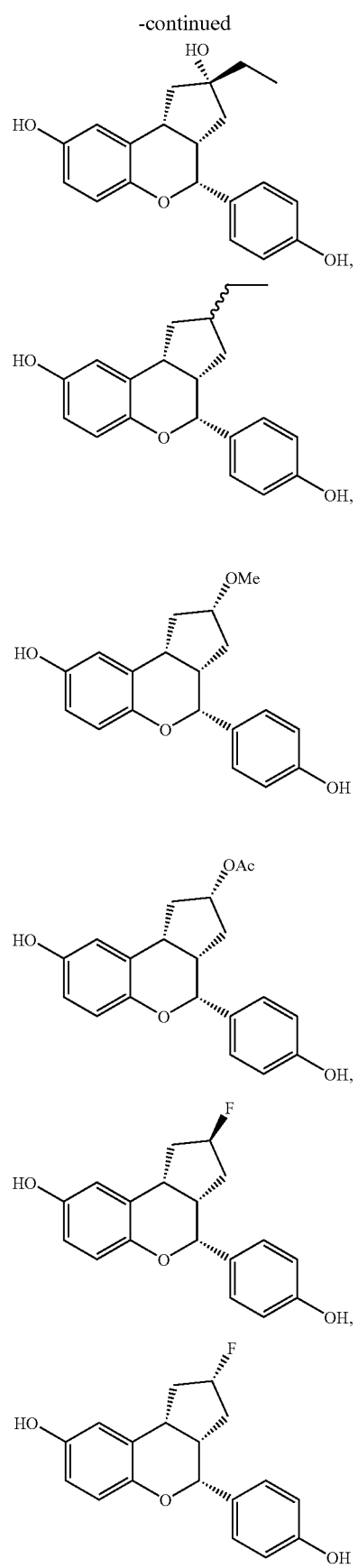
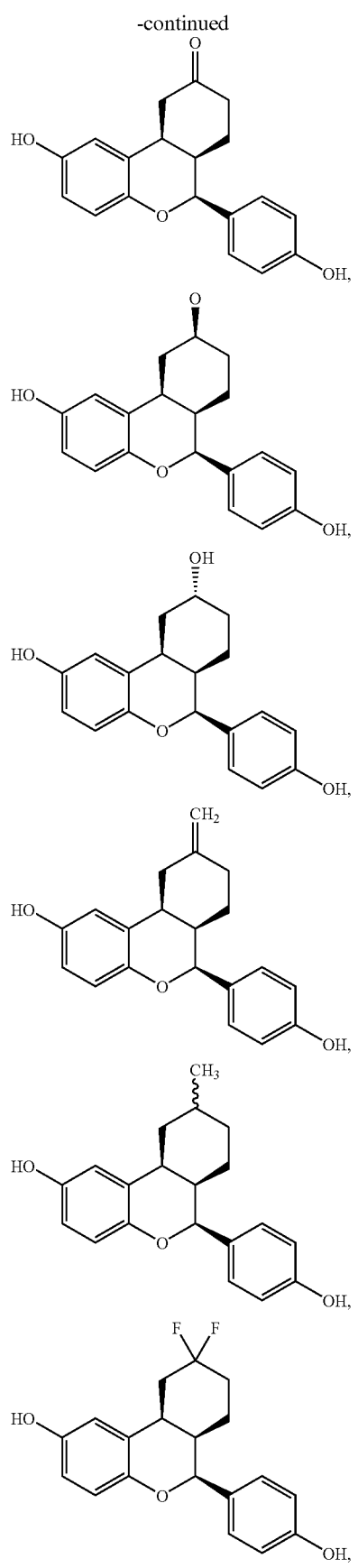

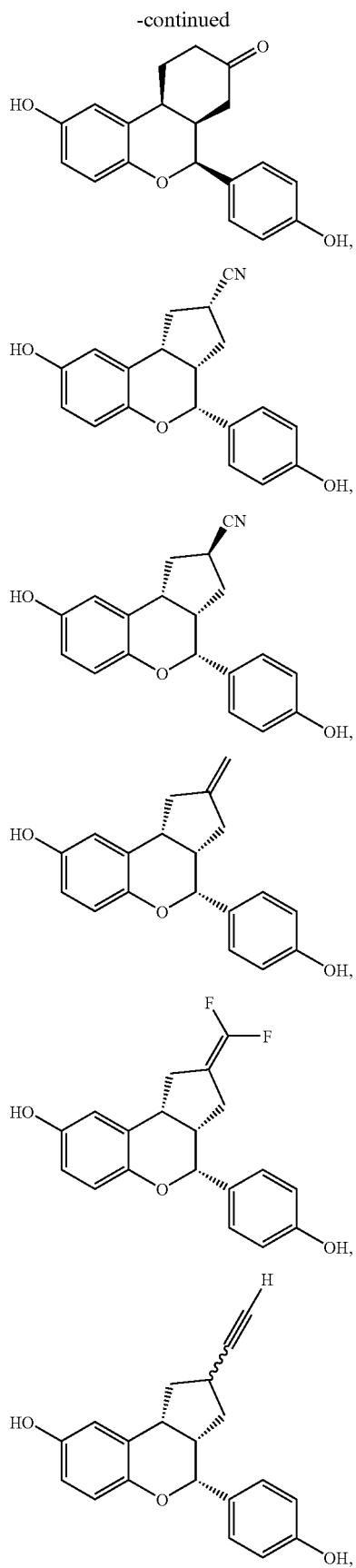
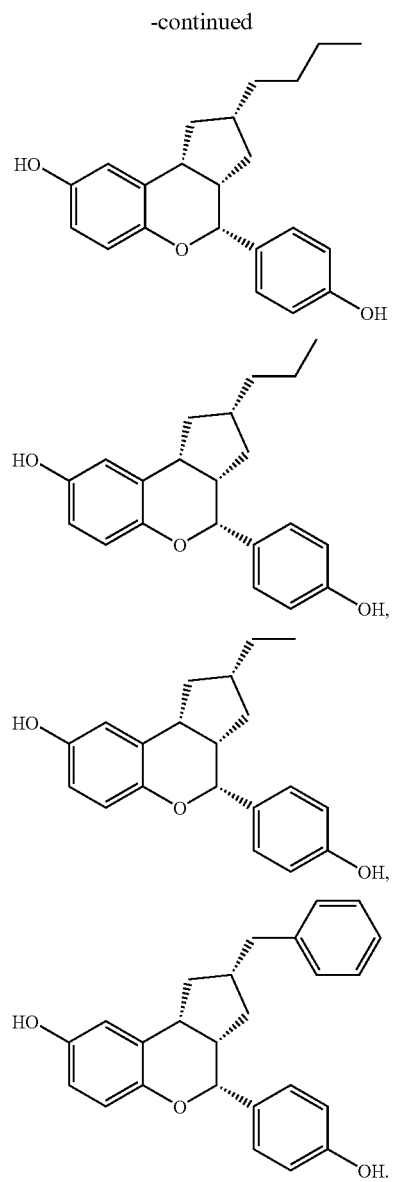
Reaction Schemes
Compounds of formula (I) and intermediates thereof can be prepared as described in Reaction Schemes A-J below. All substituents, unless otherwise indicated, are previously defined. The reagents and starting materials are readily available to one of ordinary skill in the art.
SCHEME A
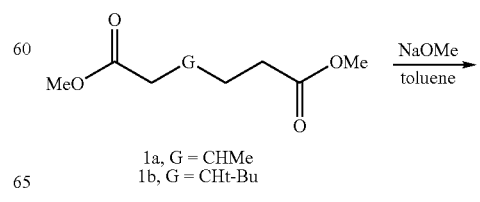
1a, G = CHMe
1b, G = CHt-Bu -continued

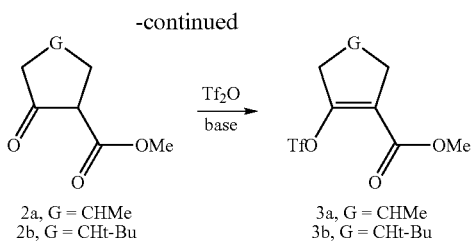

2a, G = CHMe
2b, G = CHt-Bu

3a, G = CHMe
3b, G = CHt-Bu

In scheme A, alkyl substituted 2-oxocyclopentanecarboxylates 2, wherein G is CHMe or CHt-Bu, were prepared using a Dieckmann cyclization of the alkyl substituted adipic acids 1, which are commercially available. To a heated solution of an appropriate base, such as NaOMe (sodium methoxide) in an appropriate solvent, such as toluene, an appropriate amount of 1 is added to give the corresponding 2-oxocyclopentanecarboxylates 2. The product of formula 2 can be isolated and purified by techniques well known in the art.

The 2-oxocyclopentanecarboxylates 2 are then reacted with an appropriate amount of trifluoromethanesulfonic (triflic) anhydride (Tf$_2$O) in the presence of an appropriate base, as would be known to one skilled in the art, such as 2,6-di-tert-butyl-4-methyl-pyridine or diisopropyl ethyl amine (iPr$_2$NEt), to form the triflates 3, wherein G is CHMe or CHt-Bu (tertiary-butyl). The reaction may be carried out at room temperature and the product 3 isolated and purified by methods well known in the art.

SCHEME B

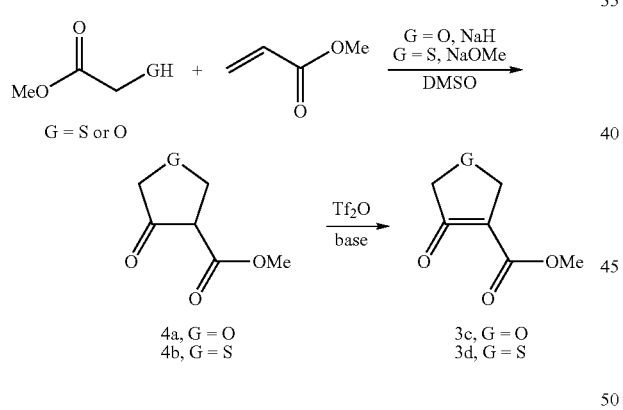

4a, G = O
4b, G = S

3c, G = O
3d, G = S

In scheme B, heterocycles 4, wherein G is either O or S, were prepared by Michael addition of methyl glycolate or methyl thioglycolate to methyl acrylate followed by Dieckmann cyclization in one pot. The methyl glycolate or methyl thioglycolate is added to a suspension of an appropriate base, preferably a metal hydride, such as sodium hydride (NaH) in ether and stirred until the evolution of H$_2$ gas ceases in the case of methyl glycolate or NaOMe in methanol, in the case of methyl thioglycolate. The residue is concentrated and dissolved in DMSO, cooled, and then methyl acrylate is added drop wise. The reaction mixture is then warmed to room temperature and stirred. The product 4 is then extracted and purified by methods well known in the art. The resulting heterocycles 4 are then reacted with Tf$_2$O in the presence of an appropriate base to form triflates 3, wherein G is oxygen (O) or sulfur (S).

SCHEME C

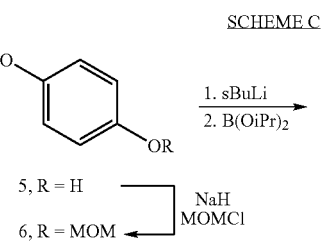

5, R = H
6, R = MOM

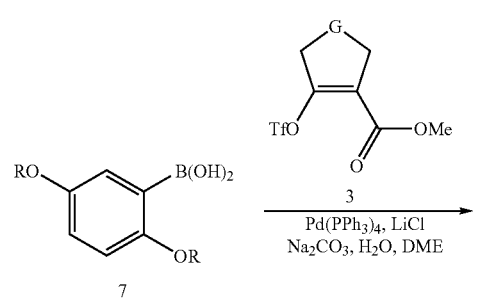

8a, G = CHMe
8b, G = CHt-Bu
8c, G = O
8d G = S
R = MOM

In scheme C, hydroquinone 5 is protected as the bis-methoxymethyl (MOM) ether using sodium hydride and chloromethyl methyl ether (MOMCl). Ortho lithiation of protected hydroquinone 6 may be accomplished with sec-butyllithium (sBuLi) followed by quenching with triisopropyl borate to form the boronic acid 7. Boronic acid 7 was coupled with triflates 3 using Suzuki conditions, using the reagents tetrakis (triphenylphosphine)palladium(0) (Pd(PPh$_3$)$_4$), lithium chloride (LiCl), sodium carbonate (Na$_2$CO$_3$), water and dimethoxyethane (DME) (Miyaura, N.; Suzuki, A. Chem. Rev. 1995, 95, 2457-2483) to give unsaturated esters 8, wherein G is either CHMe, CHt-Bu, O or S.

SCHEME D

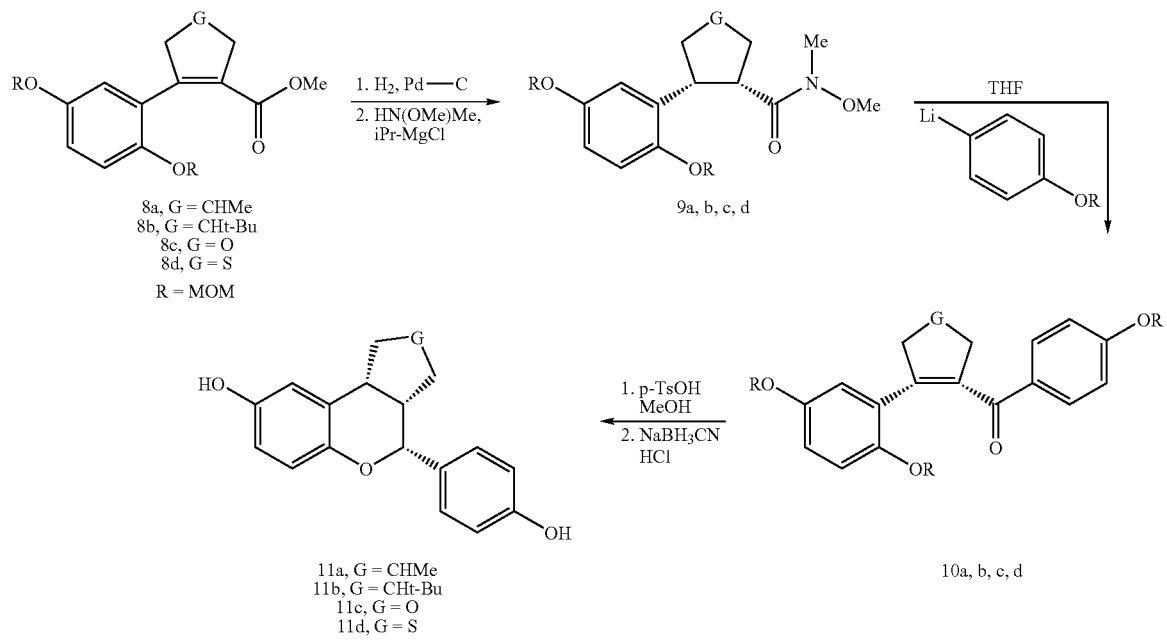

8a, G = CHMe
8b, G = CHt-Bu
8c, G = O
8d, G = S
R = MOM 9a, b, c, d

11a, G = CHMe
11b, G = CHt-Bu
11c, G = O
11d, G = S 10a, b, c, d

In scheme D, the unsaturated esters 8 as prepared in scheme C are hydrogenated over Palladium on carbon (Pd/C) and then transformed into Weinreb amides 9, using isopropylmagnesium chloride (iPr-MgCl) and N,O-dimethylhydroxylamine-HCl (HN(OMe)Me). The Weinreb amides 9 are then reacted with lithiated p-bromophenyl methoxymethyl ether in an appropriate solvent such as tetrahydrofuran (THF) to give the corresponding ketones 10. Deprotection and cyclization of ketones 10 under acidic conditions para-toluenesulfonic acid (p-TsOH) in methanol is followed by reduction in the same pot with sodium cyanoborohydride ($NaBH_3CN$). The reduction is kept acidic by addition of HCl which gives benzopyrans 11, wherein G is CHMe, CHt-Bu, O or S.

SCHEME E

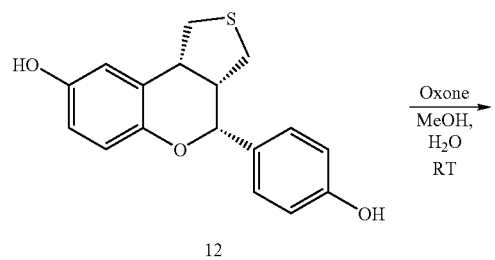

12

-continued

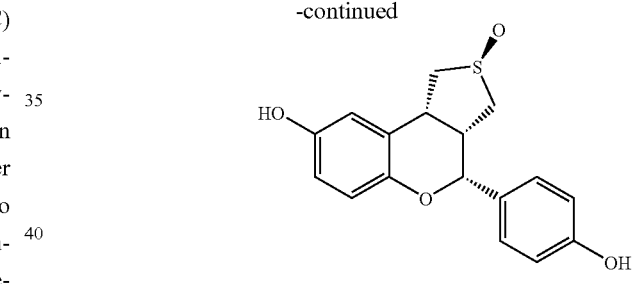

13

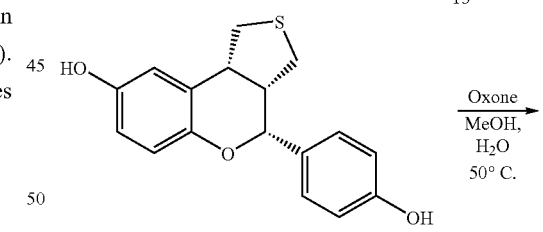

12

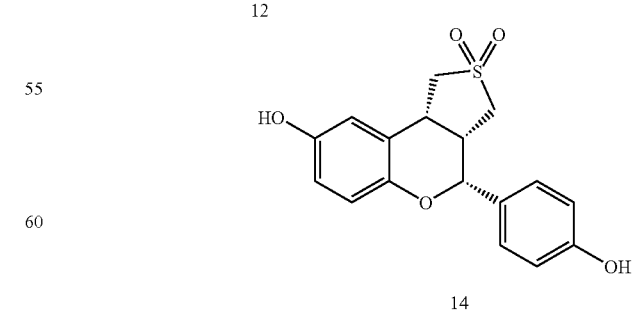

14

In scheme E, the tetrahydrothiophene 12, as prepared in scheme D (11d) may be oxidized to the sulfoxide 13 with potassium peroxymonosulfate (oxone) in MeOH and water at room temperature. The sulfone 14 is prepared from the tetrahydrothiophene 12 using the same conditions with heating at 50° and longer reaction times.

SCHEME F

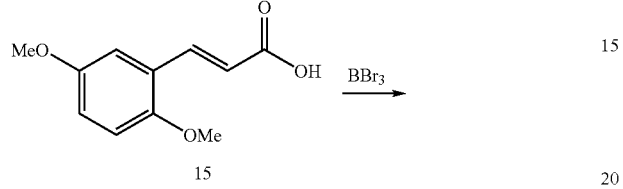

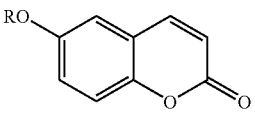

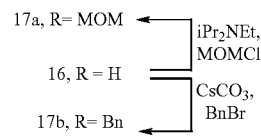

In scheme F, 2,5-dimethoxycinnamic acid 15 is treated with boron tribromide (BBr$_3$) to form 6-hydroxycoumarin 16. 6-Hydroxycoumarin 16 can be protected as the bis-methoxymethyl ether (MOM) 17a using N,N-diisopropylethylamine (iPr$_2$NEt) and MOMCl or as the benzyl ether (Bn) 17b using cesium carbonate (CsCO$_3$) and benzyl bromide (BnBr).

SCHEME G

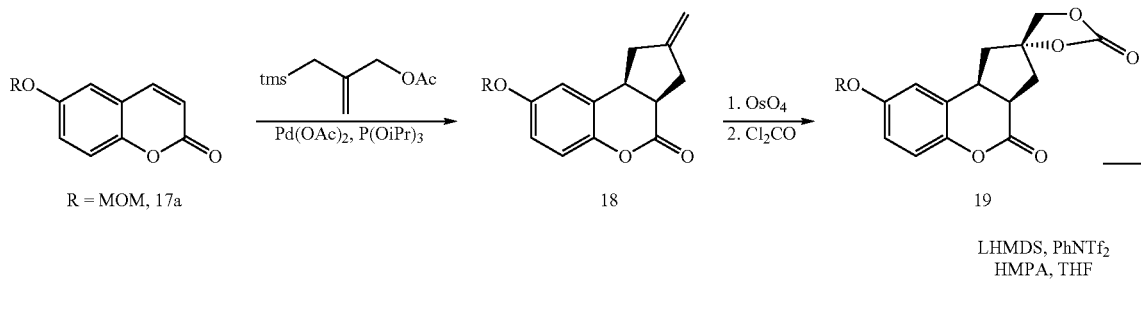

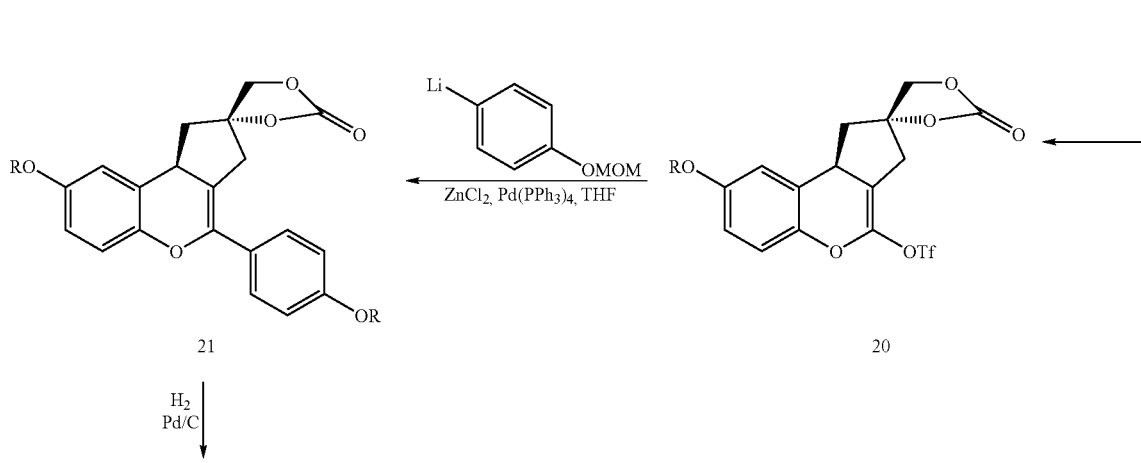

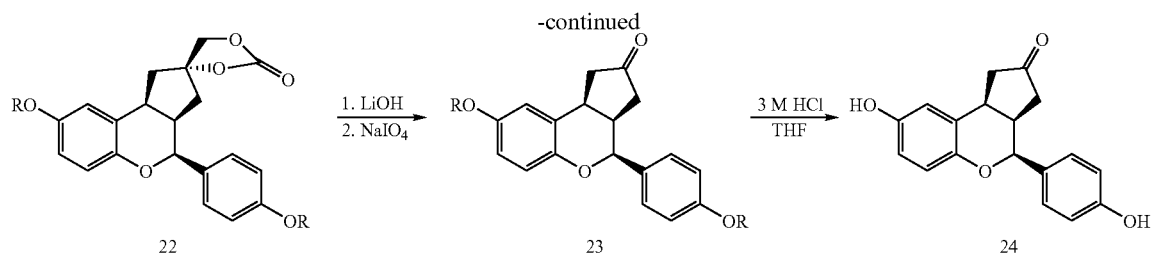

In scheme G, the cyclopentanoid 18 is formed via [3+2] cycloaddition to 6-methoxymethoxy coumarin 17a using Trost's trimethylenemethane chemistry by using 2-(acetyoxymethyl)allyl-triethylsilane, palladium acetate (Pd(OAc)$_2$) and triisopropyl phosphite (P(OiPr)$_3$) (Trost, B. M. *Angew. Chem. Int. Ed. Engl.* 1986, 25, 1-20). The exomethylene of 18 is dihydroxylated using osmium tetroxide (OsO$_4$) and N-methylmorpholine N-oxide followed by protection of the diol using phosgene (Cl$_2$CO) to give the cyclic carbonate 19. The enol triflate 20 is then formed by deprotonating 19 with an appropriate base, as known by one skilled in the art, such as lithium bis(trimethylsilyl)amide (LHMDS) followed by trapping the enolate with N-phenyltrifluoromethanesulfonimide (PhNTf$_2$) in the presence of hexamethylphosphoramide [HMPA] in an appropriate solvent, such as THF. The enol triflate 20 was coupled with lithiated p-bromophenyl methoxymethyl ether using Negishi conditions using zinc chloride (ZnCl$_2$), Pd(PPh$_3$)$_4$, in an appropriate solvent, such as THF (Negishi, E. *Acc. Chem. Res.* 1982, 15, 340-348) to give flavene 21. The enol of flavene 21 is reduced with hydrogen over Pd/C in an appropriate solvent such as THF and methanol to give flavan 22. The carbonate of flavan 22 is then hydrolyzed with an appropriate base, such as lithium hydroxide (LiOH), followed by oxidative cleavage of the diol with an appropriate oxidant such as sodium periodate (NaIO$_4$) in one pot to give the cyclopentanone 23. The methoxymethyl protecting groups of 23 could then be removed using appropriate acidic conditions such as 3M HCl in THF to give the cyclopentanone 24, wherein G is C=O.

SCHEME H

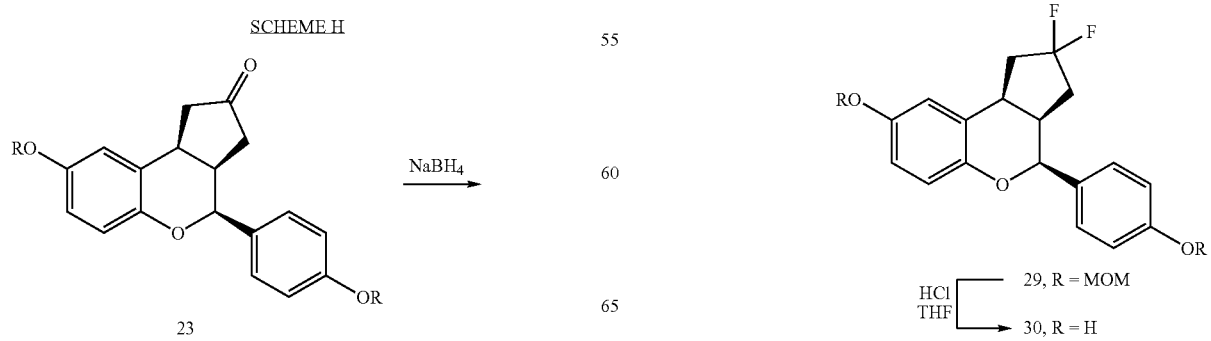

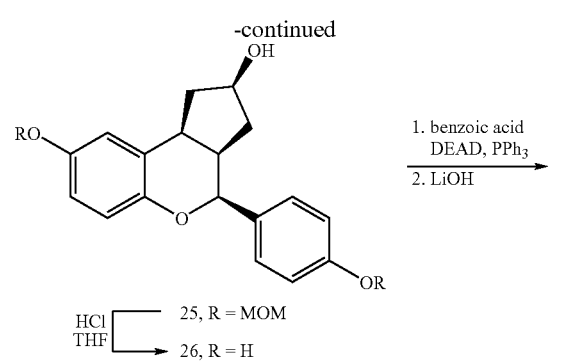

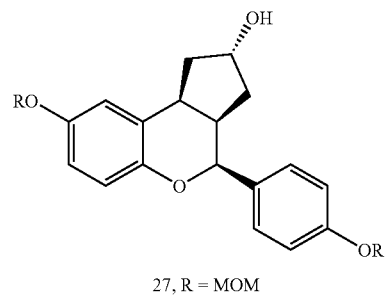

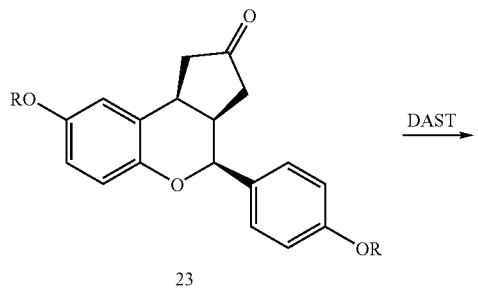

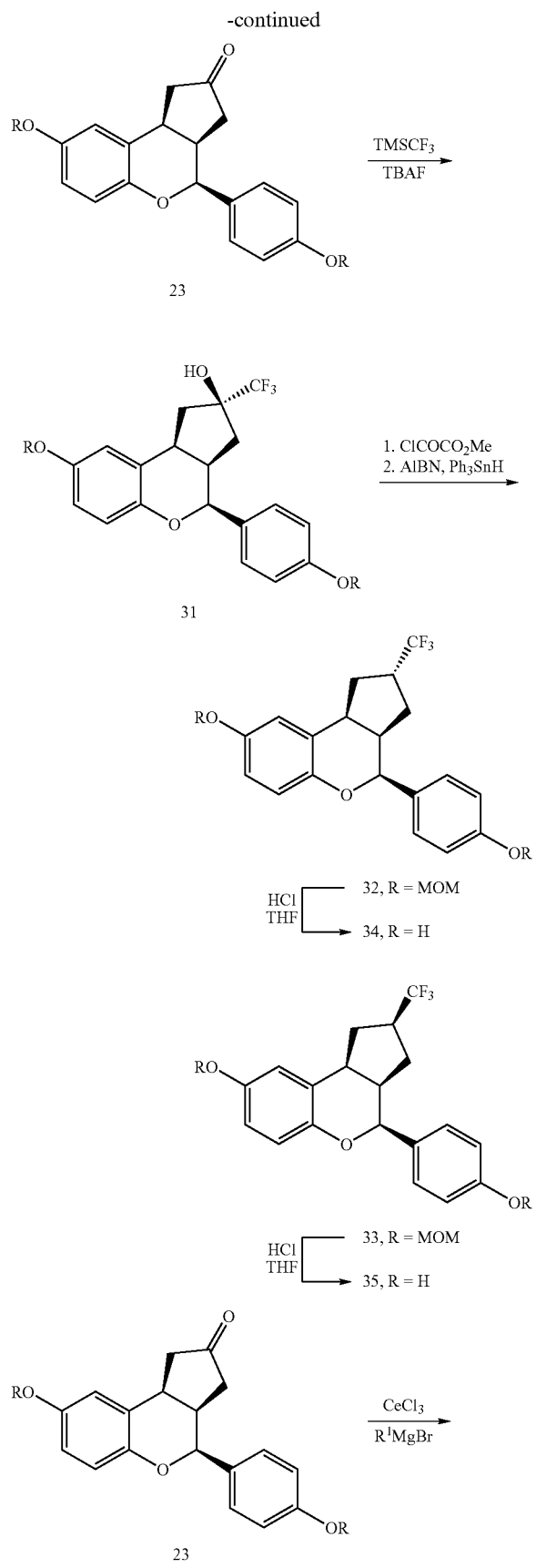
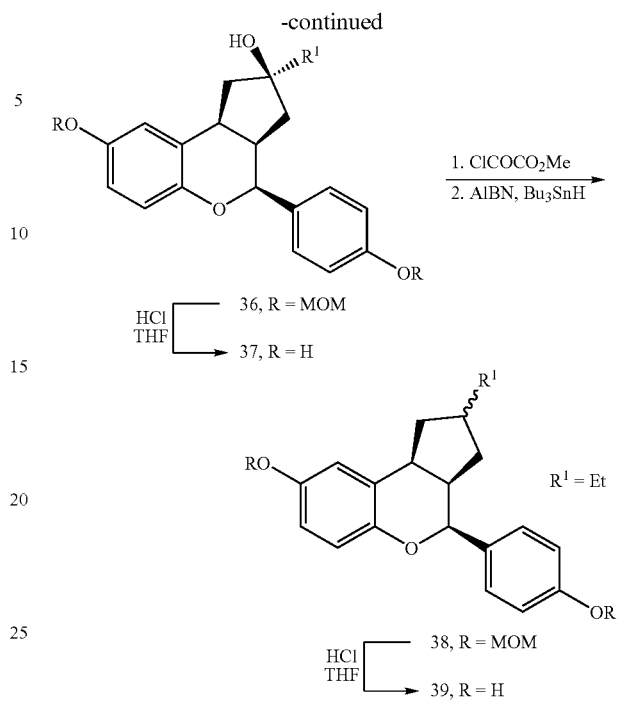

In scheme H, cyclopentanone 23 may be reduced with an appropriate reductant, such as sodium borohydride (NaBH$_4$), to give alcohol 25 as a single diastereomer which is then deprotected, as described above in scheme G, to give alcohol 26, wherein G is CHOH. Alcohol 25 was inverted using Mitsunobu conditions, using benzoic acid, diethyl azodicarboxylate (DEAD), triphenylphosphine (PPh$_3$) (Mitsunobu, O. Synthesis, 1981, 1-28.), followed by hydrolysis of the benzoate with an appropriate base, such as, lithium hydroxide (LiOH), to give alcohol 27, wherein G is CHOH. Cyclopentanone 23 is treated with (diethylamino)sulfur trifluoride (DAST) to give difluorocyclopentane 29 which is deprotected under acid conditions, such as HCl in THF, to give difluorocyclopentane 30, wherein G is CF$_2$. Cyclopentanone 23 is reacted with (trifluoromethyl)trimethylsilane (TMSCF$_3$) in the presence of tetra-butyl ammonium fluoride (TBAF) to give alcohol 31. Radical deoxygenation of 31 is accomplished via the methyl oxalyl ester (formed using methyl chloroglyoxylate (ClCOCO$_2$Me), DMAP, and Et$_3$N), using triphenyltin hydride (Bu$_3$SnH) and 2,2'-Azobisisobutyronitrile (AIBN) as described by Dolan (Dolan, S. C.; MacMillan, J. J. Chem. Soc., Chem. Commun. 1985, 1588-1589) to give trifluoromethyls 32 and 33 as a separable mixture of diastereomers. The diastereomers are then separately deprotected, under acidic conditions, such as HCl in THF, to give trifluoromethyls 34 and 35, wherein G is CHCF$_3$. Cyclopenanone 23 was reacted with Grignard reagents (R$^1$MgBr, for example) in the presence of cerium trichloride (CeCl$_3$) to give alcohols 36 which are deprotected under acidic conditions, such as HCl in THF, to give alcohols 37. Radical deoxygenation of 36 was accomplished as described above for 31 to give alkyl substituted cyclopentanes 38 which are deprotected to give alkyl cyclopentanes 39, wherein G is CHEt (ethyl). One skilled in the art would know how to make other equivalent benzopyrans wherein G is CH(C$_1$-C$_6$) lower alkyl, by the appropriate Grignard reagent.

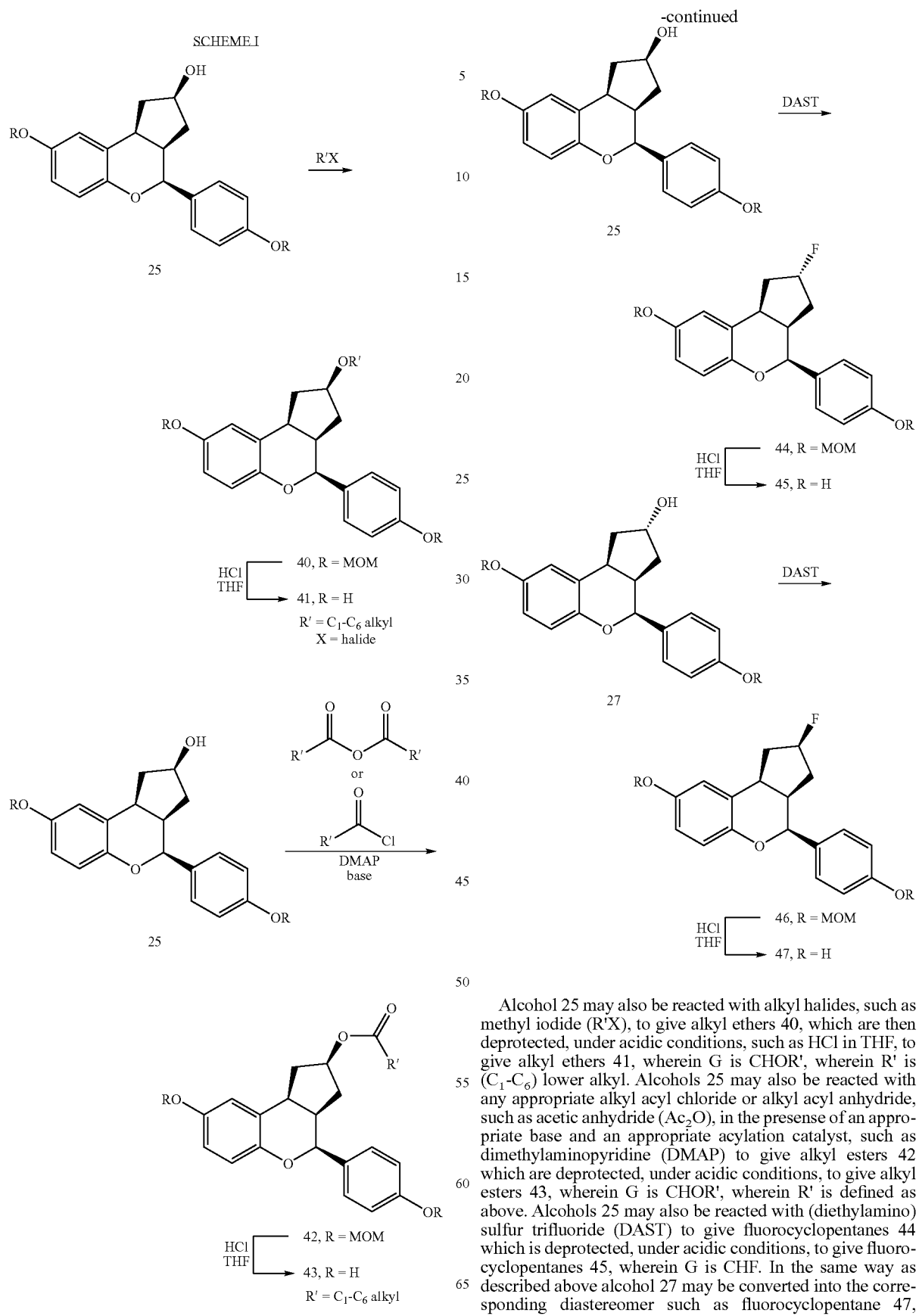

Alcohol 25 may also be reacted with alkyl halides, such as methyl iodide (R'X), to give alkyl ethers 40, which are then deprotected, under acidic conditions, such as HCl in THF, to give alkyl ethers 41, wherein G is CHOR', wherein R' is ($C_1$-$C_6$) lower alkyl. Alcohols 25 may also be reacted with any appropriate alkyl acyl chloride or alkyl acyl anhydride, such as acetic anhydride ($Ac_2O$), in the presense of an appropriate base and an appropriate acylation catalyst, such as dimethylaminopyridine (DMAP) to give alkyl esters 42 which are deprotected, under acidic conditions, to give alkyl esters 43, wherein G is CHOR', wherein R' is defined as above. Alcohols 25 may also be reacted with (diethylamino) sulfur trifluoride (DAST) to give fluorocyclopentanes 44 which is deprotected, under acidic conditions, to give fluorocyclopentanes 45, wherein G is CHF. In the same way as described above alcohol 27 may be converted into the corresponding diastereomer such as fluorocyclopentane 47, wherein G is CHF.

Compounds of formula (II) and intermediates thereof can be prepared as described in Reaction Schemes J-O below. All substituents, unless otherwise indicated, are previously defined. The reagents and starting materials are readily available to one of ordinary skill in the art.

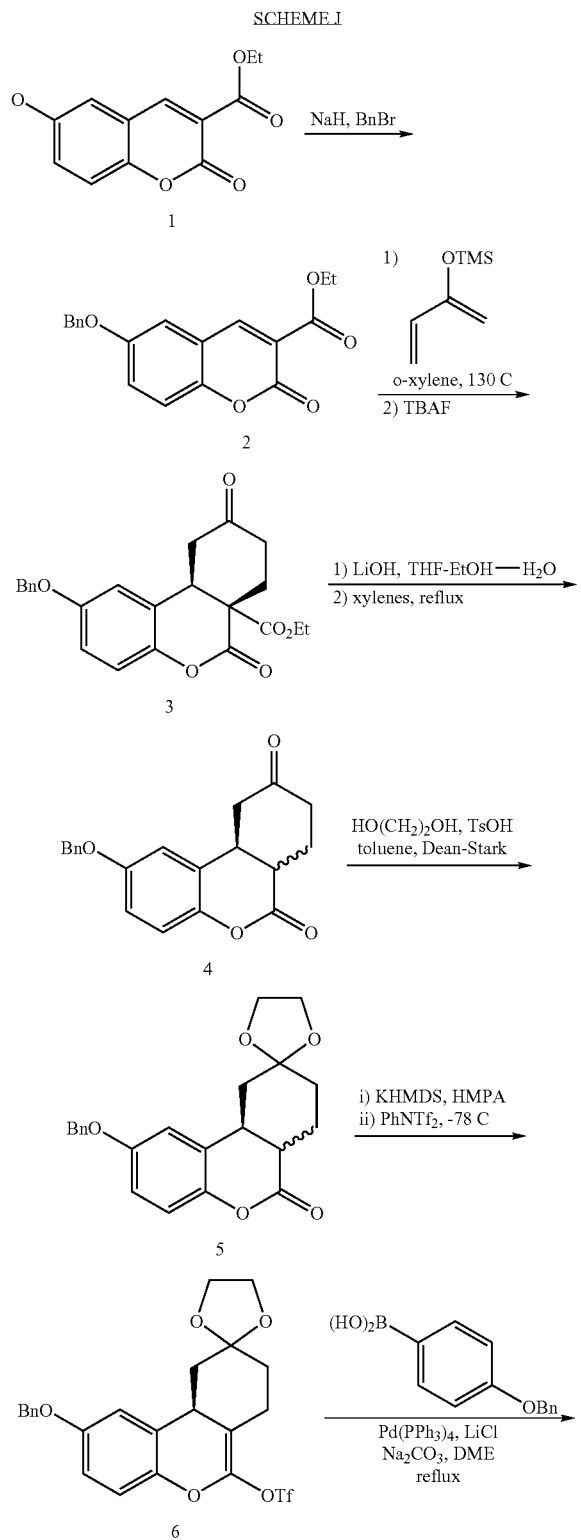

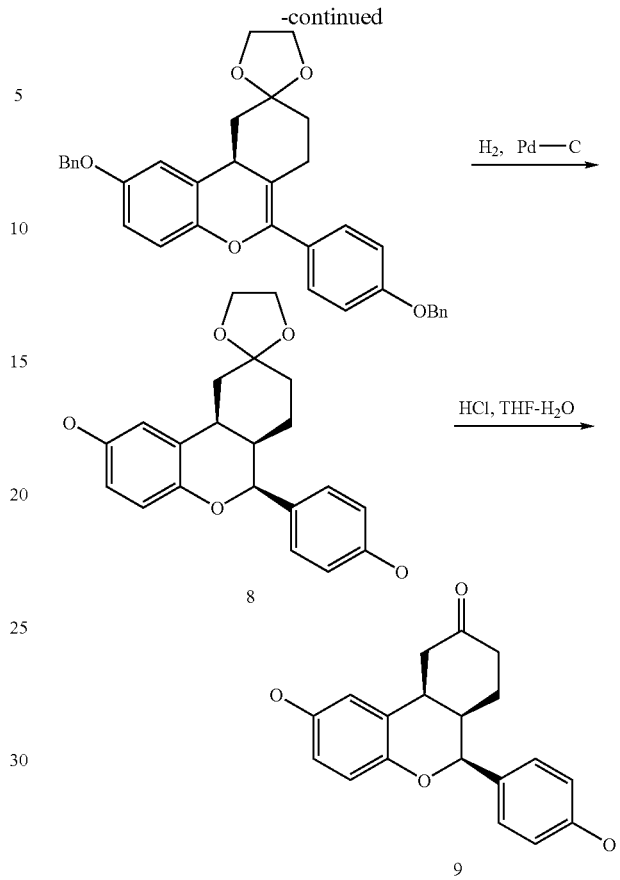

Beginning with the known hydroxy-coumarin 1 (Cramer, Chem. Ber. 1956, 89, 354), protection of the phenol as its benzyl ether using an appropriate metal hydride, such as sodium hydride (NaH) with an appropriate benzylating agent such as benzyl bromide (BnBr), as would be known by one skilled in the art, provides coumarin 2. Diels-Alder reaction with 2-trimethylsilyloxy-1,3-butadiene in solvent such as ortho-xylene, at a temperature of approximately 130° C., followed by workup of the reaction in a desilylating agent, such as tetrabutylammonium fluoride (TBAF), provides the desired cycloaddition product 3. A two-step decarboxylation provides keto-lactone 4, by first treating compound 3 with a hydroxide source, such as lithium hydroxide (LiOH) in an appropriate solvent mixture, such at tetrahydrofuran (THF), ethanol and water, followed by refluxing of the intermediate carboxylic acid in an appropriate solvent, such as xylenes. Ketone 4 is selectively protected as it cyclic acetal 5, by treating ketone 4 with the protecting agent ethylene glycol (HO(CH$_2$)$_2$OH), in the presence of a suitable acid, such as para-toluene sulfonic acid (TsOH) in a suitable solvent, such as toluene, using a Dean-Stark apparatus, as is known by one skilled in the art. Treatment of the lactone 5 with a suitable base, such as potassium hexamethyldisilazane (KHMDS) in the prescence of stoichiometric hexamethylphosphoramide (HMPA), followed by quenching of the enolate with a suitable triflating source such as N-phenyl triflamide (PhNTf$_2$) provides the intermediate enol triflate 6 as a clear solid. Suzuki cross-coupling of 6 with parabenzyloxyphenylboronic acid, in the presence of chloride salt, such as lithium chloride (LiCl), and a suitable base, such as sodium carbonate (Na$_2$CO$_3$), using a metal catalyst such as palladium-tetrakis triphenylphosphine (Pd(PPh$_3$)$_4$) in a suitable solvent, such as ethylene glycol dimethyl ether (DME) provides the enol ether 7 under reflux. Hydrogenation of the benzyl ethers and the alkene of 7 using a metal catalyst, such palladium on carbon (Pd—C) in a protic solvent, such as methanol under a hydrogen atmosphere, affords diphenol 8. This step is followed by acid-promoted cleavage of the ketal protecting group, using an acid such as HCl in an appropriate solvent, such as THF/H$_2$O, affords the desired ketone 9 in good yield.

Furthermore in scheme L, protection of 9 as its bis-tertbutyldimethylsilyl ether (TBS) using an appropriate silylating agent, such as tertbutyldimethylsilyl chloride (TBS-Cl) in the presence of an appropriate base, such as imidazole, provides bis-silyl ether 12. Alternatively, protection of 9 as its bis-methoxymethyl ether (MOM) 13, using an appropriate protecting agent such methoxymethyl chloride (MOM-Cl), in the presence of an appropriate base, such as potassium tert-butoxide (KOtBu), in an appropriate solvent, such as dimethylformamide (DMF) provides bis-ether 13.

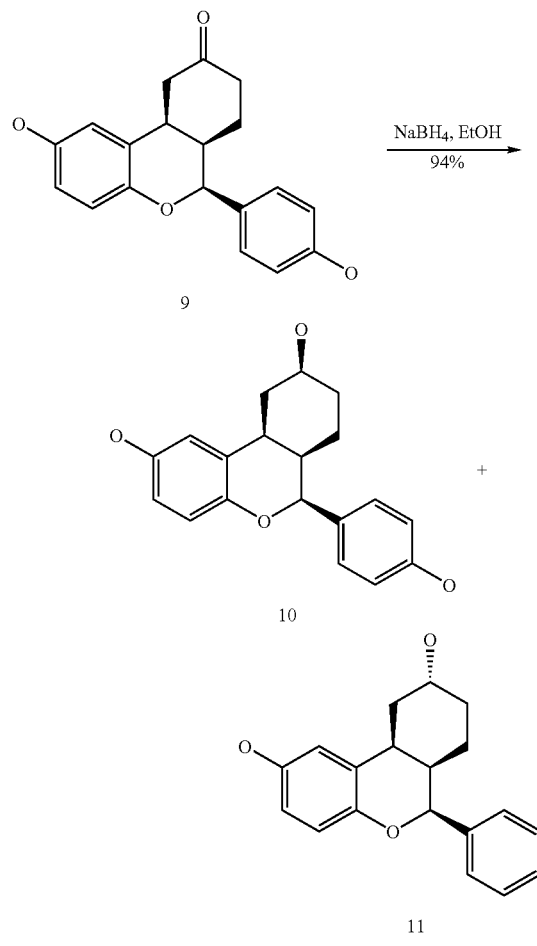

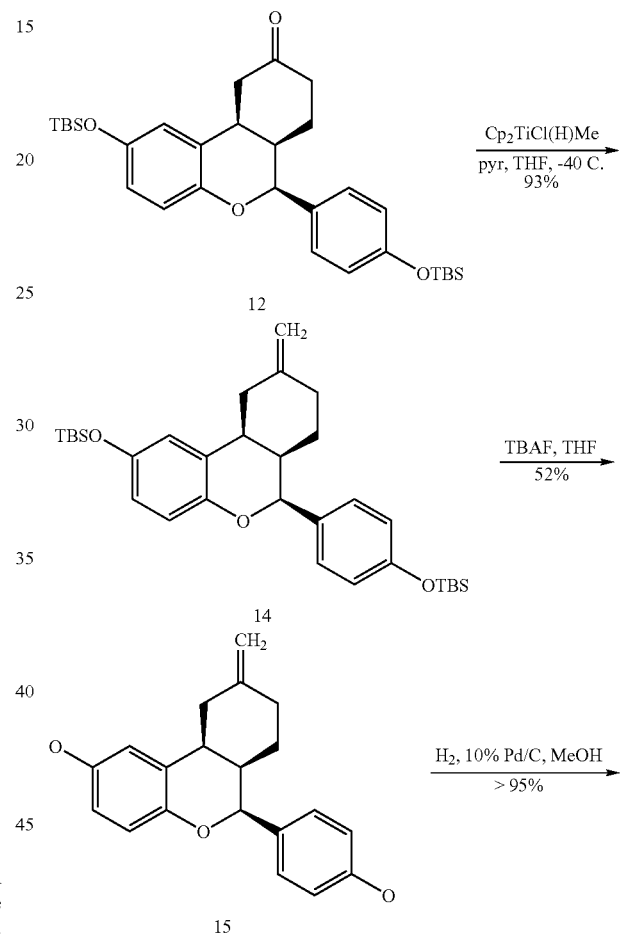

Analogues of 9 are generated in the schemes K-M. In scheme K, sodium borohydride (NaBH$_4$) reduction of the ketone 9, in a suitable protic solvent, such as ethanol, provides an approximately 2:1 ratio of epimers 10 and 11.

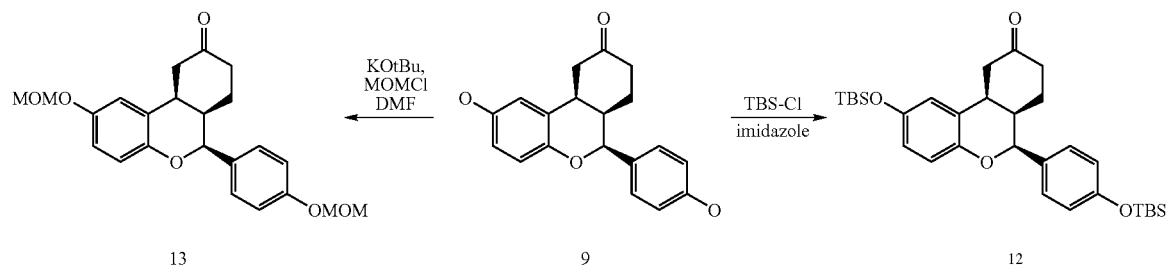

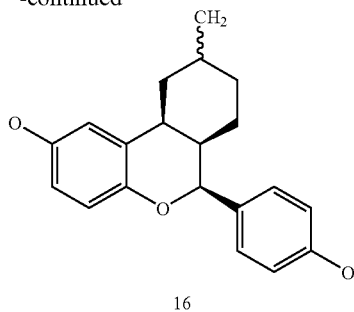

Bis silyl ether 12 is treated with the Tebbe reagent (CP$_2$TiCl(H)Me), in the presence of pyridine base, in an appropriate solvent, such as THF, at a temperature range of −35-50° C., affords the alkenylated product 14. Desilylation with an appropriate fluoride source, such as TBAF, with an appropriate solvent, such as THF, provides exo-methylene 15, which is then hydrogenated with a suitable metal catalyst, such as Pd—C, in an appropriate protic solvent, such as methanol, under an atmosphere of hydrogen, to provide an approximately 1:1 mixture of inseparable methylated product 16.

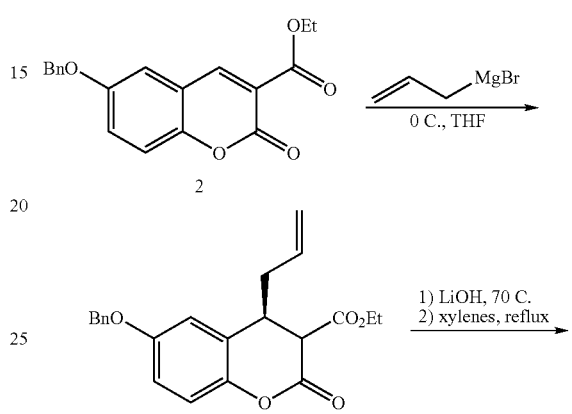

In scheme N, treatment of the bis-MOM ether 13 from scheme K, with a fluorinating source, such as (diethylamino)sulfur trifluoride (DAST) at 45° C., in a suitable chlorinated solvent, such as 1,2-dichloroethane (1,2-DCE), affords the gem-difluoro intermediate 17. Removal of the MOM protecting groups is carried out with a suitable acid, such HCl, in an appropriate solvent mixture, such as THF, in the presence of water affords the desired difluoride 18.

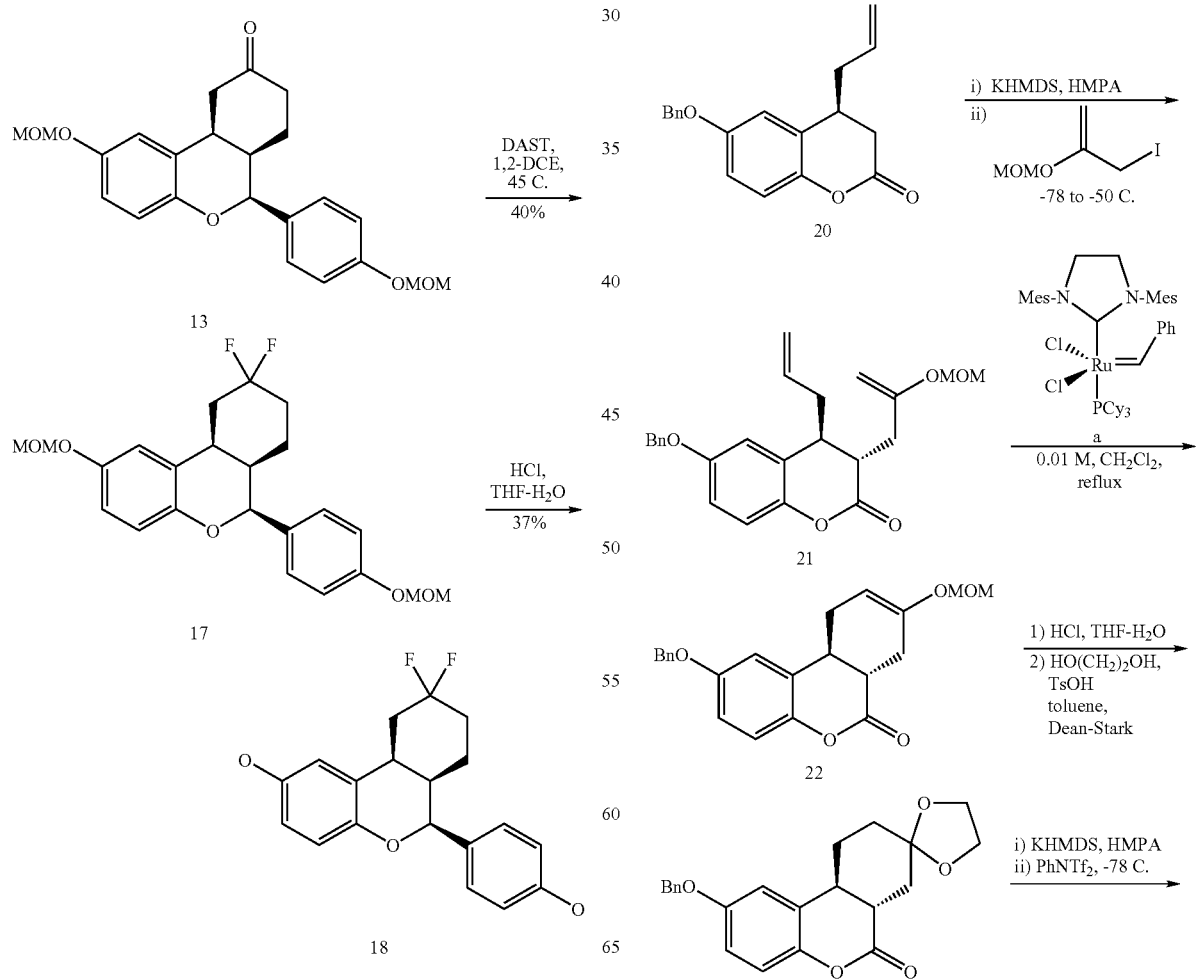

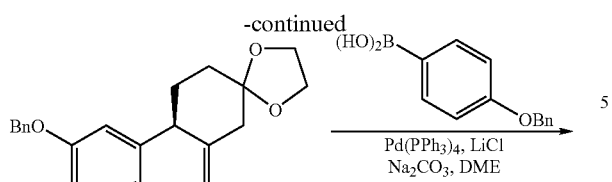

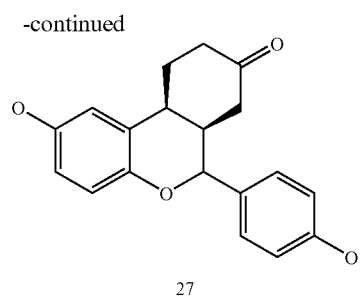

27

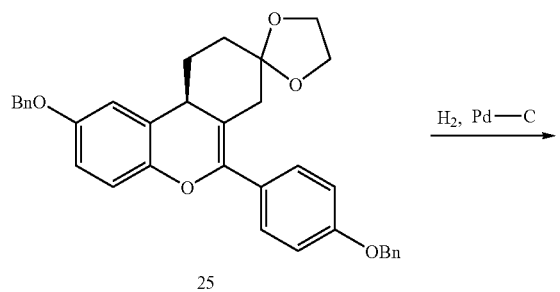

25

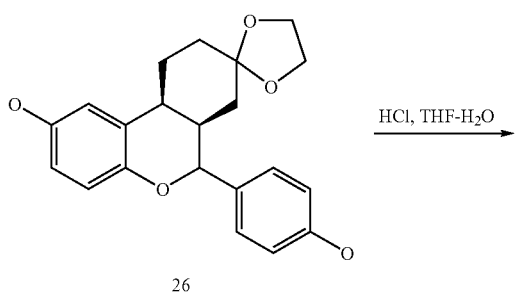

26

In scheme O, the synthesis of isomeric ketone 27 is carried out in the manner described below. Allyl-Grignard addition, using an appropriate allyl-Grignard reagent, such as allylmagnesium bromide at low temperature, such as 0° C., in a suitable ethereal solvent, such as THF, to the aforementioned coumarin 2, from scheme J, in a 1,4 sense provides the β-keto ester 19. Decarboxylation of 19 to 20 occurs under identical conditions as the conversion of 3 to 4 as described in scheme J. Deprotonation of 20 using an appropriate base, such as KHMDS, in the presence of HMPA, followed by reaction of the enolate with an appropriate allylating reagent, such as 2-methoxymethyl-allyl iodide provides allylated 21. Ring closing metathesis of 21 using an appropriate Grubbs reagent a, such as [1,3-bis-(2,4,6-trimethylphenyl)-2-imidazolidinylidene)dichloro(phenylmethylene)-tricyclohexylphosphine)ruthenium], in a suitable chlorinated solvent, such as methylene chloride ($CH_2Cl_2$), at a concentration of 0.01M at reflux, affords the cyclic enol-ether 22. Hydrolysis of the enol ether, using an appropriate acid, such as HCl, in an ethereal solvent, such as THF containing water provides the intermediate ketone, which is converted to ketal 23 under identical conditions as described above for the conversion of 4 to 5 in scheme K. Conversion of the ketal 23 to final ketone 27 identically follows the conversion of ketal 5 to ketone 9 as described in scheme J.

SCHEME P

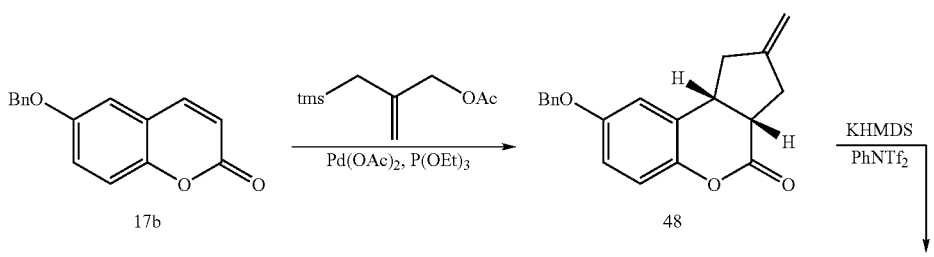

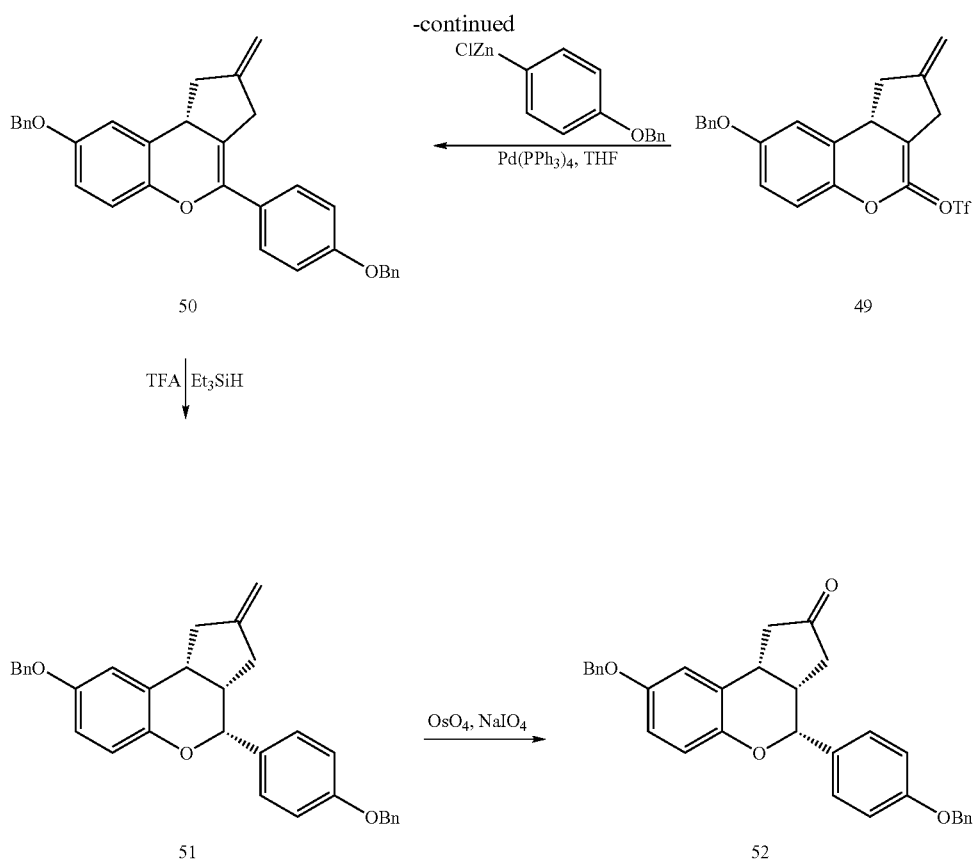

In Scheme P, an alternative synthesis of cyclopentanone 24 with benzyl protecting groups on the phenols is described. The cyclopentanoid 48 is formed via [3+2] cycloaddition to 8-benzyloxy coumarin 17b using Trost's trimethylenemethane chemistry using 2-(acetyoxymethyl)allyl-triethylsilane, palladium acetate (Pd(OAc)$_2$) and triisopropyl phosphite (P(OiPr)$_3$) (Trost, B. M. *Angew. Chem. Int. Ed. Engl.* 1986, 25, 1-20). The enol triflate 49 is then formed by deprotonating 48 with an appropriate base, as known by one skilled in the art, such as potassium bis(trimethylsilyl)amide (KHMDS) followed by trapping the enolate with an appropriate triflating agent such as N-phenyltrifluoromethanesulfonimide (PhNTf$_2$) in an appropriate solvent, such as THF. The enol triflate 49 can be coupled using Negishi conditions with the aryl zinc derived from p-bromophenylbenzyl ether, an appropriate palladium catalyst such as Pd(PPh$_3$)$_4$, in an appropriate solvent, such as THF (Negishi, E. *Acc. Chem. Res.* 1982, 15, 340-348) to give flavene 50. The enol of flavene 50 is reduced with triethylsilane (Et$_3$SiH) in the presence of trifluoroacetic acid (TFA) in methylene chloride to give flavan 51. The exomethylene of 51 is dihydroxylated using osmium tetroxide (OsO$_4$) and N-methylmorpholine-N-oxide (MO) followed by oxidative cleavage of the diol with an appropriate oxidant such as sodium periodate (NaIO$_4$) in one pot to give the cyclopentanone 52.

SCHEME Q

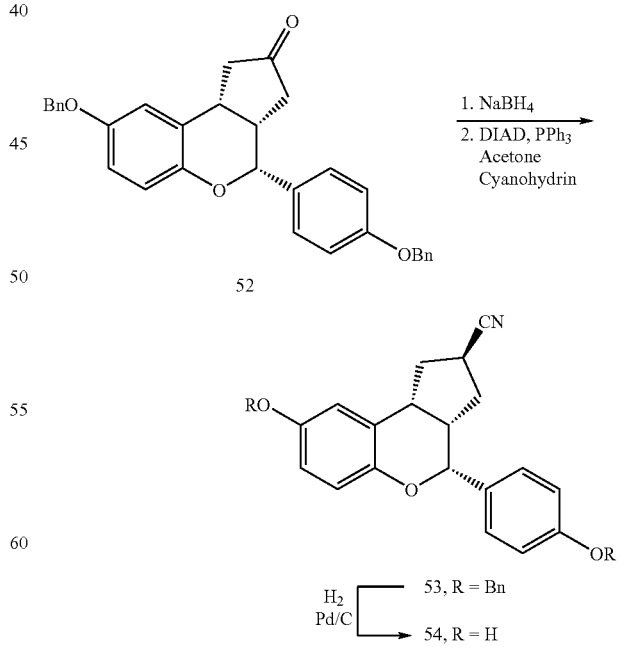

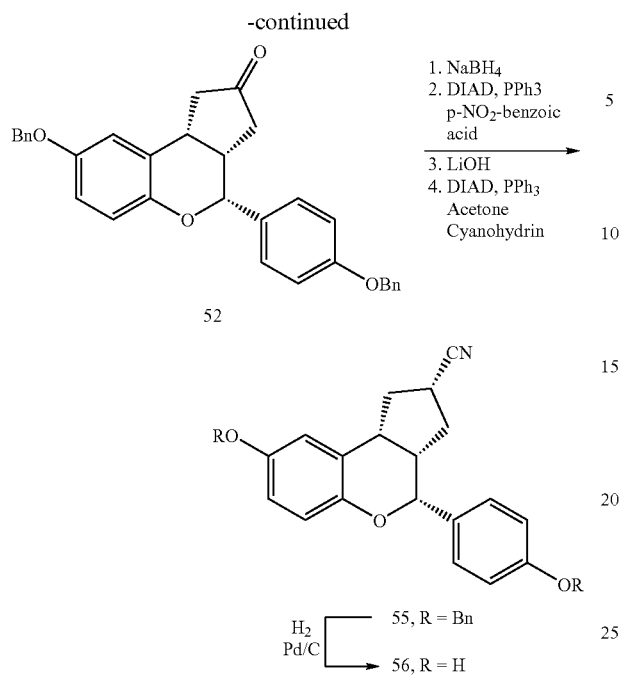

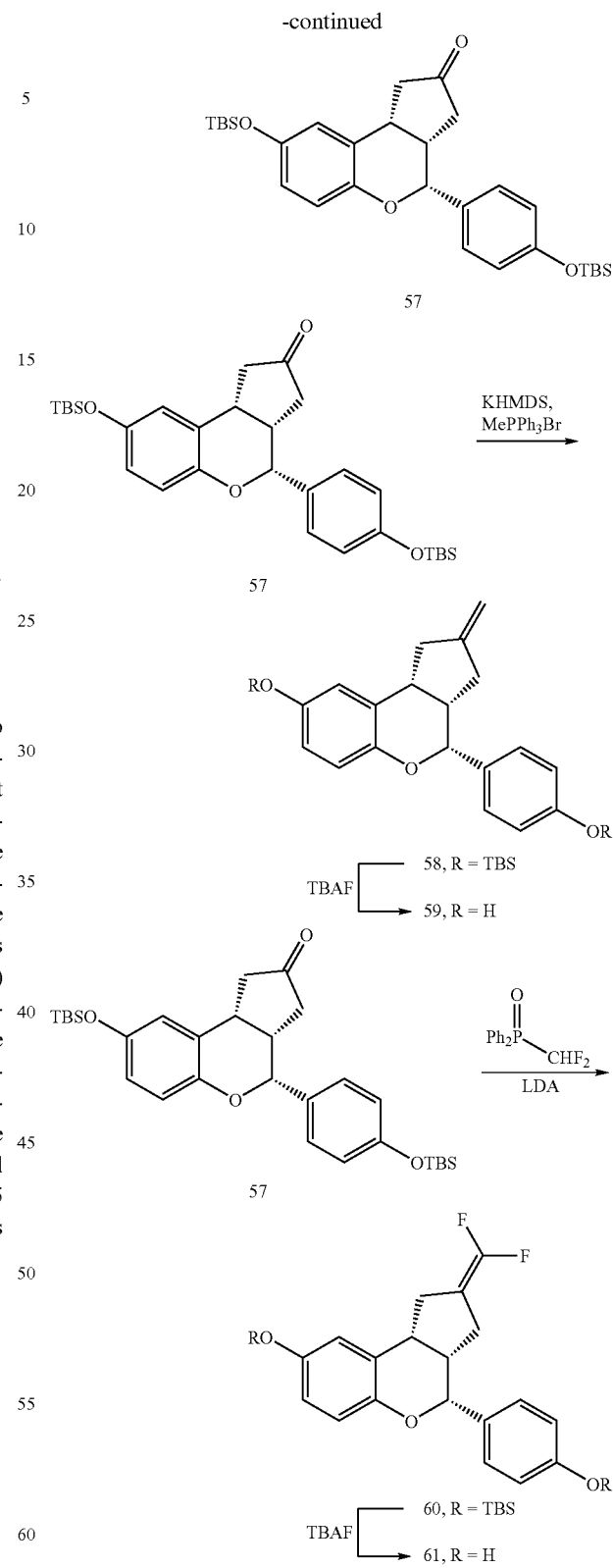

In Scheme Q, cyclopentanone 52 is converted into two nitrile substituted diastereomers. The ketone of cyclopentanone 52 can be reduced with an appropriate hydride reagent such as sodium borohydride (NaBH$_4$) followed by displacement of the resulting alcohol with cyanide using acetone cyanohydrin under appropriate Mitsunobu conditions (Mitsunobu, O. *Synthesis* 1981, 1-28) to afford nitrile 53. Nitrile 53 is deprotected using appropriate hydrogenation conditions such as 10% palladium on carbon (Pd/C) and hydrogen (H$_2$) to give deprotected nitrile 54. To obtain the opposite diastereomer, the ketone of cyclopentanone 52 is reduced to the alcohol as described above and then inverted using p-nitrobenzoic acid under appropriate Mitsunobu conditions followed by hydrolysis of the benzoate using lithium hydroxide (LiOH) followed by displacement of the resulting alcohol with cyanide as described above to afford nitrile 55. Nitrile 55 is deprotected using appropriate hydrogenation conditions as described above to give deprotected nitrile 56.

SCHEME R

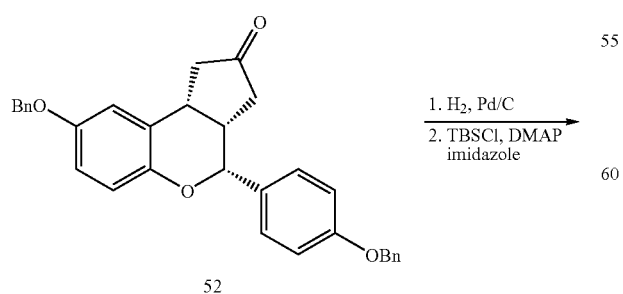

In scheme R, the benzyl protecting groups of cyclopentanone 52 are exchanged for silyl protecting groups. The benzyl protecting groups are removed using appropriate hydrogenation conditions such as 10% palladium on carbon (Pd/C) and hydrogen (H₂) followed by reaction with tri-tert-butylsilyl chloride (TBSCl), catalytic N,N-dimethylaminopyrindine (DMAP), and imidazole in dimethylformamide (DMF) to give silyl protected cyclopentanone 57. Silyl protected cyclopentanone 57 is reacted with the phosphonium ylide prepared from methyltriphenylphosphonium bromide and potassium hexamethyldisilazane (KHMDS) to give alkene 58. Alkene 58 is deprotected using tetrabutylammonium fluoride (TBAF) to afford deprotected alkene 59. Silyl protected cyclopentanone 57 is reacted with the lithium anion of (Difluoromethyl)diphenylphosphine oxide using the conditions described by Edwards et al. (Edwards, M. L.; Stemerick, D. M.; Jarvi, E. T.; Matthews, D. P.; McCarthy, J. R. *Tetrahedron Lett.* 1990, 31, 5571-5574) to give difluoromethylene 60. Difluoromethylene 60 can be deprotected using TBAF to give deprotected difluoromethylene 61.

1588-1589) to give alkyne 62 as a 5:1 mixture of diastereomers. Alkyne 62 was deprotected with TBAF to give deprotected alkyne 63 as a 5:1 mixture of diastereomers.

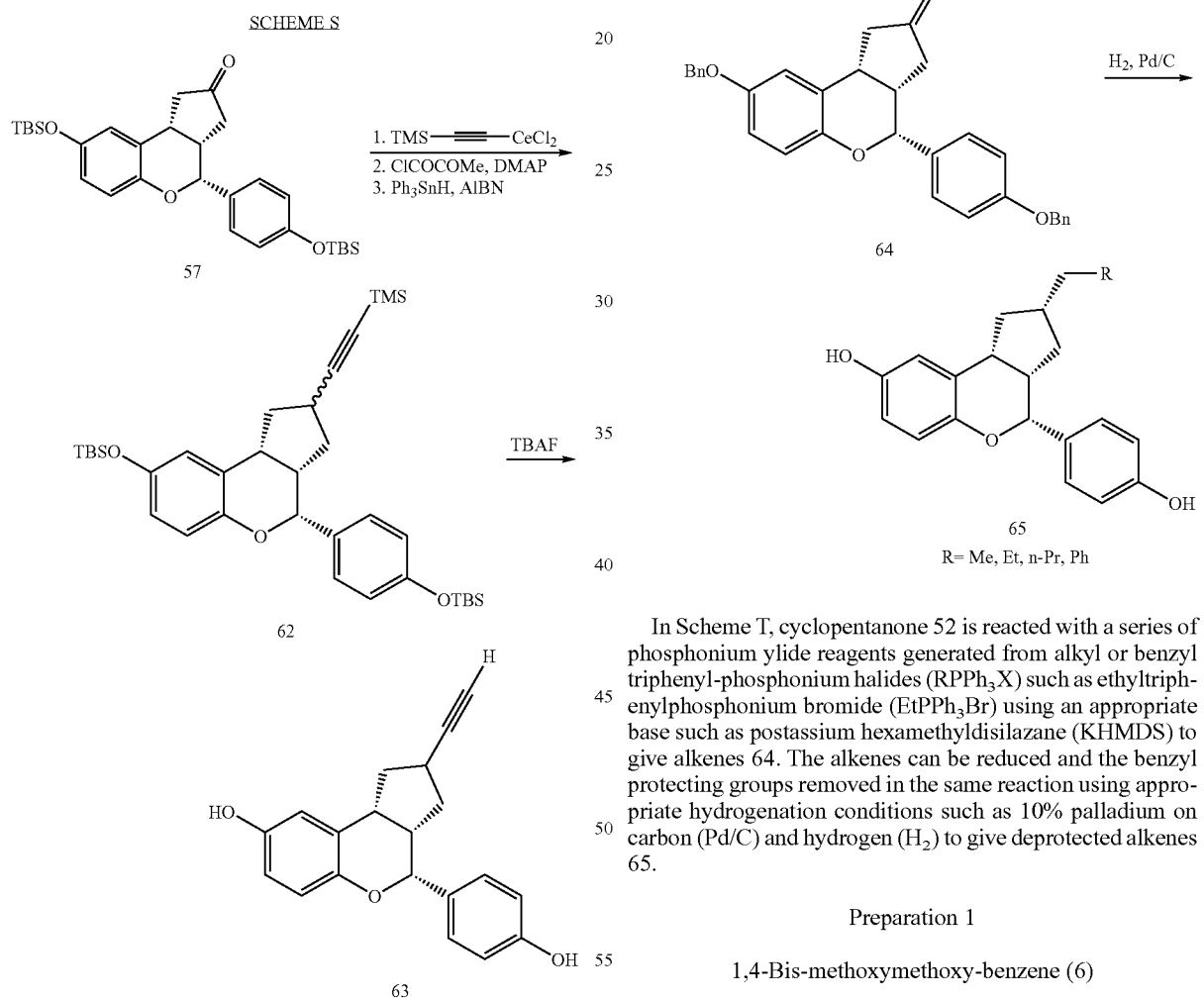

In Scheme T, cyclopentanone 52 is reacted with a series of phosphonium ylide reagents generated from alkyl or benzyl triphenyl-phosphonium halides (RPPh₃X) such as ethyltriphenylphosphonium bromide (EtPPh₃Br) using an appropriate base such as postassium hexamethyldisilazane (KHMDS) to give alkenes 64. The alkenes can be reduced and the benzyl protecting groups removed in the same reaction using appropriate hydrogenation conditions such as 10% palladium on carbon (Pd/C) and hydrogen (H₂) to give deprotected alkenes 65.

Preparation 1

1,4-Bis-methoxymethoxy-benzene (6)

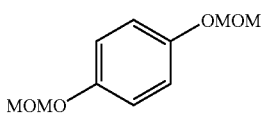

In Scheme S, cyclopentanone 57 is reacted with the organocerium reagent formed by lithiating trimethylsilylacetylene with n-butyllithium followed by reaction with cerium trichloride to give an alcohol. Radical deoxygenation of the alcohol is accomplished via the methyl oxalyl ester (formed using methyl chloroglyoxylate (ClCOCO₂Me), DMAP, and Et₃N), using phenyltin hydride (Ph₃SnH) and 2,2'-Azobisisobutyronitrile (AIBN) as described by Dolan et al. (Dolan, S. C.; MacMillan, J. *J. Chem. Soc., Chem. Commun.* 1985, Stir a suspension of sodium hydride (60% in mineral oil, 3.81 g, 95.45 mmol) in anhydrous DMF (50 mL) under nitrogen atmosphere at 0° C. and add a solution of hydroquinone (5.00 g, 45.45 mmol) in anhydrous DMF (50 mL) dropwise. Add to this suspension methoxymethyl chloride (7.2 mL, 95.45 mmol) dropwise with additional gas evolution noted. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield 1,4-bis-methoxymethoxy-benzene 6 (5.64 g, 63%) as a clear oil. $^1$H NMR (CDCl$_3$): 6.97 (s, 4H), 5.11 (s, 4H), 3.47 (s, 6H).

Preparation 2

2,5-Bis-methoxymethoxy phenylboronic acid (7)

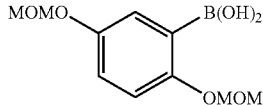

Cool a solution of 1,4-bis-methoxymethoxy-benzene 5 (12.0 g, 60.6 mmol) in dry THF (250 mL) to −78° C. Add s-BuLi (1.3 M in hexane, 51 mL, 66.6 mmol) dropwise. Stir the reaction for 15 minutes and then add triisopropyl borate (14.2 mL, 60.6 mmol) slowly. Stir the reaction at −78° C. for 1 hour and warm to room temperature. Quench the reaction with 10% HCl and stir for 10 minutes. Extract with EtOAc (2×). Dry combined organic extracts (Na$_2$SO$_4$), filter, and concentrate in vacuo. Purify by flash chromatography (250 g SiO$_2$, 20-50% EtOAc/hexanes and then 50% EtOAc/hexanes) to give 2,5-Bis-methoxymethoxy phenylboronic acid 7 (9.73 g, 40.2 mmol, 66%) as a yellow solid. $^1$H NMR (δ, 400 MHz, CDCl$_3$): 7.50 (d, J=2.0 Hz, 1H), 7.09-7.07 (m, 2H), 5.93 (s, 2H), 5.24 (s, 2H), 5.14 (s, 2H), 3.49 (s, 3H), 3.48 (s, 3H). LRMS calcd. for C$_{10}$H$_{14}$BO$_6$: 241.0; found (electrospray, M−1) 241.0.

Preparation 3

(R)-3-Methyl-hexanedioic acid dimethyl ester (1a)

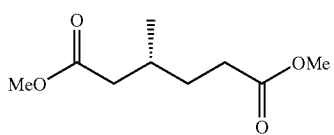

Dissolve (R)-(+)-3-methyladipic acid (5.0 g, 31.2 mmol) in MeOH (317 mL) and add concentrated H$_2$SO$_4$ (17 mL, 312 mmol). Heat the reaction to 60° C. and stir overnight. Cool the reaction to 0° C. and neutralize with aqueous NaOH. Concentrate the mixture to half the volume and dilute with EtOAc. Separate and extract the aqueous solution with EtOAc (2×). Combine the organic solutions and wash with saturated aqueous NaHCO$_3$ and brine. Dry the organic layer (Na$_2$SO$_4$), filter and concentrate in vacuo to yield (R)-3-Methyl-hexanedioic acid dimethyl ester 1a as a colorless liquid (5.53 g, 29.3 mmol, 94%), which is used without further purification. $^1$H NMR (δ, 400 MHz, CDCl$_3$): 3.67 (s, 6H), 2.41-2.27 (m, 3H), 2.16 (dd, J=7.9, 14.9 Hz, 1H), 1.99 (octet, J=6.6 Hz, 1H), 1.75-1.49 (m, 2H), 0.96 (d, J=7.0 Hz, 3H). MS (EI, M-2Me, M—CO$_2$Me): 158, 128.

Preparation 4

(R)-4-Methyl-2-oxo-cyclopentanecarboxylic acid methyl ester (2a)

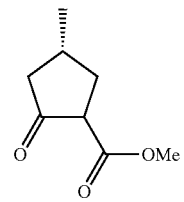

Prepare a solution of NaOMe (3.14 g, 58.3 mmol) in MeOH (9.2 mL). Add toluene (40 mL) and heat to 70° C. Add a solution of (R)-3-methyl-hexanedioic acid dimethyl ester 1a (5.4 g, 29.1 mmol) in toluene (18 mL). Attach a distillation apparatus and continue heating at 75° C. After distillation of methanol is complete, heat the reaction to 110° C. and stir for 2 hrs. Cool the reaction to room temperature, quench with 1.0 N HCl and extract with Et$_2$O (2×). Wash the combined organic extracts with saturated aqueous NaHCO$_3$. Dry the organic solution (MgSO$_4$), filter and concentrate in vacuo. Purify by flash chromatography (silica gel, 0-30% EtOAc/Hexane) to yield a 3:1 mixture of two regioisomers (2.8 g, 24.3 mmol, 84%) as a pale yellow oil with the major isomer being 4-methyl-2-oxo-cyclopentanecarboxylic acid methyl ester 2a. The material was used without further purification in the next preparation. HRMS calcd. 157.0864; found (electrospray, M+1): 157.0864.

Preparation 5

(R)-4-Methyl-2-trifluoromethanesulfonyloxy-cyclopent-1-enecarboxylic acid methyl ester (3a)

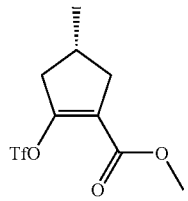

Stir a solution of 4-methyl-2-oxo-cyclopentanecarboxylic acid methyl ester 2a (2.86 g, 17.9 mmol, 3:1 mixture of isomers) in anhydrous dichloromethane (120 mL) cooled to −78° C. and add diisopropylethylamine (12.1 mL, 71.6 mmol) and triflic anhydride (3.4 mL, 19.7 mmol). Stir the reaction for 16 hours, allowing it to warm to room temperature. Quench the reaction with water and wash with 10% citric acid followed by brine. Dry the organic layer over sodium sulfate, filter, and concentrate in vacuo. Purify by flash chromatography (silica gel, 0-30% EtOAc/hexanes then 30% EtOAc/hexanes) to yield 4-Methyl-2-trifluoromethanesulfonyloxy-cyclopent-1-enecarboxylic acid methyl ester 3a (2.62 g, 9.1 mmol, 85%) as the major product which is used without further purification. The yield is based on the amount of the major isomer present in the staring material. $^1$H NMR (δ, 400 MHz, CDCl$_3$): 3.79 (s, 3H), 2.96-2.82 (m, 2H), 2.56-2.44 (m, 1H), 2.41-2.27 (m, 2H), 1.14 (d, 3H, J=7.0 Hz). MS calcd. 288.03; MS (EI, M+) 288.04.

Preparation 6

(S)-2-(2,5-Bis-methoxymethoxy-phenyl)-4-methyl-cyclopent-1-enecarboxylic acid methyl ester (8a)

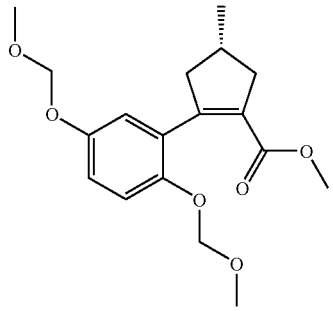

Prepare a mixture of 4-Methyl-2-trifluoromethanesulfonyloxy-cyclopent-1-enecarboxylic acid methyl ester 3a (2.5 g, 8.7 mmol), 2,5-Bis-methoxymethoxy phenylboronic acid 7 (2.31 g, 9.5 mmol), tetrakis(triphenylphosphine)palladium (485 mg, 0.435 mmol), and LiCl (1.1 g, 26.1 mmol) in DME (80 mL). Add 2.0 M solution of Na$_2$CO$_3$ (10 mL, 21.7 mmol) and heat the reaction to reflux and stir for 2 hours. Cool the reaction to room temperature and partitioned between CH$_2$Cl$_2$ and saturated aqueous NaHCO$_3$. Separate and extract the aqueous solution with CH$_2$Cl$_2$ (2×). Combine the organic extracts, dry (Na$_2$SO$_4$), filter and concentrate in vacuo. Purify by flash chromatography (125 g SiO$_2$, 0-30% EtOAc/hexane and 30% EtOAc/hexane) to afford 2-(2,5-Bis-methoxymethoxy-phenyl)-4-methyl-cyclopent-1-enecarboxylic acid methyl ester 8a (2.4 g, 7.1 mmol, 83%) as a yellow oil. $^1$H NMR (δ, 400 MHz, CDCl$_3$): 7.02 (d, 1H, J=9.2 Hz), 6.90 (dd, 1H, J=9.2, 3.1 Hz), 6.80 (d, 1H, J=3.1 Hz), 5.10 (s, 2H), 5.03 (s, 2H), 3.56 (s, 3H), 3.48 (s, 3H), 3.44 (s, 3H), 3.01-2.91 (m, 2H), 2.53-2.37 (m, 3H), 1.14 (d, 3H, J=6.6 Hz). HRMS calcd. 337.1651; found (electrospray, M+1) 337.1647.

Preparation 7

(1S,2R,4S)-2-(2,5-Bis-methoxymethoxy-phenyl)-4-methyl-cyclopentanecarboxylic acid methyl ester

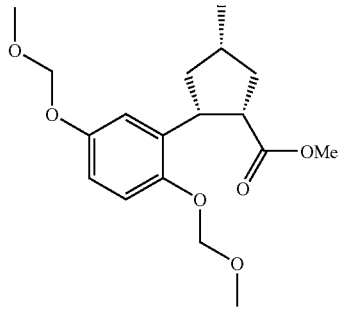

To a suspension of 10% palladium on carbon (0.5 g) in methanol (40 mL) add a solution of 2-(2,5-Bis-methoxymethoxy-phenyl)-4-methyl-cyclopent-1-enecarboxylic acid methyl ester 8a (2.4 g, 7.1 mmol) in methanol (10 mL). Place the mixture under hydrogen (60 psi) at 40° C. for twelve hours. Purge the reaction with nitrogen and filter through celite. Concentrate the filtrate in vacuo to yield 2-(2,5-Bis-methoxymethoxy-phenyl)-4-methyl-cyclopentanecarboxylic acid methyl ester (2.47 g, 7.1 mmol, 100%) as a clear oil. $^1$H NMR (δ, 400 MHz, CDCl$_3$): 6.98 (d, 1H, J=8.8 Hz), 6.85 (d, 1H, J=8.8), 6.81 (dd, 1H, J=3.2, 8.8 Hz), 5.15 (s, 2H), 5.10 (d, 1H, J=6.6 Hz), 5.07 (d, J=6.6 Hz), 3.77-3.67 (m, 1H), 3.51 (s, 3H), 3.46 (s, 3H), 3.38-3.31 (m, 1H), 3.15 (s, 3H), 2.19-2.03 (m, 2H), 1.96-1.68 (m, 3H), 1.19 (d, 3H, J=6.2 Hz). HRMS calcd. 339.1808; found (electrospray, M+1) 339.1818.

Preparation 8

(1S,2R,4S)-2-(2,5-Bis-methoxymethoxy-phenyl)-4-methyl-cyclopentanecarboxylic acid methoxy-methyl-amide (9a)

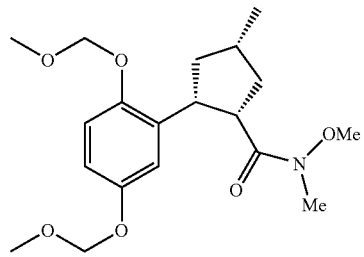

Cool a suspension of 2-(2,5-Bis-methoxymethoxy-phenyl)-4-methyl-cyclopentanecarboxylic acid methyl ester (2.4 g, 7.1 mmol) and N,O-dimethylhydroxylamine hydrochloride (1.4 g, 14.2 mmol) in anhydrous THF (60 mL) to −10° C. in an NaCl/ice bath. Add isopropyl magnesium chloride (2.0 M in THF, 14.2 mL, 28.4 mmol) and stir the reaction for 30 min. Quench the reaction with saturated ammonium chloride. Add EtOAc and wash with brine. Dry the organic solution (Na$_2$SO$_4$), filter and concentrate in vacuo to yield 2-(2,5-Bis-methoxymethoxy-phenyl)-4-methyl-cyclopentanecarboxylic acid methoxy-methyl-amide 9a (2.5 g, 6.8 mmol, 96%) as a pale yellow oil. $^1$H NMR (δ, 400 MHz, CDCl$_3$): 6.95 (d, 1H, J=8.8 Hz), 6.92 (d, 1H, J=3.0 Hz), 6.79 (dd, 1H, J=8.8, 3.0 Hz), 5.16-5.03 (m, 4H), 3.80 (m, 1H), 3.64 (m, 1H), 3.50 (s, 3H), 3.46 (s, 3H), 3.43 (s, 3H), 2.74 (s, 3H), 2.13-2.05 (m, 2H), 1.95-1.79 (m, 3H), 1.19 (d, 3H, J=6.2 Hz). HRMS calcd. 368.2073; found (electrospray, M+1) 368.2065.

Preparation 9

(1S,2R,4S)-[2-(2,5-Bis-methoxymethoxy-phenyl)-4-methyl-cyclopentyl]-(4-methoxymethoxy-phenyl)-methanone (10a)

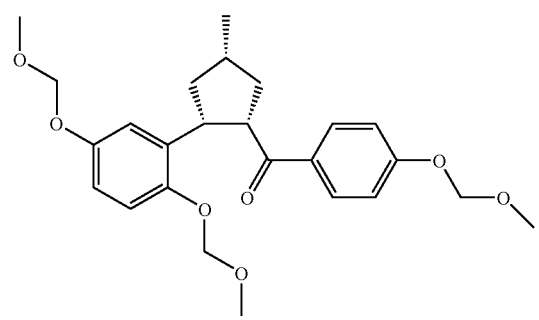

Cool a solution of 1-bromo-4-methoxymethoxy benzene (2.8 g, 13.0 mmol) in 100 mL of THF to −78° C. Add s-BuLi (20 mL of a 1.3 M solution in hexane, 26 mmol) drop wise. Stir the reaction for 20 min and then transfer via cannula to a solution of 2-(2,5-Bis-methoxymethoxy-phenyl)-4-methyl-cyclopentanecarboxylic acid methoxy-methyl-amide 9a (2.4 g, 6.5 mmol) in anhydrous THF (50 mL) at 0° C. Stir the solution for 30 minutes at 0° C. Quench the reaction with saturated ammonium chloride. Add EtOAc and wash with brine. Dry the organic solution (Na$_2$SO$_4$), filter, and concentrate in vacuo. Purify by flash chromatography (silica gel, 0-30% EtOAc/hexanes and 30% ethyl acetate/hexane) to yield [2-(2,5-Bis-methoxymethoxy-phenyl)-4-methyl-cyclopentyl]-(4-methoxymethoxy-phenyl)-methanone 10a (2.7 g, 93%) as a pale yellow oil. $^1$H NMR (δ, 400 MHz, CDCl$_3$): 7.58 (d, 2H, J=8.8 Hz), 6.83 (d, 2H, J=8.8 Hz), 6.76 (d, 1H, J=2.9 Hz), 6.65 (d, 1H, J=8.8 Hz), 6.58 (dd, 1H, J=9.0, 2.9 Hz), 5.16 (d, 1H, J=6.8 Hz), 5.14 (d, 1H, J=6.8 Hz), 5.04 (d, 1H, J=6.8 Hz), 5.00 (d, 1H, J=6.8 Hz), 4.93 (d, 1H, J=6.8 Hz), 4.89 (d, 1H, J=6.8 Hz), 4.35-4.27 (m, 1H), 3.92-3.82 (m, 1H), 3.44 (s, 3H), 3.43 (s, 3H), 3.42 (s, 3H), 2.22-2.10 (m, 2H), 2.05-1.94 (m, 1H), 1.92-1.76 (m, 2H), 1.22 (d, 3H, J=6.2 Hz). HRMS calcd. 445.2226; found (electrospray, M+1) 445.2223.

Example 1

Preparation of (2S,3aS,4R,9bR)-4-(4-Hydroxy-phenyl)-2-methyl-1,2,3,3a,4,9b-hexahydro-cyclopenta[c]chromen-8-ol

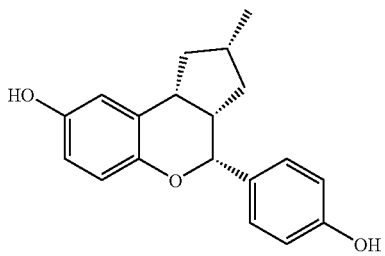

(2S,3aS,4R,9bR)-4-(4-Hydroxy-phenyl)-2-methyl-1, 2,3,3a,4,9b-hexahydro-cyclopenta [c]chromen-8-ol
(11a)

To a solution of [2-(2,5-bis-methoxymethoxy-phenyl)-4-methyl-cyclopentyl]-(4-methoxymethoxy-phenyl)-methanone 10a (2.6 g, 5.8 mmol) in anhydrous methanol (232 mL) add p-toluenesulfonic acid (1.1 g, 5.8 mmol) and heat the resulting solution to 50° C. for 18 hours under nitrogen. Cool the reaction to ambient temperature and add bromocreosol green (10 mg) and sodium cyanoborohydride (1.82 g, 29.0 mmol). Add methanol saturated with HCl (gas) drop wise until yellow color is maintained. Stir the reaction one hour past the time when no more color change is observed. Quench the reaction with saturated sodium bicarbonate, add EtOAc, and wash the organic solution with sodium bicarbonate and brine. Dry the organic solution over sodium sulfate, concentrate in vacuo, and purify by flash chromatography (silica gel, 0-40% EtOAc/hexanes and 40% ethyl acetate/hexanes) to give 4-(4-Hydroxy-phenyl)-2-methyl-1,2,3,3a,4,9b-hexahydro-cyclopenta[c]chromen-8-ol 11a (1.2 g, 4.0 mmol, 70%). $^1$H NMR (δ, 400 MHz, MeOD) 7.23 (d, 2H, J=8.4 Hz), 6.77 (d, 2H, J=8.4 Hz), 6.68 (d, 1H, J=8.8 Hz), 6.54 (d, 1H, J=2.6 Hz), 6.50 (dd, 1H, J=8.6, 2.9 Hz), 3.45-3.38 (m, 1H), 2.63-2.55 (m, 1H), 2.52-2.43 (m, 1H), 1.96-1.84 (m, 1H), 1.41-1.32 (m, 1H), 1.23-1.07 (m, 2H), 0.87 (d, 3H, J=6.6 Hz). MS calcd. 295.1; found (electrospray, M−1) 295.1. HPLC (Zorbax C18 column; 10 to 100% CH$_3$CN/H$_2$O for 10 min then 100% CH$_3$CN for 5 min; 1 mL/min; t$_r$ 10.35 min). HPLC (Chiralpak AD, 20-80% IPA/Heptane for 20 min; 1 mL/min; t$_R$=4.37 min).

Example 2

Preparation of (2R,3aR,4S,9bS)-4-(4-Hydroxy-phenyl)-2-methyl-1,2,3,3a,4,9b-hexahydro-cyclopenta[c]chromen-8-ol

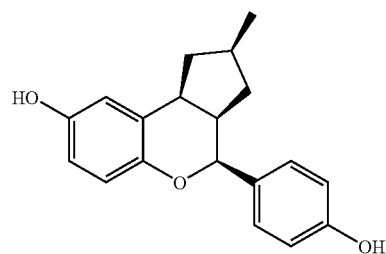

(2R,3aR,4S,9bS)-4-(4-Hydroxy-phenyl)-2-methyl-1, 2,3,3a,4,9b-hexahydro-cyclopenta [c]chromen-8-ol
(11a)

The enantiomer of example 1 was prepared in a manner substantially similar to example 1 except the starting adipic acid 1a was racemic 3-methyladipic acid. The two enantiomers were separated by chiral preparative HPLC (Chiralpak AD, IPA/Heptane). $^1$H NMR (δ, 400 MHz, MeOD) 7.23 (d, 2H, J=8.4 Hz), 6.77 (d, 2H, J=8.4 Hz), 6.68 (d, 1H, J=8.8 Hz), 6.54 (d, 1H, J=2.6 Hz), 6.50 (dd, 1H, J=8.6, 2.9 Hz), 3.45-3.38 (m, 1H), 2.63-2.55 (m, 1H), 2.52-2.43 (m, 1H), 1.96-1.84 (m, 1H), 1.41-1.32 (m, 1H), 1.23-1.07 (m, 2H), 0.87 (d, 3H, J=6.6 Hz). MS calcd. 295.1; found (electrospray, M−1) 295.1. HPLC (Zorbax C18 column; 10 to 100% CH$_3$CN/H$_2$O for 10 min then 100% CH$_3$CN for 5 min; 1 mL/min; t$_r$ 10.35 min). HPLC (Chiralpak AD, 20-80% IPA/Heptane for 20 min; 1 mL/min; t$_R$=9.4 min).

Example 3

Preparation of (2R,3aR,4S,9bS)- and (2S,3aS,4R, 9bR)-2-tert-Butyl-4-(4-hydroxy-phenyl)-1,2,3,3a,4, 9b-hexahydro-cyclopenta[c]chromen-8-ol

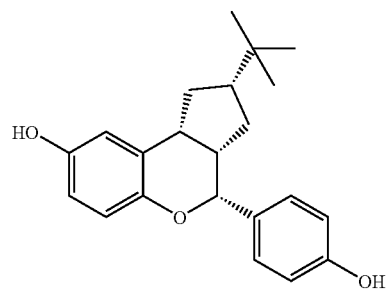

(2R,3aR,4S,9bS)- and (2S,3aS,4R,9bR)-2-tert-Butyl-4-(4-hydroxy-phenyl)-1,2,3,3a,4,9b-hexahydro-cyclopenta[c]chromen-8-ol (11b)

Example 3 was prepared in a manner substantially similar to example 1 except the starting adipic acid 1b was racemic 3-t-butyl adipic acid. The two enantiomers were separated by chiral preparative HPLC (Chiralpak AD, IPA/Heptane).

Enantiomer A: $^1$H NMR (δ, 400 MHz, MeOD): 7.24 (d, 2H, J=8.8 Hz), 6.78 (d, 2H, J=8.4 Hz), 6.67 (d, 1H, J=8.8 Hz), 6.56 (d, 1H, J=2.7 Hz), 6.50 (dd, 1H, J=8.6, 2.7 Hz), 4.88 (1H, obscured by MeOD), 3.46-3.37 (m, 1H), 2.58-2.48 (m, 1H), 2.38-2.27 (m, 1H), 1.80-1.66 (m, 1H), 1.40-1.11 (m, 3H), 0.71 (s, 9H). HPLC (Chiralpak AD, 20-80% IPA/Heptane for 15 min; 1 mL/min; $t_R$=3.13 min). HPLC (Zorbax C18 column; 10 to 100% $CH_3CN/H_2O$ for 10 min then 100% $CH_3CN$ for 5 min; 1 mL/min; $t_r$ 11.31 min).

Enantiomer B: $^1$H NMR (δ, 400 MHz, MeOD): 7.24 (d, 2H, J=8.8 Hz), 6.78 (d, 2H, J=8.4 Hz), 6.67 (d, 1H, J=8.8 Hz), 6.56 (d, 1H, J=2.7 Hz), 6.50 (dd, 1H, J=8.6, 2.7 Hz), 4.88 (1H, obscured by MeOD), 3.46-3.37 (m, 1H), 2.58-2.48 (m, 1H), 2.38-2.27 (m, 1H), 1.80-1.66 (m, 1H), 1.40-1.11 (m, 3H), 0.71 (s, 9H). HPLC (Chiralpak AD, 20-80% IPA/Heptane for 15 min; 1 mL/min; $t_R$=5.60 min). HPLC (Zorbax C18 column; 10 to 100% $CH_3CN/H_2O$ for 10 min then 100% $CH_3CN$ for 5 min; 1 mL/min; $t_r$ 11.31 min).

Preparation 10

4-Oxo-tetrahydro-furan-3-carboxylic acid methyl ester (4a)

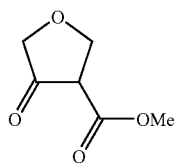

To a suspension of NaH (6.66 g, 166.5 mmol) in ether (500 mL) add methyl glycolate (15.0 g, 166.5 mmol) drop wise. Stir the reaction until evolution of $H_2$ gas ceases. Concentrate and dissolve the solid in DMSO (300 mL). Cool the reaction to 0° C. and add methyl acrylate (16.6 mL, 183.17 mmol) drop wise. Warm the reaction to room temperature and stir overnight. Acidify the reaction with 10% HCl and extract with ether (3×). Combine organic extracts and wash with brine. Dry the organic solution ($Na_2SO_4$), filter, and concentrate in vacuo. Purify by flash chromatography (250 g $SiO_2$, 40 mL/min, 0-50% ethyl acetate/hexane for 20 minutes and then 50% ethyl acetate/hexane for 13 minutes) to yield 4-oxo-tetrahydro-furan-3-carboxylic acid methyl ester 4a (12.9 g, 89.2 mmol, 54%) as a colorless oil. $^1$H NMR (δ, 400 MHz, $CDCl_3$): 4.50 (dd, 1H, J=8.4, 9.6 Hz), 4.46 (dd, 1H, J=8.4, 9.6 Hz), 4.05 (d, 1H, J=16.8 Hz), 3.79, (s, 3H), 3.97 (d, 1H, J=16.8, Hz), 3.54 (t, 1H, J=8.4 Hz). MS calcd. 144; found (EI) 144.

Example 4

Preparation of (3aS,4S,9bS)- and (3aR,4R,9bR)-4-(4-Hydroxy-phenyl)-1,3a,4,9b-tetrahydro-3H-2,5-dioxa-cyclopenta[a]naphthalen-8-ol

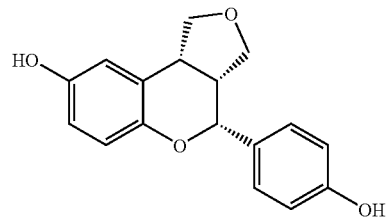

(3aS,4S,9bS)- and (3aR,4R,9bR)-4-(4-Hydroxy-phenyl)-1,3a,4,9b-tetrahydro-3H-2,5-dioxa-cyclopenta[a]naphthalen-8-ol (11c)

Example 4 was prepared in a manner substantially similar to example 1 except 4-oxo-tetrahydro-furan-3-carboxylic acid methyl ester 4a was used to make the enol triflate 3c. The two enantiomers were separated by chiral preparative HPLC (Chiralpak AD, MeOH).

Enantiomer A: $^1$H NMR (δ, 400 MHz, MeOD): 7.27 (d, 2H, J=8.8 Hz), 6.79 (d, 2H, J=8.4 Hz), 6.75 (d, 1H, J=8.8 Hz), 6.63-6.57 (m, 2H), 5.03 (d, 1H, J=2.4 Hz), 4.14 (dd, 1H, J=8.6, 5.9 Hz), 3.81-3.75 (m, 2H), 3.68-3.58 (m, 2H), 3.12 (dq, 1H, J=2.4, 8.8 Hz). HRMS (EI+) calcd 284.1049; found: 284.1027. HPLC (Chiralpak AD, 20-80% IPA/Heptane for 20 min; 1 mL/min; $t_R$=10.33 min). HPLC (Zorbax C18 column; 10 to 100% $CH_3CN/H_2O$ for 10 min then 100% $CH_3CN$ for 5 min; 1 mL/min; $t_r$ 8.29 min).

Enantiomer B: $^1$H NMR (δ, 400 MHz, MeOD): 7.27 (d, 2H, J=8.8 Hz), 6.79 (d, 2H, J=8.4 Hz), 6.75 (d, 1H, J=8.8 Hz), 6.63-6.57 (m, 2H), 5.03 (d, 1H, J=2.4 Hz), 4.14 (dd, 1H, J=8.6, 5.9 Hz), 3.81-3.75 (m, 2H), 3.68-3.58 (m, 2H), 3.12 (dq, 1H, J=2.4, 8.8 Hz). HRMS (EI+) calcd 284.1049; found: 284.1088. HPLC (Chiralpak AD, 20-80% IPA/Heptane for 20 min; 1 mL/min; $t_R$=13.31 min). HPLC (Zorbax C18 column; 10 to 100% $CH_3CN/H_2$ for 10 min then 100% $CH_3CN$ for 5 min; 1 mL/min; $t_r$ 8.29 min).

Preparation 11

4-Oxo-tetrahydro-thiophene-3-carboxylic acid methyl ester (4b)

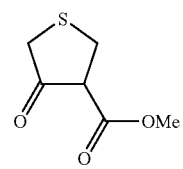

To a solution of methyl thioglycolate (16.0 g, 0.15 mol) in MeOH (400 mL) add NaOMe (8.04 g, 0.149 mol). Stir the reaction mixture at room temperature for 3 hours. Concentrate and dissolve the solid in DMSO (130 mL). Cool the solution to 0° C. and add methyl acrylate (15.5 mL, 0.17 mol) drop wise. Warm the reaction to room temperature and stir overnight (18 hours). Acidify with 10% HCl and extract with Et₂O (3×). Wash the combine organic extracts with brine, dry (Na₂SO₄), filter and concentrate in vacuo. Purify by flash chromatography (250 g SiO₂, 40 mL/min, 0-30% EtOAc/Hexane for 15 minutes and then 30% EtOAc/Hexane for 13 minutes) to afford a 1:1.5 mixture of two regioisomers (6.77 g, 48%) as a pale yellow oil with the major isomer being 4-oxo-tetrahydro-thiophene-3-carboxylic acid methyl ester 4b as a yellow oil. The material was used without further purification. MS calcd. 160; found (EI) 160.

Example 5

Preparation of (3aR,4S,9bS)- and (3aS,4R,9bR)-4-(4-Hydroxy-phenyl)-1,3a,4,9b-tetrahydro-3H-5-oxa-2-thia-cyclopenta[a]naphthalen-8-ol

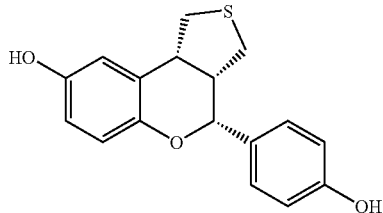

(3aR,4S,9bS)- and (3aS,4R,9bR)-4-(4-Hydroxy-phenyl)-1,3a,4,9b-tetrahydro-3H-5-oxa-2-thia-cyclopenta[a]naphthalen-8-ol (11d)

Example 5 was prepared in a manner substantially similar to example 1 except 4-oxo-tetrahydro-thiophene-3-carboxylic acid methyl ester 4b was used to make the enol triflate 3d. The two enantiomers were separated by chiral preparative HPLC (Chiralpak AD, IPA/Heptane).

Enantiomer A: ¹H NMR (δ, 400 MHz, MeOD) 7.32 (d, 2H, J=8.3 Hz), 6.76 (d, 2H, J=8.3 Hz), 6.72 (d, 1H, J=8.4 Hz), 6.66 (d, 1H, J=3.1 Hz), 6.59 (dd, 1H, J=8.4, 3.1 Hz), 5.12 (s, 1H), 4.14 (dd, 1H, J=6.4, 1.5 Hz), 3.88 (dd, 1H, J=5.4, 5.4 Hz), 2.64 (dd, 1H, J=10.1, 6.6 Hz), 2.55 (dd, 1H, J=12.3, 4.8 Hz), 2.47-2.38 (m, 1H), 2.29-2.18 (m, 1H). HPLC (Zorbax C18 column; 10 to 100% CH₃CN/H₂O for 10 min then 100% CH₃CN for 5 min; 1 mL/min; t_r 9.02 min). HPLC (Chiralpak AD, 30-70% IPA/Heptane for 10 min; 1 mL/min; t_R=7.49 min). HRMS calcd for C₁₇H₁₇O₃S: 301.0898; found (ES+): 301.0897 (M+H).

Enantiomer B: ¹H NMR (δ, 400 MHz, MeOD) 7.32 (d, 2H, J=8.3 Hz), 6.76 (d, 2H, J=8.8 Hz), 6.72 (d, 1H, J=8.6 Hz), 6.66 (d, 1H, J=2.9 Hz), 6.59 (dd, 1H, J=8.6, 2.9 Hz), 5.12 (s, 1H), 4.14 (dd, 1H, J=6.2, 1.5 Hz), 3.87 (dd, 1H, J=5.4, 5.4 Hz), 2.64 (dd, 1H, J=10.1, 6.6 Hz), 2.55 (dd, 1H, J=12.3, 4.8 Hz), 2.48-2.39 (m, 1H), 2.30-2.20 (m, 1H). HPLC (Zorbax C18 column; 10 to 100% CH₃CN/H₂O for 10 min then 100% CH₃CN for 5 min; 1 mL/min; t_r 9.02 min). HPLC (Chiralpak AD, 30-70% IPA/Heptane for 10 min; 1 mL/min; t_R=8.9 min). HRMS calcd for C₁₇H₁₆O₃S: 300.0820; found (EI): 300.0789.

Example 6

Preparation of (2S,3aR,4S,9bS)- or (2R,3aS,4R,9bR)-4-(4-Hydroxy-phenyl)-2-oxo-1,2,3,3a,4,9b-hexahydro-5-oxa-2λ⁴-thia-cyclopenta[a]naphthalen-8-ol

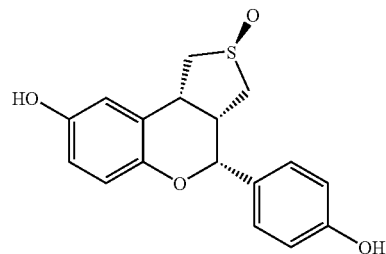

(2S,3aR,4S,9bS)- or (2R,3aS,4R,9bR)-4-(4-Hydroxy-phenyl)-2-oxo-1,2,3,3a,4,9b-hexahydro-5-oxa-2λ⁴-thia-cyclopenta[a]naphthalen-8-ol (13)

To a solution of enantiomer A of 4-(4-hydroxy-phenyl)-1,3a,4,9b-tetrahydro-3H-5-oxa-2-thia-cyclopenta[a]naphthalen-8-ol 11d (20 mg, 0.066 mmol) in MeOH/H₂O (1:1, 3 mL) add oxone (40 mg, 0.066 mmol). Stir the reaction at room temperature for 30 minutes. Add 1.0 M Na₂SO₃ and stir the reaction for 5 minutes. Dilute with EtOAc and wash with saturated sodium bicarbonate. Extract aqueous layer with EtOAc (2×). Combine organic extracts, dry (Na₂SO₄), filter and concentrate to afford 4-(4-hydroxy-phenyl)-2-oxo-1,2,3,3a,4,9b-hexahydro-5-oxa-2λ⁴-thia-cyclopenta[a]naphthalen-8-ol 13 (17 mg, 0.054 mmol, 85%). ¹H NMR (δ, 400 MHz, MeOD) 7.44 (d, 2H, J=8.8 Hz), 6.85 (d, 2H, J=8.8 Hz), 6.75 (d, 1H, J=8.8 Hz), 6.70 (d, 1H, J=2.8 Hz), 6.61 (dd, 1H, J=8.8, 2.8 Hz), 5.19 (s, 1H), 4.19 (dd, 1H, J=6.2, 6.2 Hz), 3.76 (d, 1H, J=7.9 Hz), 3.06-2.94 (m, 1H), 2.84 (dd, 1H, J=14.1, 5.3 Hz), 2.62 (dd, 1H, J=13.0, 5.5 Hz), 2.29 (dt, 1H, J=5.2, 14.0 Hz). HPLC (Zorbax C18 column; 10 to 100% CH₃CN/H₂O for 10 min then 100% CH₃CN for 5 min; 1 mL/min; t_r 7.17 min). LRMS calcd for C₁₇H₁₅O₄S: 315.1; found (ES−, M−H): 315.2.

Example 7

Preparation of (3aR,4S,9bS)- or (3aS,4R,9bR)-4-(4-Hydroxy-phenyl)-2,2-dioxo-1,2,3,3a,4,9b-hexahydro-5-oxa-2,6-thia-cyclopenta[a]naphthalen-8-ol

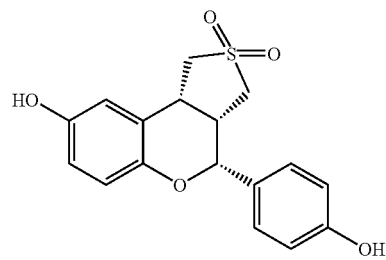

(3aR,4S,9bS)- or (3aS,4R,9bR)-4-(4-Hydroxy-phenyl)-2,2-dioxo-1,2,3,3a,4,9b-hexahydro-5-oxa-2λ⁶-thia-cyclopenta[a]naphthalen-8-ol (14)

To a solution of enantiomer A of 4-(4-hydroxy-phenyl)-1,3a,4,9b-tetrahydro-3H-5-oxa-2-thia-cyclopenta[a]naphthalen-8-ol 11d (10 mg, 0.033 mmol) in MeOH/H$_2$O (1:1, 3 mL) add oxone (40 mg, 0.066 mmol). Stir the reaction at 50° C. for 2 hours. Add 1.0 M Na$_2$SO$_3$ and stir the reaction for 5 minutes. Dilute with EtOAc and wash with saturated sodium bicarbonate. Extract aqueous layer with EtOAc (2×). Combine organic extracts, dry (Na$_2$SO$_4$), filter and concentrate to afford 4-(4-Hydroxy-phenyl)-2,2-dioxo-1,2,3,3a,4,9b-hexahydro-5-oxa-2λ⁶-thia-cyclopenta[a]naphthalen-8-ol 14 (8.5 mg, 0.025 mmol, 77%). $^1$H NMR (δ, 400 MHz, MeOD) 7.47 (d, 2H, J=8.3 Hz), 6.87-6.74 (m, 4H), 6.67 (dd, 1H, J=8.6, 2.4 Hz), 5.25 (s, 1H), 4.12-4.01 (m, 2H), 3.00 (m, 1H), 2.72 (dt, 1H, J=6.8, 12.8 Hz), 2.63-2.53 (m, 1H), 2.52-2.42 (m, 1H). HPLC (Zorbax C18 column; 10 to 100% CH$_3$CN/H$_2$O for 10 min then 100% CH$_3$CN for 5 min; 1 mL/min; t$_r$ 7.68 min).

Preparation 12

6-methoxymethoxy coumarin (17a)

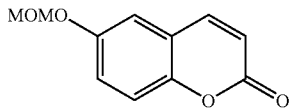

Equip a 3-L, three-neck, round-bottom flask equipped with a large blade mechanical stirrer, a thermocouple, a Claisen adapter, an addition funnel, and a reflux condenser. Add 2,5-dimethoxycinnamic acid (102.8 g, 493 mmol, 1.0 equiv) and dichloroethane (1.5 L). Add boron tribromide (247.4 g, 987 mmol, 2.0 equiv) dropwise over 45 min while keeping the temperature below 40° C. Rapidly stir the resulting mixture and heat gradually to 83° C. over 45 min, monitoring the temperature increase and gas evolution. Stir for 6 h at reflux then for 15 h at 76° C. Cool the resulting mixture to room temperature and quenched carefully with water (450 mL). Filter the solid, wash with heptane and dry under vacuum to afford 6-hydroxy coumarin (95 g) as a light brown solid which is used without further purification. Equip a 2-L, three-neck, round-bottom flask with a magnetic stir bar and a thermocouple. Add 6-hydroxy coumarin (39.8 g, 245 mmol, 1.0 equiv), anhydrous acetonitrile (700 mL) and N,N-diisopropylethylamine (200 mL, 1.15 mol, 4.7 equiv). Add chloromethyl methyl ether (40.0 mL, 527 mmol, 2.1 equiv) dropwise over 30 min while keeping the temperature below 40° C. Stir the resulting mixture at room temperature for 3 h, then add an additional equiv of chloromethyl methyl ether. Stir at room temperature for 15 h, then quench the reaction mixture with saturated aqueous ammonium chloride (500 mL) and extracted with ethyl acetate. Combine the organic extracts and dry over anhydrous magnesium sulfate, filter and concentrate under reduced pressure. Purify the residue by column chromatography on silica gel (30-50% ethyl acetate/heptane) to afford a light yellow solid. Suspend the solid in a mixture of ethyl acetate/heptane (150 mL, 10:90), filter and dry to afford 6-methoxymethoxy coumarin 17a (25.6 g, 50%) as a white solid: $^1$H NMR (300 MHz, CDCl$_3$) δ 7.70 (d, J=7.8 Hz, 1H), 7.30-7.12 (m, 3H), 6.41 (d, J=7.8 Hz, 1H), 5.20 (s, 2H), 3.48 (s, 3H); $^{13}$C NMR (75 MHz, CDCl$_3$) δ 161.2, 154.0, 149.5, 143.5, 121.6, 119.6, 118.1, 117.3, 113.8, 95.3, 56.4; IR (KBr) 1714 (s), 1570 (s), 1491 (m), 1447 (m), 1266 (s), 1154 (s), 1070 (s), 1017 (s) cm$^{-1}$; ESI MS m/z 207 [C$_{11}$H$_{10}$O$_4$+H]$^+$.

Preparation 13

8-Methoxymethoxy-2-methylene-2,3,3a,9b-tetrahydro-1H-cyclopenta[c]chromen-4-one (18)

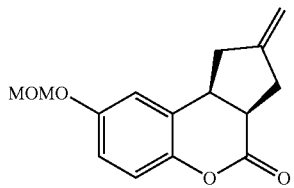

To a solution of 6-methoxymethoxy coumarin 17a (21 g, 0.102 mol) and Pd(OAc)$_2$ (2.75 g, 0.012 mol) in 500 mL THF add 2-(acetoxymethyl)allyl-trimethylsilane (26 mL, 0.122 mol) followed by triisopropyl phosphite (18.1 mL, 0.073 mol). After stirring at 60° C. overnight, cool the solution to RT, concentrate under reduced pressure, and dilute with EtOAc. Wash the solution with saturated aqueous sodium bicarbonate and brine. Dry over Na$_2$SO$_4$, and then concentrate to an oil. Purify the material by silica gel chromatography (Biotage 40M+65M columns, 10 to 30% EtOAc/Hex over 60 min at 50 mL/min followed by 30 to 50% EtOAc/Hex over 60 min at 50 mL/min) to give 18.3 g (0.070 mol, 69%) of cyclopentanoid 18 and 3.8 g (18.3 mmol, 18%) of recovered starting material. HRMS (ES+) calc for C$_{15}$H$_{17}$O$_4$: 261.1127, found: 261.1122 (M+1).

Preparation 14

8-Methoxymethoxy-2,3,3a,9b-tetrahydro-1H-spiro[cyclopenta[c]chromen-2,4'-[1,3]dioxlan-4-one](19)

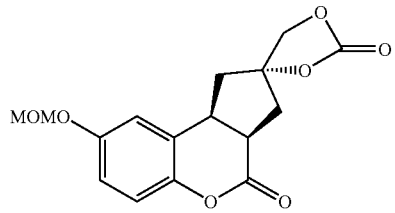

To a solution of cyclopentanoid 18 (17.7 g, 68 mmol) and N-methylmorpholine N-oxide (15.5 g, 132 mmol) in 375 mL t-butanol, 75 mL of THF, and 45 mL of water add osmium tetroxide (39 mL of a 2.5 wt % solution in t-butanol, 3.1 mmol). After stirring for 2 hrs, add a solution of 125 mL of saturated aqueous Na$_2$SO$_3$ and 125 mL of saturated aqueous sodium bicarbonate. After stirring for 1 hr, separate the aqueous solution and extract it 2× with EtOAc. Combine the organic solutions and dilute with 300 mL EtOAc. Wash the organic solution with 1:1 water:brine, brine, dry over Na$_2$SO$_4$, filter, and concentrate to a white solid. To a suspension of the solid in 680 mL of CH$_2$Cl$_2$ and Et$_3$N (38 mL, 273 mmol) cooled to 0° C. add phosgene (70 mL, 132 mmol). After stirring 4 hrs, quench the reaction with saturated aqueous sodium bicarbonate. Wash the organic solution with 1 M HCl, saturated aqueous sodium bicarbonate, brine, dry over $Na_2SO_4$, filter and concentrate to a white solid. Dissolve the solid in 50 mL of $CH_2Cl_2$ and then add 50 mL hexanes. After stirring for 30 min collect the precipitate by filtration to give 10.3 g of cyclic carbonate 19. Concentrate the mother liquor and purify by silica gel chromatography (Biotage 40L column, 0 to 100% EtOAc/1:1 $CH_2Cl_2$:Hex over 60 min at 50 mL/min) to give another 3.23 g of cyclic carbonate 19 and 5.5 g of the minor diastereomer. HRMS (ES+) calc for $C_{16}H_{17}O_7$: 321.0974, found: 321.0966 (M+H).

Preparation 15

Trifluoro-methanesulfonic acid 8-methoxymethoxy-1,2,3,9b-tetrahydro-spiro[cyclopenta[c]chromen-2,4'-[1,3]dioxlan-4-yl]ester (20)

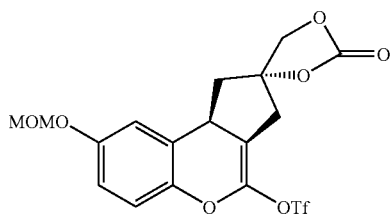

To a solution cyclic carbonate 19 (3.0 g, 9.37 mmol) in 70 mL of THF at −78° C. was added LiHMDS (13.1 mL of a 1M solution in hexanes, 13.1 mmol). After stirring for 30 min a solution of N-phenyltrifluoromethanesulfonimide (4.68 g, 13.1 mmol) and HMPA (4.56 mL, 26.2 mmol) in 10 mL THF was added via cannula. The solution was warmed to 0° C. and after stirring for 30 min, saturated aqueous ammonium chloride was added. The solution was diluted with EtOAc, washed with water, brine, dried over $Na_2SO_4$, filtered, and concentrated. Purification by silica gel chromatography (Biotage 40M column, 0 to 30% EtOAc/1:1 $CH_2Cl_2$:Hexanes over 60 min at 50 mL/min) gave 2.5 g (5.53 mmol, 59%) of enol triflate 20. $^1$H NMR (δ, 400 MHz, $CDCl_3$): δ 6.96-6.90 (m, 2H), 6.76 (m, 1H), 5.13 (s, 2H), 4.46 (d, 1H, J=8.8 Hz), 4.40 (d, 1H, J=9.2 Hz), 4.23 (m, 1H), 3.47 (s, 3H), 3.12 (m, 1H), 2.96-2.87 (m, 2H), 1.98 (t, 1H, J=12.3 Hz).

Preparation 16

8-Methoxymethoxy-4-(4-methoxymethoxy-phenyl)-1,2,3,9b-tetrahydro-spiro[cyclopenta[c]chromene-2,4'-[1,3]dioxian](21)

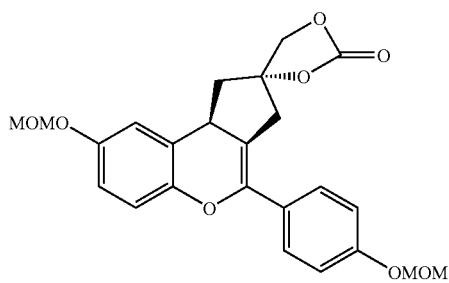

To a solution of p-bromophenyl methoxymethyl ether (1.35 g, 6.22 mmol) in 28 mL of THF at −78° C. was added tBuLi (7.33 mL of a 1.7 M solution in pentane, 12.46 mmol). After stirring for 10 min the solution was warmed to 0° C. and a solution of $ZnCl_2$ (6.23 mL of a 1 M solution in ether, 6.23 mmol) was added. The cold bath was removed and after stirring for 10 min the solution was transferred to a solution of enol triflate 20 (1.88 g, 4.16 mmol), $Pd(PPh_3)_4$ (720 mg, 0.623 mmol) in 7 mL of THF. The solution was warmed to 50° C. After stirring for 4 hrs, the solution was cooled to room temperature, diluted with EtOAc, washed with saturated aqueous bicarbonate, brine, dried over $Na_2SO_4$, filtered, and concentrated. The material was absorbed to 10 g of silica gel and purified by silica gel chromatography (Biotage 40M column, 0 to 40% EtOAc/Hexanes over 60 min at 50 mL/min) to give 1.06 g (2.41 mmol, 58%) of flavene 21. $^1$H NMR (300 MHz, $CDCl_3$) δ 7.48 (m, 2H), 7.07 (m, 2H), 7.03 (d, 1H, J=8.8 Hz), 6.92 (dd, 1H, J=8.8, 3.0 Hz), 6.79 (d, 1H, J=3.0 Hz), 5.21 (s, 2H), 5.14 (s, 2H), 4.35 (d, 1H, J=8.8 Hz), 4.32 (d, 1H, J=8.8 Hz), 4.16 (m, 1H), 3.50 (s, 6H), 3.36 (dt, 1H, J=9.8, 6.0 Hz), 3.36 (m, 1H), 2.93-2.85 (m, 2H), 1.92 (dd, 1H, J=13.2, 11.0 Hz).

Preparation 17

8-Methoxymethoxy-4-(4-methoxymethoxy-phenyl)-1,2,3,3a,4,9b-hexahydro-spiro[cyclopenta[c]chromene-2,4'-[1,3]dioxian](22)

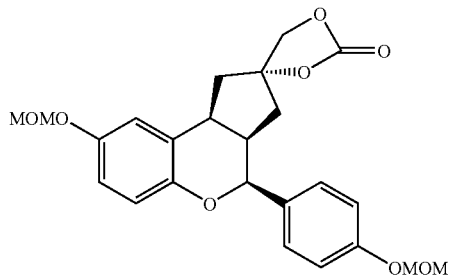

A solution of flavene 21 (1.06 g, 2.41 mmol) and 300 mg Pd/C in 8 mL of THF and 25 mL of MeOH was stirred under 60 psi $H_2$ for 2 hrs. Another 200 mg of Pd/C and 4 mL of THF were added. After stirring for 2 hrs, the solution was filtered through celite and the filter cake washed with MeOH/EtOAc. The combined organic filtrates were concentrated. The material was adsorbed to 10 g silica gel and purified by silica gel chromatography (Biotage 40M column, 0 to 50% EtOAc/Hexanes over 45 min at 50 mL/min). Mixed fractions were re-purified (Biotage 40S column, same conditions) to give 886 mg (2.0 mmol, 83%) of flavan 22. HRMS (ES+) calc for $C_{24}H_{30}NO_8$: 460.1971, found: 460.1975 (M+$NH_4$).

Preparation 18

8-Methoxymethoxy-4-(4-methoxymethoxy-phenyl)-1,3a,4,9b-tetrahydro-3H-cyclopenta[c]chromen-2-one (23)

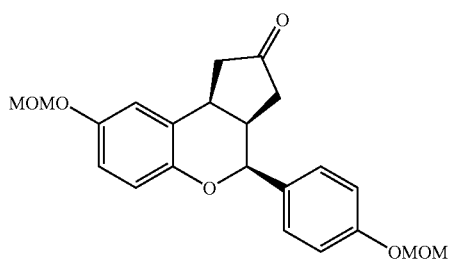

To a solution of flavan 22 (847 mg, 1.91 mmol) in 18 mL of THF was added a solution of LiOH (230 mg, 9.58 mmol) in 9 mL of water. Add 8 mL of THF and 4 mL of water. After stirring for 1 hr, NaH$_2$PO$_4$ (9.6 mL of a 1 M solution in water, 9.6 mmol) was added followed by NaIO$_4$ (2.0 g, 9.35 mmol). After stirring for 1 hr, the solution was diluted with EtOAc. The aqueous solution was separated and extracted with EtOAc. The combined organic solutions were washed with 1:1 saturated aqueous Na$_2$SO$_3$:bicarbonate, brine, dried over Na$_2$SO$_4$, filtered, and concentrated to give 760 mg, 1.97 mmol, 100% of cyclopentanone 23. $^1$H NMR (400 MHz, CDCl$_3$) δ 7.35 (d, 2H, J=8.8 Hz), 7.06 (d, 2H, J=8.7 Hz), 6.90-6.81 (m, 3H), 5.19 (s, 2H), 5.14-5.08 (m, 3H), 3.87 (t, 1H, J=7.5 Hz), 3.49 (s, 3H), 3.48 (s, 3H), 2.93 (m, 1H), 2.78 (dd, 1H, J=18.5, 8.4 Hz), 2.63 (d, 1H, J=18.5 Hz), 2.33 (dd, 1H, J=18.6, 12.1 Hz), 2.04 (dd, 1H, J=18.6, 8.1 Hz).

Example 8

Preparation of (3aR,4S,9bS)- and (3aS,4R,9bR)-8-Hydroxy-4-(4-hydroxy-phenyl)-1,3a,4,9b-tetrahydro-3H-cyclopenta[c]chromen-2-one

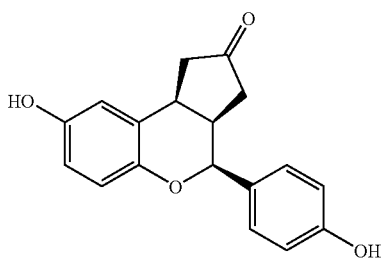

(3aR,4S,9bS)- and (3aS,4R,9bR)-8-Hydroxy-4-(4-hydroxy-phenyl)-1,3a,4,9b-tetrahydro-3H-cyclopenta[c]chromen-2-one (24)

Stir a solution of cyclopentanone 23 (384 mg, 1.0 mmol) in 10 mL of THF and 8 mL of 3 M HCl overnight. Dilute the solution with EtOAc. Separate the aqueous solution and extract 2× with EtOAc. The combined organic solutions were washed with saturated aqueous sodium bicarbonate, brine, dried over Na$_2$SO$_4$, filtered, and concentrated to afford 304 mg of cyclopentanone 24. The material was purified by preparative chiral chromatography (Chiralpak AD, 65/35 heptane/ethanol).

Enantiomer A: HPLC (Zorbax C18 column; 10 to 100% CH$_3$CN/H$_2$O for 10 min then 100% CH$_3$CN for 5 min; 1 mL/min; t$_r$ 8.34 min). HPLC (Chiralpak AD, 65/35 heptane/ethanol, 1 mL/min; t$_R$=4.1 min). LRMS (ES−) calcd for C$_{18}$H$_{15}$O$_4$: 295.10; found: 295.29 (M−H).

Enantiomer B: HPLC (Zorbax C18 column; 10 to 100% CH$_3$CN/H$_2$O for 10 min then 100% CH$_3$CN for 5 min; 1 mL/min; t$_r$ 8.37 min). HPLC (Chiralpak AD, 65/35 heptane/ethanol, 1 mL/min; t$_R$=5.3 min). LRMS (ES−) calcd for C$_{18}$H$_{15}$O$_4$: 295.10; found: 295.29 (M−H).

Preparation 19

8-Methoxymethoxy-4-(4-methoxymethoxy-phenyl)-1,2,3,3a,4,9b-hexahydro-cyclopenta[c]chromen-2-ol (25)

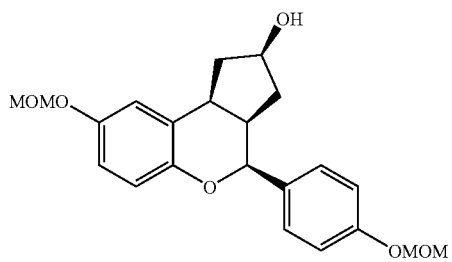

To a solution of cyclopentanon 23 (60 mg, 0.16 mmol) in 1 mL of MeOH and 0.5 mL of THF was added NaBH$_4$ (15 mg, 0.40 mmol). After stirring for 2 hrs saturated aqueous ammonium chloride was added. The solution was diluted with EtOAc. The aqueous solution was extracted 2× with EtOAc. The combined organic extracts were washed with brine, dried over Na$_2$SO$_4$, filtered and concentrated to give 60 mg (0.16 mmol, 100%) of alcohol 25. HRMS (ES+) calc for C$_{22}$H$_{30}$NO$_6$: 404.2073, found: 404.2082 (M+NH$_4$).

Example 9

Preparation of (2R,3aR,4S,9bS)- and (2S,3aS,4R,9bR)-4-(4-Hydroxy-phenyl)-1,2,3,3a,49b-hexahydro-cyclopenta[c]chromene-2,8-diol

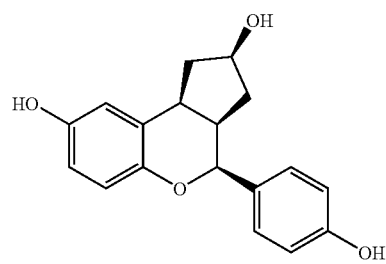

(2R,3aR,4S,9bS)- and (2S,3aS,4R,9bR)-4-(4-Hydroxy-phenyl)-1,2,3,3a,4,9b-hexahydro-cyclopenta[c]chromene-2,8-diol (26)

Stir a solution of alcohol 25 (60 mg, 0.16 mmol) in 2 mL of THF and 2 mL of 3 M HCl overnight. Dilute the solution with EtOAc. Separate the aqueous solution and extract 2× with 10% MeOH in EtOAc. Wash the combined organic solutions with saturated aqueous sodium bicarbonate, brine, dry over $Na_2SO_4$, filter, and concentrate. Absorb to 1 g silica gel. Purify by silica gel chromatography (4 g silica gel, 0 to 10% $MeOH/CH_2Cl_2$ then 20% $MeOH/CH_2Cl_2$) to give 37 mg, (0.12 mmol, 79%) of alcohol 26. HPLC (Zorbax C18 column 10 to 100% $CH_3CN/H_2O$ for 10 min then 100% $CH_3CN$ for 5 min; 1 mL/min; $t_r$ 7.79 min). LRMS (ES−) calcd for $C_{18}H_{15}O_4$: 297.11; found: 297.29 (M−H).

Preparation 20

8-Methoxymethoxy-4-(4-methoxymethoxy-phenyl)-1,2,3,3a,4,9b-hexahydro-cyclopenta[c]chromen-2-ol (27)

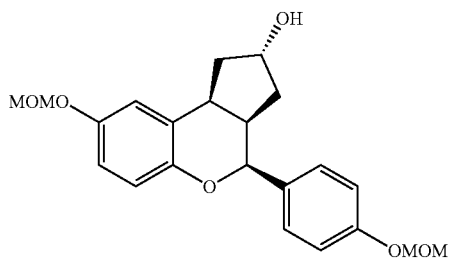

Cool a solution of alcohol 25 (50 mg, 0.13 mmol), triphenylphosphine (68 mg, 0.26 mmol), benzoic acid (24 mg, 0.2 mmol) to 0° C. Add diisopropyl azodicarboxylate (50 ul, 0.26 mmol) slowly so that temperature of reaction does not rise above about 4° C. After addition is complete, remove ice bath and warm the reaction to room temperature and stir overnight. Add MeOH to the reaction mixture and stir for 15 minutes before concentrating to a yellow oil. Purify by flash chromatography (10 g $SiO_2$, 40 mL/min, 0-40% EtOAc/Hexanes over 20 minutes and 40% EtOAc/Hexane for 13 minutes) to yield 67 mg of a clear oil. To a solution of the clear oil (64 mg, 0.13 mmol) in $THF:H_2O$ (1:1, 4 mL) add lithium hydroxide (4 mg, 0.13 mmol) and stir the reaction at room temperature overnight. Heat the mixture to 60° C. with stirring for 2 hours. Cool the mixture to room temperature and neutralize with 1.0 N HCl. Dilute with EtOAc and wash with saturated sodium bicarbonate and brine. Dry the organic solution ($Na_2SO_4$), filter and concentrate in vacuo. Purify by flash chromatography (10 g $SiO_2$, 40 mL/min, 0-70% EtOAc/hexanes over 20 minutes and then 70% EtOAc/hexanes for 13 minutes) to give 41 mg (0.106 mmol, 82%) of alcohol 27 as a colorless oil. $^1$H NMR (δ, 400 MHz, $CDCl_3$) 7.36 (d, 2H, J=8.8 Hz), 7.05 (d, 2H, J=8.8 Hz), 6.86-6.79 (m, 3H), 5.19 (s, 2H), 5.13 (d, 1H, J=6.8 Hz), 5.10 (d, 1H, 6.8 Hz), 5.07 (d, 1H, J=2.2 Hz), 4.32 (m, 1H), 3.65 (dt, 1H, J=3.5, 8.4 Hz), 3.50 (s, 3H), 3.49 (s, 3H), 2.99 (m, 1H), 2.27 (m, 1H), 2.07 (ddd, 1H, J=3.9, 5.6, 13.6), 1.87 (ddd, 1H, J=5.2, 11.6, 13.6 Hz), 1.42 (m, 1H), 1.27 (s, 1H). HRMS (ES+) calcd for $C_{22}H_{30}NO_6$: 404.2073; found: 404.2057 ($M+NH_4$).

Preparation 21

2,2-Difluoro-8-methoxymethoxy-4-(4-methoxymethoxy-phenyl)-1,2,3,3a,4,9b-hexahydro-cyclopenta[c]chromene (29)

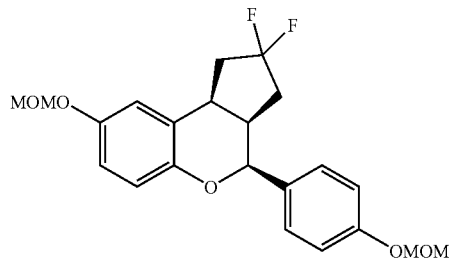

Stir a solution of cyclopentanone 23 (273 mg, 0.710 mmol) in 0.5 mL of (diethylamino)sulfur trifluoride and 0.5 mL of dichloroethane in a 4 mL vial at 40° C. overnight. Dilute with $CH_2Cl_2$ and wash 2× with saturated aqueous sodium bicarbonate. Dry the organic solution over $Na_2SO_4$, filter, and concentrate. Absorb to 5 g of silica gel and purify by silica gel chromatography (35 g silica gel, 0 to 30% EtOAc/Hexanes over 48 min at 35 mL/min) to give 217 mg (0.53 mmol, 75%) of difluorocyclopentane 29. $^1$H NMR (δ, 400 MHz, $CDCl_3$) 7.34 (d, 2H, J=8.4 Hz), 7.06 (d, 2H, J=8.4 Hz), 6.90-6.83 (m, 2H), 6.80 (s, 1H), 5.19 (s, 2H), 5.13 (d, 1H, J=6.8 Hz), 5.11 (d, 1H, J=6.8 Hz), 5.02 (s, 1H), 3.67 (t, 1H, J=8.2 Hz), 3.49 (s, 6H), 2.89-2.67 (m, 2H), 2.40-2.09 (m, 2H), 1.88 (dt, 1H, J=14.3, 7.0 Hz).

Example 10

Preparation of (3aR,4S,9bS)- or (3aS,4R,9bR)-2,2-Difluoro-4-(4-hydroxy-phenyl)-1,2,3,3a,4,9b-hexahydro-cyclopenta[c]chromen-8-ol

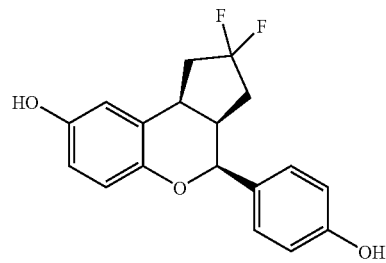

(3aR,4S,9bS)- or (3aS,4R,9bR)-2,2-Difluoro-4-(4-hydroxy-phenyl)-1,2,3,3a,4,9b-hexahydro-cyclopenta[c]chromen-8-ol (30)

Stir a solution of difluorocyclopentane 29 (196 mg, 0.480 mmol) in 7 mL of THF and 3 mL of 3 M HCl overnight. Add 1 mL of 5 M HCl and let stir overnight. Dilute the solution with EtOAc. Separate the aqueous solution and extract 2× with EtOAc. The combined organic solutions were washed with saturated aqueous sodium bicarbonate, brine, dried over Na$_2$SO$_4$, filtered, and concentrated. Absorb to 2 g of silica gel and purify by silica gel chromatography (10 g silica gel, 10 to 60% EtOAc/Hexanes over 30 min at 35 mL/min) to give 155 mg (0.48 mmol, 100%) of difluorocyclopentane 30. The enantiomers were separated by preparative chiral chromatography (Chiralpak AD, 65/35 heptane/ethanol).

Enantiomer A: HPLC (Zorbax C18 column; 10 to 100% CH$_3$CN/H$_2$O for 10 min then 100% CH$_3$CN for 5 min; 1 mL/min; t$_r$ 9.61 min). HPLC (Chiralpak AD, 20/80 IPA/Heptane, 1 mL/min; t$_R$=8.8 min). HRMS (CI+) calcd for C$_{18}$H$_{17}$F$_2$O$_3$: 319.1146; found: 319.1151 (M+H).

Enantiomer B: HPLC (Zorbax C18 column; 10 to 100% CH$_3$CN/H$_2$O for 10 min then 100% CH$_3$CN for 5 min; 1 mL/min; t$_r$ 9.60 min). HPLC (Chiralpak AD, 20/80 IPA/Heptane, 1 mL/min; t$_R$=16.0 min). HRMS (CI+) calcd for C$_{18}$H$_{17}$F$_2$O$_3$: 319.1146; found: 319.1164 (M+H).

Preparation 22

8-Methoxymethoxy-4-(4-methoxymethoxy-phenyl)-2-trifluoromethyl-1,2,3,3a,4,9b-hexahydro-cyclopenta[c]chromene (32 and 33)

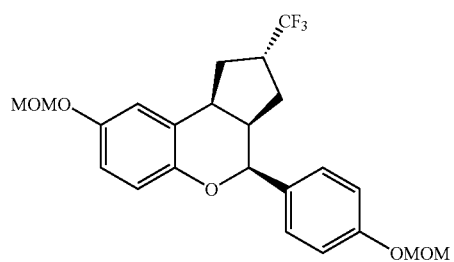

32

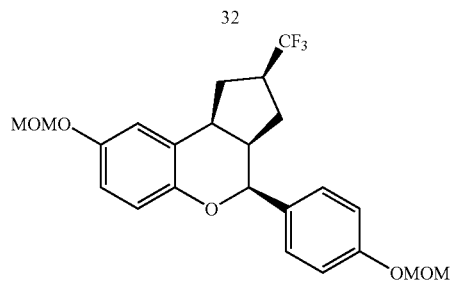

33

Add tetrabutylammonium fluoride (0.075 mL of a 1.0 M solution in THF, 0.075 mmol) to a solution of cyclopentanone 23 (288 mg, 0.75 mmol) and (trifluoromethyl)trimethylsilane (3.75 mL of a 0.5 M solution in THF, 1.875 mmol) in 5 mL of THF. After stirring for 2 hrs, add another 1.5 mL of (trifluoromethyl)trimethylsilane and 0.030 mL of tetrabutylammonium fluoride. After stirring for 1 hr, add another 0.75 mL of (trifluoromethyl)trimethylsilane and 0.015 mL of tetrabutylammonium fluoride. After stirring for 30 min, add saturated aqueous ammonium chloride. Extract the aqueous solution with EtOAc. Combine the organic solutions and wash with water, brine, dry over Na$_2$SO$_4$, filter and concentrate to an oil. To a solution of the oil in 5 mL of THF add TBAF (0.75 mL of a 1.0 M solution in THF, 0.075 mmol). After stirring for 15 min add saturated aqueous sodium bicarbonate. Extract the aqueous solution with EtOAc. Combine the organic solutions and wash with water, brine, dry over Na$_2$SO$_4$, filter and concentrate to 350 mg of an oil which was used without further purification. To a solution of the oil, DMAP (10 mg, 0.08 mmol) and Et$_3$N (0.325 mL, 2.26 mmol) in 4 mL of dichloromethane add methyl chloroglyoxylate (0.105 mL, 1.14 mmol). After stirring for 1 hr, add another 0.16 mL of Et$_3$N and 0.050 mL of methyl chloroglyoxylate. After stirring for 30 min dilute the solution with EtOAc, wash with saturate aqueous sodium bicarbonate, brine, dry over Na$_2$SO$_4$, filter and concentrate. Absorb to 2 g of silica gel and purify by silica gel chromatography (10 g silica gel, 0 to 30% EtOAc/Hexanes over 20 min and then 30% EtOAc/Hexanes at 35 mL/min) to give 360 mg (0.67 mmol, 89%) of an oil which was used without further purification. A solution of the oil (320 mg, 0.59 mmol), triphenylsilane (625 mg, 1.78 mmol), and AIBN (15 mg, 0.091 mmol) in 6 mL of toluene was heated to 80° C. for 4 hrs. The solution was cooled to room temperature, filtered, and the precipitate washed with Et$_2$O—Combine the filtrates and concentrate. Absorb to 2 g of silica gel and purify by silica gel chromatography (35 g silica gel, 0 to 30% EtOAc/Hexanes over 48 min at 35 mL/min) to give 114 mg (0.26 mmol, 44%) of trifluoromethyl 32 and 136 mg (0.31 mmol, 52%) of trifluoromethyl 33. The structures were assigned by 2D NMR spectroscopy (gDQCOSY, edited HSQC, and 2D-NOESY). Trifluoromethyl 32: HRMS (FAB) calcd for C$_{23}$H$_{25}$F$_3$O$_5$: 438.1654; found: 438.1657 (M+H). Trifluoromethyl 33: HRMS (FAB) calcd for C$_{23}$H$_{25}$F$_3$O$_5$: 438.1654; found: 438.1657 (M+H).

Example 11

Preparation of (2S,3aR,4S,9bS)- and (2R,3aS,4R,9bR)-4-(4-Hydroxy-phenyl)-2-trifluoromethyl-12,33a,4,9b-hexahydro-cyclopenta[c]chromen-8-ol

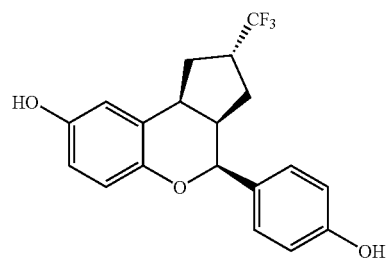

(2S,3aR,4S,9bS)- and (2R,3aS,4R,9bR)-4-(4-Hydroxy-phenyl)-2-trifluoromethyl-1,2,3,3a,4,9b-hexahydro-cyclopenta[c]chromen-8-ol (34)

Stir a solution of trifluoromethyl 32 (105 mg, 0.240 mmol) in 4 mL of THF and 2 mL of 3 M HCl overnight. Add 1 mL of THF and 0.5 mL of 12 M HCl. After stirring for 6 hrs, dilute the solution with EtOAc. Separate the aqueous solution and extract 2× with EtOAc. Wash the combined organic solutions with saturated aqueous sodium bicarbonate, brine, dry over Na$_2$SO$_4$, filter, and concentrate. Absorb to 2 g of silica gel and purify by silica gel chromatography (10 g silica gel, 0 to 40% EtOAc/Hexanes over 30 min at 35 mL/min) to give 62 mg (0.18 mmol, 74%) of trifluoromethyl 34. The enantiomers were separated by preparative chiral chromatography (Chiralpak AD, IPA/heptane).

Enantiomer A: HPLC (Zorbax C18 column; 10 to 100% CH$_3$CN/H$_2$O for 10 min then 100% CH$_3$CN for 5 min; 1 mL/min; t, 10.32 min). HPLC (Chiralpak AD, 30/70 IPA/Heptane, 1 mL/min; $t_R$=2.53 min). HRMS (ES−) calcd for $C_{19}H_{16}F_3O_3$: 349.1052; found: 349.1059 (M−H).

Enantiomer B: HPLC (Zorbax C18 column; 10 to 100% $CH_3CN/H_2O$ for 10 min then 100% $CH_3CN$ for 5 min; 1 mL/min; t, 10.32 min). HPLC (Chiralpak AD, 30/70 IPA/Heptane, 1 mL/min; $t_R$=3.68 min). HRMS (ES−) calcd for $C_{19}H_{16}F_3O_3$: 349.1052; found: 349.1078 (M−H).

Example 12

Preparation of (2R,3aR,4S,9bS)- and (2S,3aS,4R,9bR)-4-(4-Hydroxy-phenyl)-2-trifluoromethyl-1,2,33a,4,9b-hexahydro-cyclopenta[c]chromen-8-ol

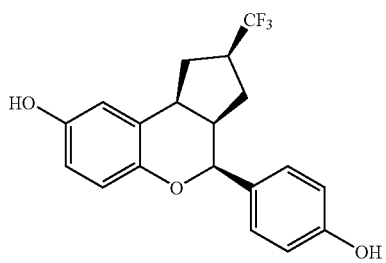

(2R,3aR,4S,9bS)- and (2S,3aS,4R,9bR)-4-(4-Hydroxy-phenyl)-2-trifluoromethyl-1,2,3,3a,4,9b-hexahydro-cyclopenta[c]chromen-8-ol (35)

Stir a solution of trifluoromethyl 33 (125 mg, 0.290 mmol) in 4 mL of THF and 2 mL of 3 M HCl overnight. Add 1 mL of THF and 0.5 mL of 12 M HCl. After stirring for 6 hrs, dilute the solution with EtOAc. Separate the aqueous solution and extract 2× with EtOAc. Wash the combined organic solutions with saturated aqueous sodium bicarbonate, brine, dry over $Na_2SO_4$, filter, and concentrate. Absorb to 2 g of silica gel and purify by silica gel chromatography (10 g silica gel, 0 to 50% EtOAc/Hexanes over 30 min at 35 mL/min) to give 92 mg (0.18 mmol, 91%) of trifluoromethyl 35. The enantiomers were separated by preparative chiral chromatography (Chiralpak AD, IPA/heptane).

Enantiomer A: HPLC (Zorbax C18 column; 10 to 100% $CH_3CN/H_2O$ for 10 min then 100% $CH_3CN$ for 5 min; 1 mL/min; t, 10.13 min). HPLC (Chiralpak AD, 30/70 IPA/Heptane, 1 mL/min; $t_R$=2.96 min). HRMS (ES−) calcd for $C_{19}H_{16}F_3O_3$: 349.1052; found: 349.1086 (M−H).

Enantiomer B: HPLC (Zorbax C18 column; 10 to 100% $CH_3CN/H_2O$ for 10 min then 100% $CH_3CN$ for 5 min; 1 mL/min; t, 10.13 min). HPLC (Chiralpak AD, 30/70 IPA/Heptane, 1 mL/min; $t_R$=4.66 min). HRMS (ES−) calcd for $C_{19}H_{16}F_3O_3$: 349.1052; found: 349.1064 (M−H).

Preparation 23

2-Ethyl-8-methoxymethoxy-4-(4-methoxymethoxy-phenyl)-1,2,3,3a,4,9b-hexahydro-cyclopenta[c]chromen-2-ol (31)

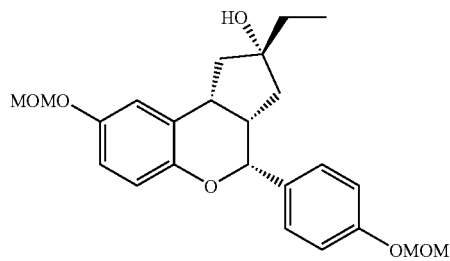

Heat $CeCl_3\cdot 7H_2O$ (97 mg, 0.26 mmol) under vacuum at 70° C. for two hours and then warm slowly to 120° C. and continue heating overnight. Cool to room temperature and add THF (3 mL) followed by cyclopentanone 23 (100 mg, 0.26 mmol) and stir the solution for 45 minutes. Cool the reaction to −10° C., add EtMgCl (3.0 M in THF, 87 ul, 0.26 mmol) and stir the reaction for 30 minutes. Quench the reaction with saturated aqueous $NH_4Cl$ and extract with EtOAc (2×). Combine the organic extracts, wash with brine, dry ($Na_2SO_4$), filter and concentrate. Purify by flash chromatography (10 g silica gel, 40 mL/min, dry loading on 700 mg of silica gel, 0-30% EtOAc/hexanes for 20 minutes and 30% EtOAc/hexanes for 13 minutes) to afford Alcohol 31 (86 mg, 0.207 mmol, 81%). $^1$H NMR (δ, 400 MHz, $CDCl_3$) 7.36 (d, 2H, J=8.8 Hz), 7.05 (d, 2H, J=8.8 Hz), 6.90-6.87 (m, 2H), 6.83 (dd, 1H, J=8.8, 2.6 Hz), 5.19 (s, 2H), 5.14 (d, 1H, J=6.8 Hz), 5.10 (d, 1H, J=6.8 Hz), 5.05 (d, 1H, J=2.2 Hz), 3.54 (dd, 1H, J=7.6, 7.6 Hz), 3.51 (s, 3H), 3.49 (s, 3H), 2.70 (ddd, 1H, J=2.2, 7.6, 9.6 Hz), 2.22 (dd, 1H, J=13.6, 7.9 Hz), 2.03 (d, 1H, J=13.6 Hz), 1.84 (dd, 1H, J=14.1, 10.1 Hz), 1.67 (dd, 1H, J=14.1, 9.2 Hz), 1.52 (m, 2H), 0.89 (t, 3H, J=7.3 Hz).

Example 13

Preparation of (2R,3aR,4S,9bS)- and (2S,3aS,4R,9bR)-2-Ethyl-4-(4-hydroxy-phenyl)-1,2,3,3a,4,9bR-hexahydro-cyclopenta[c]chromene-2,8-diol

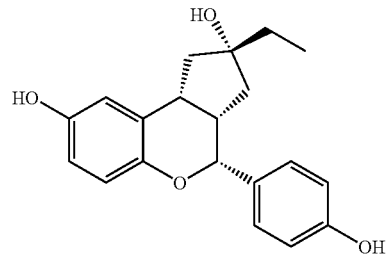

(2R,3aR,4S,9bS)- and (2S,3aS,4R,9bR)-2-Ethyl-4-(4-hydroxy-phenyl)-1,2,3,3a,4,9b-hexahydro-cyclopenta[c]chromene-2,8-diol (37)

Dissolve alcohol 36 (80 mg, 0.19 mmol) in THF (2 mL) and add 3 M HCl (2.0 mL). Stir the reaction at room temperature overnight. Dilute the reaction with EtOAc and wash with saturated aqueous sodium bicarbonate and brine. Extract the aqueous solutions with EtOAc (1×). Combine organic solutions, dry ($Na_2SO_4$), filter and concentrate in vacuo. Purify by flash chromatography (10 g $SiO_2$, dry loading on 700 mg silica gel, 40 ml/min, 0-40% EtOAc/Hexane over 25 minutes and then 40% EtOAc/hexane for 7 minutes) to afford alcohol 37 (20 mg, 0.061 mmol, 32%) as a white solid. HRMS (ES+) calcd for $C_{20}H_{23}O_4$: 327.1596; found: 327.1596 (M+H). HPLC (Zorbax C18 column; 10 to 100% $CH_3CN/H_2O$ for 10 min then 100% $CH_3CN$ for 5 min; 1 mL/min; $t_r$ 8.6 min).

Preparation 24

2-Ethyl-8-methoxymethoxy-4-(4-methoxymethoxy-phenyl)-1,2,3,3a,4,9b-hexahydro-cyclopenta[c]chromene (38)

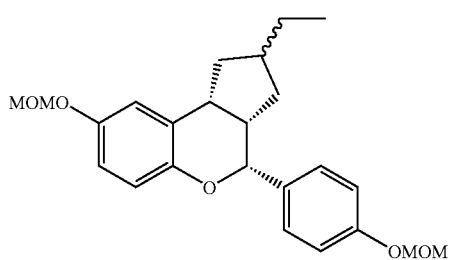

Prepare a solution of alcohol 31 (145 mg, 0.32 mmol), DMAP (5 mg, 0.035 mmol), and $Et_3N$ (146 ul, 1.05 mmol) in $CH_2Cl_2$ (4 mL). Add methyl chloroglyoxylate (46 ul, 0.52 mmol) drop wise. Stir the reaction under $N_2$ for 30 minutes. Dilute with EtOAc and wash with saturated aqueous sodium bicarbonate, 1.0 M HCl, saturated aqueous sodium bicarbonate and brine. Dry the organic solution over $Na_2SO_4$, filter, and concentrate in vacuo. Purification by flash chromatography (10 g $SiO_2$, 40 mL/min, dry loading on 500 mg silica, 0-30% EtOAc/Hexanes for 20 minutes and then 30% EtOAc/Hexanes for 13 minutes) afforded 142 mg (0.28 mmol, 81%) of an oil which was used without further purification. Dissolve the oil (138 mg, 0.28 mmol) and triphenyl tinhydride (290 mg, 0.83 mmol) in toluene (5 mL). Add AIBN (7 mg, 0.04 mmol) and heat the solution to 80° C. and stir for 18 hours. Filter the precipitate and wash with ether. Combine the filtrates, concentrate and purify by flash chromatography (10 g $SiO_2$, 40 mL/min, dry loading on 800 mg silica, 0-30% EtOAc/Hexane over 20 minutes and then 30% EtOAc/hex for 13 minutes) to afford 107 mg (0.27 mmol, 99%) of alkyl cyclopentane 38 as a 4:1 mixture of diastereomers. HRMS (ES+) calcd for $C_{24}H_{34}NO_5$: 416.2437; found: 416.2432 (M+$NH_4$).

Example 14

Preparation of (2S,3aS,4R,9bR)- and (2R,3aS,4R,9bR)- and (2S,3aR,4S,9bS)- and (2R,3aR,4S,9bS)-2-Ethyl-4-(4-hydroxy-phenyl)-1,2,33a,4,9b-hexahydro-cyclopenta [c]chromen-8-ol

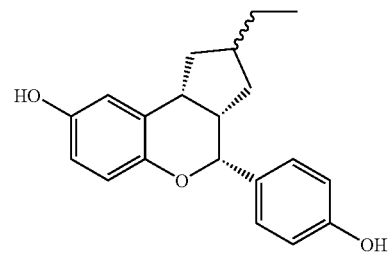

(2S,3aS,4R,9bR)- and (2R,3aS,4R,9bR)- and (2S,3aR,4S,9bS)- and (2R,3aR,4S,9bS)-2-Ethyl-4-(4-hydroxy-phenyl)-1,2,3,3a,4,9b-hexahydro-cyclopenta[c]chromen-8-ol (39)

Dissolve alkyl cyclopentane 38 (109 mg, 0.27 mmol) in THF (4 mL) then add 3 M HCl (1.0 mL). Stir the reaction at room temperature overnight. Dilute the reaction with EtOAc and wash with saturated aqueous sodium bicarbonate and brine. Extract the aqueous layer with EtOAc (1×). Combine the organic extracts, dry ($Na_2SO_4$), filter and concentrate in vacuo. Purify by flash chromatography (10 g $SiO_2$, dry loading on 700 mg silica, 40 ml/min, 0-30% EtOAc/Hexane over 25 minutes and then 30% EtOAc/hexane for 7 minutes) to afford 56 mg (0.18 mmol, 68%) of alkyl cyclopentane 39 as a white solid. HRMS (ES+) calcd for $C_{20}H_{26}NO_3$: 328.1913; found: 328.1906 (M+$NH_4$). HPLC (Zorbax C18 column; 10 to 100% $CH_3CN/H_2O$ for 10 min then 100% $CH_3CN$ for 5 min; 1 mL/min; $t_r$ 9.33 min).

Preparation 25

2-Methoxy-8-methoxymethoxy-4-(4-methoxymethoxy-phenyl)-1,2,3,3a,4,9b-hexahydro-cyclopenta [c]chromene (40)

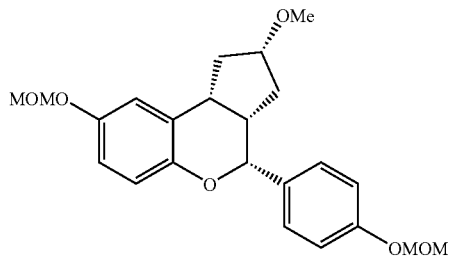

To a solution of alcohol 25 (200 mg, 0.52 mmol) in DMF (5 mL) add sodium hydride (60% dispersion in mineral oil, 21 mg, 0.51 mmol) and stir the reaction at room temperature for 10 minutes. Cool the reaction to 0° C. and add methyl iodide (33 ul, 0.52 mmol) and stir the reaction mixture for 2 hours. Quench the reaction with saturated NH₄Cl and extract with EtOAc (2×). Combine the organic extracts and wash with H₂O, saturated aqueous sodium bicarbonate and brine. Dry (Na₂SO₄), filter and concentrate the solution in vacuo. Purify by flash chromatography (10 g SiO₂, 40 mL/min, 0-40% EtOAc/Hexanes over 20 minutes and then 40% EtOAc/Hexanes for 13 minutes) to methyl ether 40 (210 mg, 0.52 mmol, 100%) as a yellow oil HRMS (ES+) calcd for $C_{23}H_{29}O_6$: 401.1964; found: 401.1969 (M+H).

Example 15

Preparation of (2S,3aS,4R,9bR)- and (2R,3aR,4S, 9bS)-4-(4-Hydroxy-phenyl)-2-methoxy-12,33a,4,9b-hexahydro-cyclopenta[c]chromen-8-ol

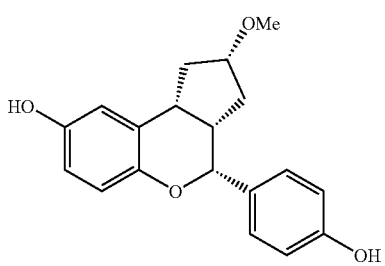

(2S,3aS,4R,9bR)- and (2R,3aR,4S,9bS)-4-(4-Hydroxy-phenyl)-2-methoxy-1,2,3,3a,4,9b-hexahydro-cyclopenta[c]chromen-8-ol (41)

Dissolve methyl ether 40 (205 mg, 0.51 mmol) in THF (8 mL) and add 3M HCl (2 mL). Stir the reaction at room temperature overnight. Dilute the reaction with EtOAc and wash with saturated aqueous sodium bicarbonate and brine. Extract the aqueous solutions with EtOAc (1×). Combine the organic solutions, dry (Na₂SO₄), filter and concentrate them in vacuo. Purify the product by flash chromatography (10 g SiO₂, dry loading on 700 mg silica, 40 ml/min, 0-50% EtOAc/Hexane over 20 minutes and then 50% EtOAc/hexane for 13 minutes) to afford methyl ether 41 (125 mg, 0.4 mmol, 78%) as a white solid. HRMS (ES+) calcd for $C_{19}H_{23}NO_4$: 330.1705; found: 330.1695 (M+NH₄); HPLC (Zorbax C18 column; 10 to 100% CH₃CN/H₂O for 10 min then 100% CH₃CN for 5 min; 1 mL/min; $t_r$ 8.95 min). The enantiomers were separated by preparative chiral chromatography, chiralpol AD, IPA/Heptane.

Enantiomer A: HRMS (ES+) calcd for $C_{19}H_{24}NO_4$: 330.1705; found: 330.1691 (M+NH₄). HPLC (Chiralpak AD, 30-70% IPA/Heptane for 15 min; 1 mL/min; $t_R$=3.52 min). HPLC (Zorbax C18 column; 10 to 100% CH₃CN/H₂O for 10 min then 100% CH₃CN for 5 min; 1 mL/min; $t_r$ 8.95 min).

Enantiomer B: HRMS (ES+) calcd for $C_{19}H_{24}NO_4$: 330.1705; found: 330.1695 (M+NH₄). HPLC (Chiralpak AD, 30-80% IPA/Heptane for 15 min; 1 mL/min; $t_R$=6.15 min). HPLC (Zorbax C18 column; 10 to 100% CH₃CN/H₂O for 10 min then 100% CH₃CN for 5 min; 1 mL/min; $t_r$=6.96 min).

Preparation 25

Acetic acid 8-methoxymethoxy-4-(4-methoxymethoxy-phenyl)-1,2,3,3a,4,9b-hexahydro-cyclopenta[c]chromen-2-yl ester (42)

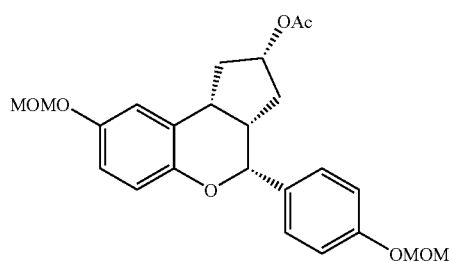

Add acetic anhydride (53 mg, 0.52 mmol) to a solution of alcohol 25 (200 mg, 0.52 mmol), Et₃N (0.14 mL, 1.03 mmol), and DMAP (6 mg, 0.052 mmol) in CH₂Cl₂ (5 mL) and stir the reaction at room temperature for 1 hour. Dilute the solution with EtOAc and wash with H₂O, saturated aqueous sodium bicarbonate and brine. Dry (Na₂SO₄), filter and concentrate the solution in vacuo. Purify the product by flash chromatography (10 g SiO₂, 40 mL/min, 0-40% EtOAc/Hexanes over 20 minutes and then 40% EtOAc/Hexanes for 13 minutes) to afford acetate 42 (183 mg, 0.43 mmol, 83%) as a yellow oil. HRMS (FAB+) calcd for $C_{24}H_{28}O_7$: 428.1835; found: 428.1833 (M+).

Example 16

Preparation of (2S,3aS,4R,9bR)- and (2R,3aR,4S, 9bS)-Acetic acid 8-hydroxy-4-(4-hydroxy-phenyl)-1,2,3,3a,4,9b-hexahydro-cyclopenta[c]chromen-2-yl ester

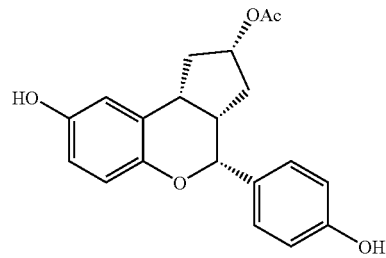

(2S,3aS,4R,9bR)- and (2R,3aR,4S,9bS)-Acetic acid 8-hydroxy-4-(4-hydroxy-phenyl)-1,2,3,3a,4,9b-hexahydro-cyclopenta[c]chromen-2-yl ester (43)

Dissolve acetate 42 (180 mg, 0.42 mmol) in THF (8 mL) and add 3M HCl (2 mL). Stir the reaction at room temperature overnight. Dilute the reaction with EtOAc and wash with saturated aqueous sodium bicarbonate and brine. Extract the aqueous solutions with EtOAc (1×). Combine, dry (Na₂SO₄), filter and concentrate the organic solutions in vacuo. Purify the product by flash chromatography (10 g SiO₂, dry loading on 700 mg silica, 40 ml/min, 0-50% EtOAc/Hexane over 20 minutes and then 50% EtOAc/hexane for 13 minutes) to afford acetate 43 (47 mg, 0.14 mmol, 33%) as a white solid. The enantiomers were separated.

Enantiomer A: HRMS (ES+) calcd for $C_{20}H_{24}NO_5$: 358.1654; found: 358.1636 (M+NH$_4$). HPLC (Chiralpak AD, 20-80% IPA/Heptane for 15 min; 1 mL/min; $t_R$=3.73 min). HPLC (Zorbax C18 column; 10 to 100% CH$_3$CN/H$_2$O for 10 min then 100% CH$_3$CN for 5 min; 1 mL/min; $t_r$ 9.07 min).

Enantiomer B: HRMS (ES+) calcd for $C_{20}H_{24}NO_5$: 358.1654; found: 358.1641 (M+NH$_4$). HPLC (Chiralpak AD, 20-80% IPA/Heptane for 15 min; 1 mL/min; $t_R$=5.35 min). HPLC (Zorbax C18 column; 10 to 100% CH$_3$CN/H$_2$O for 10 min then 100% CH$_3$CN for 5 min; 1 mL/min; $t_r$ 9.07 min).

Preparation 26

2-Fluoro-8-methoxymethoxy-4-(4-methoxymethoxy-phenyl)-1,2,3,3a,4,9b-hexahydro-cyclopenta[c]chromene (44)

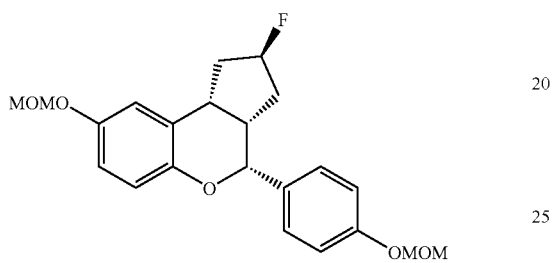

Dissolve alcohol 25 (120 mg, 0.32 mmol) in CH$_2$Cl$_2$ (5 mL). Add N,N-diethyl amino sulfurtrifluride (0.8 mL, 6.0 mmol) and stir the reaction at room temperature overnight. Dilute the reaction with CH$_2$Cl$_2$ and wash with saturated aqueous sodium bicarbonate. Extract the aqueous layer with CH$_2$Cl$_2$ (1×). Combine the organic extracts, dry (Na$_2$SO$_4$), filter and concentrate them in vacuo. Purify the product by flash chromatography (10 g SiO$_2$, 40 mL/min, dry loading on 800 mg silica, 10-30% EtOAc/hexane over 33 minutes) to afford fluororcyclopentane 44 (84 mg, 0.217 mmol, 70%). HRMS (ES+) calcd for $C_{22}H_{26}FO_5$: 389.1764; found: 489.1761 (M+H).

Example 17

Preparation of (2R,3aS,4R,9bR)- and (2S,3aR,4S,9bS)-2-Fluoro-4-(4-hydroxy-phenyl)-1,2,3,3a,4,9b-hexahydro-cyclopenta[c]chromen-8-ol

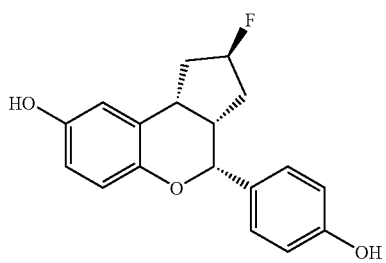

(2R,3aS,4R,9bR)- and (2S,3aR,4S,9bS)-2-Fluoro-4-(4-hydroxy-phenyl)-1,2,3,3a,4,9b-hexahydro-cyclopenta[c]chromen-8-ol (45)

Dissolve fluorocyclopentane 44 (78 mg, 0.201 mmol) in THF (2 mL) and add 3M HCl (0.5 mL). Stir the reaction at room temperature overnight. Dilute the reaction with EtOAc and wash with saturated aqueous sodium bicarbonate and brine. Extract the aqueous solutions with EtOAc (1×). Combine the organic extracts, dry (Na$_2$SO$_4$), filter and concentrate them in vacuo. Purify the product by flash chromatography (10 g SiO$_2$, dry loading on 700 mg silica, 40 ml/min, 0-30% EtOAc/Hexane over 20 minutes and then 30% EtOAc/hexane for 13 minutes) to afford fluorocyclopentane 45 (54 mg, 0.18 mmol, 90%) as a white solid. The enantiomers were separated by preparative chiral chromatography (Chiralpak AD, IPA/heptane).

Enantiomer A: HRMS (ES+) calcd for $C_{18}H_{17}FO_3$: 301.1240; found: 301.1221 (M+H). HPLC (Chiralpak AD, 20-80% IPA/Heptane for 15 min; 1 mL/min; $t_R$=5.88 min). HPLC (Zorbax C18 column; 10 to 100% CH$_3$CN/H$_2$O for 10 min then 100% CH$_3$CN for 5 min; 1 mL/min; $t_r$ 9.46 min).

Enantiomer B: HRMS (ES+) calcd for $C_{18}H_{18}FO_3$: 301.1240; found: 301.1226 (M+H). HPLC (Chiralpak AD, 20-80% IPA/Heptane for 15 min; 1 mL/min; $t_R$=7.13 min). HPLC (Zorbax C18 column; 10 to 100% CH$_3$CN/H$_2$O for 10 min then 100% CH$_3$CN for 5 min; 1 mL/min; $t_r$ 9.49 min).

Example 18

Preparation of (2S,3aS,4R,9bR)- and (2R,3aR,4S,9bS)-2-Fluoro-4-(4-hydroxy-phenyl)-1,2,3,3a,4,9b-hexahydro-cyclopenta[c]chromen-8-ol

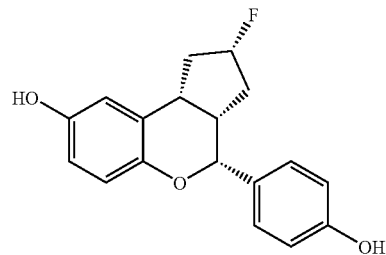

(2S,3aS,4R,9bR)- and (2R,3aR,4S,9bS)-2-Fluoro-4-(4-hydroxy-phenyl)-1,2,3,3a,4,9b-hexahydro-cyclopenta[c]chromen-8-ol (47)

Fluorocyclopentane 47 was prepared from alcohol 27 in a manner substantially similar to fluorocyclopentane 45. HRMS (ES+) calcd for $C_{18}H_{18}FO_3$: 301.1240; found: 301.1241 (M+H).

Preparation 27

6-Benzyloxy-2-oxo-2H-chromene-3-carboxylic acid ethyl ester

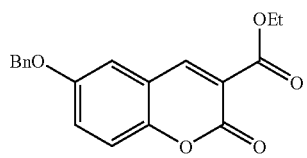

To a 0 C solution of the phenol (26.7 g, 114 mmol) and benzyl bromide (20.5 mL, 171 mmol) in DMF (300 mL) add NaH (6.84 g, 1.5 mmol) portionwise over 15 min. Allow venting during the addition, during which time the solution turns dark red. After 30 min, remove the cooling bath and allow the solution to warm to 23 C, during which time a precipitate forms and the solution turns dark brown. After 2 h, slowly pour the solution into ½ satd. NaHCO₃ (500 mL), and filter the mixture. Wash the filter cake with H₂O (2×300 mL) and 50% Et₂O/hexanes (2×300 mL) to remove remaining aqueous salts and excess benzyl bromide. Dry the remaining yellow solid to afford Preparation 27 (28.9 g, 78%). ¹H NMR (d-DMSO) δ 8.67 (s, 1H), 7.57 (s, 1H), 7.37-7.47 (m, 7H), 5.15 (s, 2H), 4.28 (q, J=7.2 Hz, 2H), 1.31 (t, J=7.2 Hz, 3H).

Preparation 28

2-Benzyloxy-6,9-dioxo-8,9,10,10a-tetrahydro-7H-benzo[c]chromene-6a-carboxylic acid ethyl ester

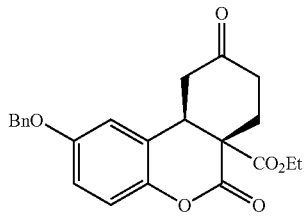

Heat a suspension of Preparation 27, (12.0 g, 37.0 mmol), 2-trimethylsilyloxybutadiene (7.1 g, 55.5 mmol) and hydroquinone (0.040 g) in o-xylenes (40 mL) to 135 C for 24 h. Allow the reaction to cool to 23 C, then pour the contents into a solution of HOAc (5 mL) in TBAF (70 mL, 1 M in THF, 70 mmol). Stir the resulting solution for 1 hour at 23 C, then slowly pour the contents into ½ satd. NaHCO₃ (150 mL) and EtOAc (250 mL). Separate the layers and wash the organic extract with brine (150 mL), dry over Na₂SO₄, and concentrate to afford a brown semisolid. Purify the product by MPLC (0 to 15 to 30% EtOAc/hexanes) to afford Preparation 28 (9.3 g, 63%) as a white solid. ¹H NMR (CDCl₃) δ 7.31-7.42 (m, 5H), 7.04 (d, J=8.8 Hz, 1H), 6.90 (dd, J=2.8, 8.8 Hz, 1H), 6.73 (d, J=2.8 Hz, 1H), 5.03 (d, 2H), 3.98-4.16 (m, 2H), 3.66 (dd, J=3.2, 13.2 Hz, 1H), 2.88 (m, 1H), 2.58-2.72 (m, 2H), 2.49 (m, 1H), 2.38 (t, J=13.6 Hz, 1H), 2.24 (td, J=13.6, 5.2 Hz, 1H), 1.01 (t, J=7.2 Hz, 3H).

Preparation 29

2-Benzyloxy-7,8,10,10a-tetrahydro-6aH-benzo[c]chromene-6,9-dione

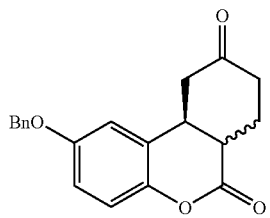

To a solution of Preparation 28 (9.25 g, 23.5 mmol) in THF (75 mL), EtOH (25 mL), and H₂O (40 mL) add lithium hydroxide hydrate (4.92 g, 117 mmol). Attach the flask to a reflux condenser and heat to 60 C for 1 h. Allow the contents to cool to 23 C and pour them into 1 N HCl and extract with Et₂O (2×75 mL) and EtOAc (2×75 mL). Wash the combined organic extracts with brine, dry over Na₂SO₄, and concentrate to afford the intermediate carboxylic acid as an off-white solid, which is used immediately in the next step.

Add o-xylenes (100 mL) to the flask containing the crude acid, and heat the resulting heterogeneous solution to reflux for 2 h. Concentrate the mixture via rotary evaporator to afford Preparation 29 (approx. 9 g, ~quantitative) as an approximately 3:1 inseparable mixture of diastereomers. No further purification is required. ¹H NMR (CDCl₃) δ 7.30-7.44 (m, 5H), 7.02 (d, J=8.8 Hz, 1H), 6.89 (dd, J=8.8, 2.8 Hz, 1H), 6.74 (d, J=2.8 Hz, 1H), 5.04 (s, 3H), 3.02-3.36 (m, 2H), 2.54-2.77 (m, 3H), 2.36-2.45 (m, 2H), 1.93-2.02 (m, 1H).

Preparation 30

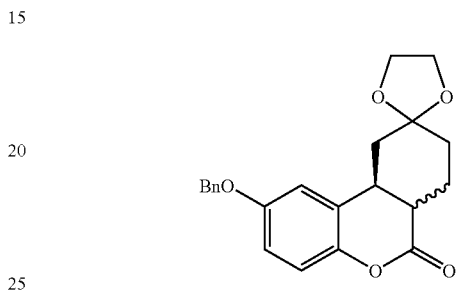

To a solution of Preparation 29 (~9 g, ~23 mmol) and ethylene glycol (2.79 mL, 50 mmol) in toluene (135 mL) add paratoluene sulfonic acid monohydrate (0.44 g, 2.3 mmol). Attach a Dean-Stark trap, and heat the solution to reflux for 2 h. Allow the solution to cool to 23 C, then pour the contents into ½ satd. NaHCO₃ (150 mL) and EtOAc (150 mL). Filter the mixture, and wash the filter cake with EtOAc and CH₂Cl₂. Separate the layers, and further extract the aqueous layer with EtOAc (100 mL) and CH₂Cl₂ (100 mL). Wash the combined organic extracts with brine, dry over Na₂SO₄, and concentrate. Recrystallization from hexanes/toluene (9:1) followed by MPLC purification of the mother liquors (0 to 25 to 40% EtOAc/hexanes) affords Preparation 30 as an inseparable mixture of diastereomers (7.02 g, 82% over 3 steps). Note: Purification may be considered optional, as ¹H NMR of the crude product is fairly clean. ¹H NMR (CDCl₃) δ 7.30-7.44 (m, 5H), 6.95 (d, J=8.8 Hz, 1H), 6.84 (dd, J=8.8, 2.8 Hz, 1H), 6.78 (d, J=2.8 Hz, 1H), 5.03 (s, 2H), 3.98 (m, 4H), 3.02-3.24 (m, 1H), 2.30-2.90 (m, 2H), 1.90-2.22 (m, 4H), 1.54-1.67 (m, 1H).

Preparation 31

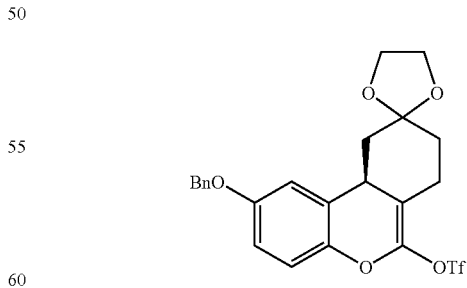

To a −78 C solution of Preparation 30 (7.0 g, 19.1 mmol) in THF (80 mL) add potassium hexamethyldisilane (KHMDS) (53 mL, 0.5 M solution in toluene, 26.7 mmol) over 5 min. Add hexamethylphosphoramide (HMPA) (4.64 mL, 26.7 mmol) quickly, and stir the solution at −78 C for 25 min. Add a solution of N-phenyl triflamide (11.5 g, 32.2 mmol) in THF (15 mL+rinse) via syringe. Maintain the resulting solution at −78 C for 2 h, then pour the reaction contents into ½ satd. NaHCO₃ and extract with Et₂O (150 mL) and EtOAc (2×75 mL). Wash the combined organic extracts with H₂O (2×100 mL) and brine (100 mL), dry over Na₂SO₄, and concentrate. Purification of the crude product by MPLC (0 to 12 to 25% EtOAc/hexanes) affords Preparation 31 (6.25 g, 66%) as an off-white solid. ¹H NMR (CDCl₃) δ 7.25-7.43 (m, 5H), 6.84 (d, J=8.8 Hz, 1H), 6.80 (dd, J=8.8, 2.8 Hz, 1H), 6.72 (d, J=2.8 Hz, 1H), 5.02 (s, 2H), 4.04 (m, 4H), 3.82 (dd, J=4.4, 12.8 Hz, 1H), 2.66 (dq, J=14.0, 2.4 Hz, 1H), 2.21 (m, 2H), 1.91 (m, 1H), 1.80 (t, J=12.8 Hz, 1H), 1.64 (td, J=12.8, 4.4 Hz, 1H).

Preparation 32

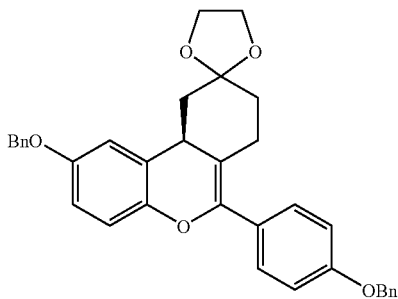

Sparge N₂ (g) through a solution of Preparation 31 (3.0 g, 6.0 mmol), p-benzyloxyphenylboronic acid (1.65 g, 9.0 mmol), and LiCl (0.77 g, 18.1 mmol) in DME (40 mL) and aqueous Na₂CO₃ (7.5 mL, 2 M in H₂O, 15 mmol) for 15 min. Add palladium tetrakis triphenylphosphine (0.69 g, 0.60 mmol), then heat the solution to reflux for 24 h, during which time the product precipitates out as a white solid. Allow the solution to cool to 23 C, then pour the contents into ½ satd NaHCO₃/Et₂O and filter. Wash the filter cake with H₂O and cold Et₂O, affording 2.0 g of Preparation 32. Extract the filtrate with EtOAc (3×50 mL) and dry the combined organic extracts over Na₂SO₄ and concentrate to afford the remaining crude product. Purification of the crude material by silica gel chromatography (CH₂Cl₂) affords another 1.04 g. of Preparation 32. The total yield is 3.04 g (95%). ¹H NMR (CDCl₃) δ 7.31-7.47 (m, 12H), 7.01 (d, J=8.8 Hz, 2H), 6.84 (d, J=8.8 Hz, 1H), 6.77 (d, J=8.8 Hz, 2H), 5.11 (s, 2H), 5.03 (s, 2H), 3.98-4.12 (m, 4H), 3.74 (dd, J=12.8, 4.2 Hz, 1H), 2.58 (m, 1H), 2.24 (m, 1H), 2.14 (td, J=12.8, 4.2 Hz, 1H), 1.85 (t, J=12.8 Hz, 2H), 1.58 (m, 1H).

Preparation 33

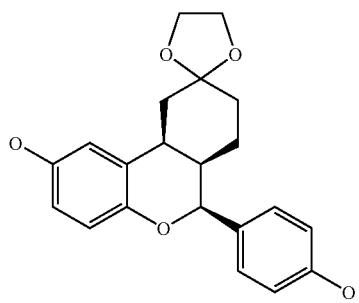

To a mixture of 10 wt % Pd on carbon (0.5 g) in MeOH (100 mL) add a slightly soluble solution of Preparation 32 (3.0 g, 5.63 mmol) in THF (25 mL). Heat the solution to 40 C and maintain under 60 psi of H₂ (g) for 4 h. Filter the solution and concentrate the filtrate to afford Preparation 33 (~1.8 g crude, quantitative) as a white solid. ¹H NMR (CD₃OD) δ 7.22 (d, J=8.8 Hz, 2H), 6.77 (m, 3H), 6.66 (d, J=8.8 Hz, 1H), 6.53 (dd, J=3.2, 8.8 Hz, 1H), 4.98 (s, 1H), 3.88 (m, 1H), 3.76 (m, 2H), 3.68 (m, 1H), 3.47 (m, 1H), 2.48 (d, J=14.8 Hz, 1H), 1.99 (m, 1H), 1.88 (dd, J=14.8, 6.0 Hz, 1H), 1.49-1.61 (m, 2H), 1.37-1.46 (m, 1H), 1.27 (m, 1H), 1.17 (t, J=7.2 Hz, 3H).

Example 19

Preparation of (6S,6aR,10aS)-2-Hydroxy-6-(4-hydroxy-phenyl)-6,6a,7,8,10,10a-hexahydro-benzo[c]chromen-9-one

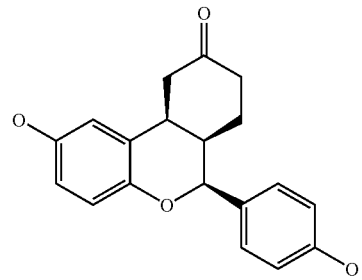

(6S,6aR,10aS)-2-Hydroxy-6-(4-hydroxy-phenyl)-6,6a,7,8,10,10a-hexahydro-benzo[c]chromen-9-one To a solution of Preparation 33 (~1.7 g crude) in THF (40 mL) and H₂O (1 mL) add HCl solution (6 mL, 3 N in H₂O), and stir the mixture overnight. Pour the mixture into satd. NaHCO₃ and extract with Et₂O (2×50 mL) and EtOAc (2×50 mL). Wash the combined organic extracts with brine, dry over Na₂SO₄, and concentrate to afford Example 19 (~1.3 g, ~quantitative) as a light yellow solid. This material is of suitable purity to be used crude for analogue development, but can be recrytallized from a variety of solvents (toluene/MeOH/hexanes or iPrOH/hexanes) for characterization. ¹H NMR (CD₃OD) δ 7.31 (d, J=8.8 Hz, 2H), 6.85 (d, J=8.4 Hz, 2H), 6.75 (d, J=8.4 Hz, 2H), 6.62 (dd, J=8.8, 2.4 Hz, 1H), 5.25 (s, 1H), 3.89 (m, 1H), 2.98 (m, 2H), 2.58 (m, 1H), 2.38 (m, 1H), 2.13 (br d, J=14.4 Hz, 1H), 1.66 (m, 2H).

Preparation 34

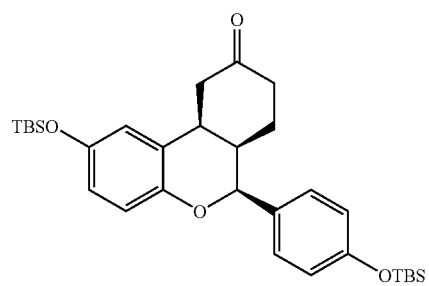

2-(tert-Butyl-dimethyl-silanyloxy)-6-[4-(tert-butyl-dimethyl-silanyloxy)-phenyl]-6,6a,7,8,10,10a-hexahydro-benzo[c]chromen-9-one To a solution of Example 19 (0.120 g, 0.39 mmol) and imidazole (0.079 g, 1.16 mmoL) in DMF (2.5 mL) add tert-butyldimethylsilyl chloride (0.131 g, 0.87 mmol). Allow the reaction to stir for 1 h, then pour into ½ satd. NaHCO$_3$ (50 mL) and extract with Et$_2$O (2×25 mL) and EtOAc (25 mL). Wash the combined organic extracts with H$_2$O (2×25 mL) and brine (25 mL), and dry the organics over Na$_2$SO$_4$—Concentrate the mixture, and purify the residue by MPLC (0% to 10% to 20% EtOAc/hexanes) to afford Preparation 34 (0.184 g, 88%) as a white solid. $^1$H NMR (CDCl$_3$) δ 7.30 (d, J=8.4 Hz, 2H), 6.88 (d, J=8.4 Hz, 2H), 6.77 (d, J=8.8 Hz, 1H), 6.74 (d, J=2.8 Hz, 1H), 6.63 (dd, J=8.8, 2.8 Hz, 1H), 5.27 (s, 1H), 3.85 (m, 1H), 3.01 (d, J=15.2 Hz, 1H), 2.79 (dd, J=5.8, 15.2 Hz, 1H), 2.45 (m, 1H), 2.22 (m, 2H), 1.60-1.80 (m, 2H), 1.01 (s, 9H), 0.99 (s, 9H), 0.23 (s, 6H), 0.21 (s, 3H), 0.19 (s, 3H).

Preparation 35

2-Methoxymethoxy-6-(4-methoxymethoxy-phenyl)-6,6a,7,8,10,10a-hexahydro-benzo[c]chromen-9-one

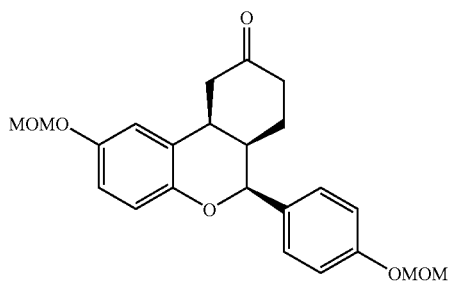

To a 0 C solution of Example 19 (0.100 g, 0.32 mmol) in THF (3 mL) add potassium tert-butoxide (0.090 g, 0.81 mmol) followed by methoxymethyl chloride (MOM-Cl) (0.061 mL, 0.81 mmol). Remove the ice bath and stir for 1 h at room temperature. Pour the contents into ½ satd. NaHCO$_3$ (50 mL) and extract with Et$_2$O (2×25 mL) and EtOAc (2×25 mL). Wash the combine organic extracts with brine (50 mL), dry over Na$_2$SO$_4$, and concentrate to afford a brown residue. Purify the residue by MPLC (0% to 25% to 50% EtOAc/hexanes) to afford Preparation 35 (0.102 g, 80%). $^1$H NMR (CDCl$_3$) δ 7.37 (d, J=8.4 Hz, 2H), 7.09 (d, J=8.4 Hz, 2H), 6.96 (d, J=2.4 Hz, 1H), 6.87 (dd, J=2.4, 8.8 Hz, 1H), 6.84 (d, J=8.8 Hz, 1H), 5.28 (s, 1H), 5.20 (s, 2H), 5.13 (A of AB, J$_{AB}$=7.0 Hz, 1H), 5.07 (B of AB, J$_{AB}$=7.0 Hz, 1H), 3.87 (m, 1H), 3.50 (s, 3H), 3.48 (s, 3H), 3.04 (br d, J=14.4 Hz, 1H), 2.79 (dd, J=6.2, 14.4 Hz, 1H), 2.46 (m, 1H), 2.21 (m, 2H), 1.62-1.79 (m, 2H).

Preparation 36

2-(tert-Butyl-dimethyl-silanyloxy)-6-[4-(tert-butyl-dimethyl-silanyloxy)-phenyl]-9-methylene-6a,7,8,9,10,10a-hexahydro-6H-benzo[c]chromene

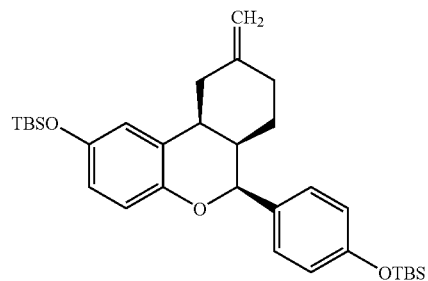

To a −40 C solution of Preparation 34 (0.100 g, 0.19 mmol) in THF (2 mL) and pyridine (0.045 mL) add the Tebbe reagent (Cp$_2$ZrCl(H)Me) (0.74 mL, 0.5 M toluene, 0.37 mmol). Maintain the reaction at 40 C for 1 h, then pour the contents into ½ satd. NaHCO$_3$ (50 mL) and extract with Et$_2$O (2×25 mL) and EtOAc (2×25 mL). Wash the combine organic extracts with brine (50 mL), dry over Na$_2$SO$_4$, and concentrate to afford a brown residue. Purify the residue by MPLC (0% to 5% to 10% EtOAc/hexanes) to afford Preparation 36 (0.093 g, 93%). $^1$H NMR (CDCl$_3$) δ 7.27 (d, J=8.4 Hz, 2H), 6.85 (d, J=8.4 Hz, 2H), 6.75 (m, 2H), 6.61 (dd, J=2.4, 8.8 Hz, 1H), 5.15 (s, 1H), 4.62 (m, 2H), 3.49 (br s, 1H), 2.91 (d, J=14.4 Hz, 1H), 2.51 (dd, J=14.4, 4.6 Hz, 1H), 2.15 (m, 2H), 1.92 (td, J=12.8, 5.6 Hz, 1H), 1.33 (m, 2H), 1.01 (s, 18H), 0.22 (s, 6H), 0.19 (s, 3H), 0.18 (s, 3H).

Example 20

Preparation of (6aR,6S,10aS)-6-(4-Hydroxy-phenyl)-9-methylene-6a,7,8,9,10,10a-hexahydro-6H-benzo[c]chromen-2-ol

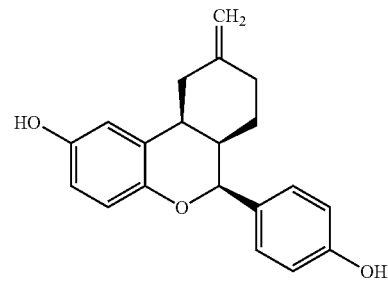

(6aR,6S,10aS)-6-(4-Hydroxy-phenyl)-9-methylene-6a,7,8,9,10,10a-hexahydro-6H-benzo[c]chromen-2-ol To a 0 C solution of Preparation 36 (0.093 g, 0.17 mmol) in THF (5 mL) add a solution of tetra-n-butyl ammonium fluoride (0.43 mL, 1 M in THF, 0.43 mmol). Stir the solution at 0 C for 1 h, then pour the contents into ½ satd. NaHCO₃ (50 mL) and extract with Et₂O (2×25 mL) and EtOAc (2×25 mL). Wash the combine organic extracts with brine (50 mL), dry over Na₂SO₄, and concentrate to afford a brown residue. Purify the residue by MPLC (0% to 25% to 40% EtOAc/hexanes) to afford Example 20 (0.028 g, 52%) as a white solid. ¹H NMR (CD₃OD) δ 7.26 (d, J=8.8 Hz, 2H), 6.82 (d, J=8.8 Hz, 2H), 6.79 (d, J=3.2 Hz, 1H), 6.69 (d, J=8.4 Hz, 1H), 6.57 (dd, J=3.2, 8.4 Hz, 1H), 5.09 (s, 1H), 4.62 (m, 1H), 3.48 (s, 1H), 2.97 (d, J=13.6 Hz, 1H), 2.54 (dd, J=5.2, 13.6 Hz, 1H), 2.17 (m, 2H), 1.95 (td, J=5.2, 12.8 Hz, 1H), 1.25-1.38 (m, 2H).

Example 21

Preparation of (6aR,6S,9S,10aS)-6-(4-Hydroxy-phenyl)-9-methyl-6a,7,8,9,10,10a-hexahydro-6H-benzo[c]chromen-2-ol and (6aR,6S,9R,10aS)-6-(4-Hydroxy-phenyl)-9-methyl-6a,7,8910,10a-hexahydro-6H-benzo[c]chromen-2-ol

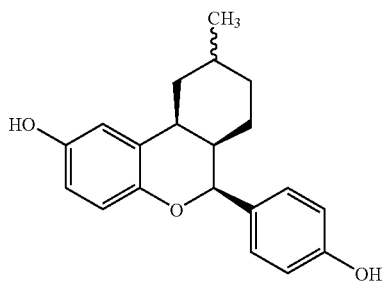

(6aR,6S,9S,10aS)-6-(4-Hydroxy-phenyl)-9-methyl-6a,7,8,9,10,10a-hexahydro-6H-benzo[c]chromen-2-ol and (6aR,6S,9R,10aS)-6-(4-Hydroxy-phenyl)-9-methyl-6a,7,8,9,10,10a-hexahydro-6H-benzo[c]chromen-2-ol To a mixture of 10 wt % Pd on carbon (0.03 g) in MeOH (20 mL) add a solution of Example 22 (0.022 g, 0.07 mmol) in MeOH (2 mL). Maintain the solution under 60 psi of H₂ (g) for 4 h. Filter the solution and concentrate the filtrate to afford Example 21 (0.022 g crude, 100%) as 3:1 ratio of epimers as a white solid. Major diastereomer: ¹H NMR (CD₃OD) δ 7.22 (d, J=8.4 Hz, 2H), 6.81 (d, J=2.4 Hz, 1H), 6.78 (d, J=8.4 Hz, 2H), 6.68 (d, J=8.8 Hz, 1H), 6.54 (dd, J=8.8, 2.4 Hz, 1H), 4.94 (s, 1H), 3.30 (m, 1H), 2.23 (d, J=13.6 Hz, 1H), 1.95 (m, 2H), 1.33-1.56 (m, 3H), 1.20 (m, 1H), 1.11 (m, 1H), 0.63 (d, J=7.2 Hz, 3H).

Preparation 37

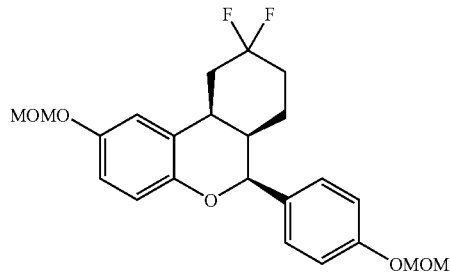

9,9-Difluoro-2-methoxymethoxy-6-(4-methoxymethoxy-phenyl)-6a,7,8,9,10,10a-hexahydro-6H-benzo[c]chromene Heat a mixture of Preparation 35 (0.102 g, 0.26 mmol) and (Diethylamino) sulfur trifluoride (0.25 mL) in 1,2-dichloroethane (0.75 mL) to 40 C for 12 h. Purify the mixture by MPLC (0% to 10% to 25% EtOAc/hexanes) to afford Preparation 37 (0.042 g, 39%). ¹H NMR (CDCl₃) δ 7.35 (d, J=8.8 Hz, 2H), 7.08 (d, J=8.8 Hz, 2H), 7.02 (s, 1H), 6.86 (m, 2H), 5.20 (s, 2H), 5.16 (s, 1H), 5.15 (A of AB, J_{AB}=6.4 Hz, 1H), 5.11 (B of AB, J_{AB}=6.4 Hz, 1H), 3.66 (br s, 1H), 3.50 (s, 6H), 2.84 (m, 1H), 1.96-2.23 (m, 3H), 1.54-1.69 (m, 2H), 1.44 (m, 1H).

Example 22

Preparation of (6aR,6S,10aS)-9,9-Difluoro-6-(4-hydroxy-phenyl)-6a,7,8,9,10,10a-hexahydro-6H-benzo[c]chromen-2-ol

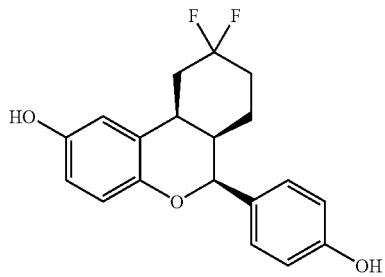

(6aR,6S,10aS)-9,9-Difluoro-6-(4-hydroxy-phenyl)-6a,7,8,9,10,10a-hexahydro-6H-benzo[c]chromen-2-ol Add a solution of HCl (2 mL, 3 N in H₂O) to Preparation 37 (0.042 g, 0.10 mmol) in THF (5 mL) and H₂O (1 mL) and stir the mixture for 12 h. Pour the mixture into satd. NaHCO₃ and extract with Et₂O (2×50 mL) and EtOAc (2×50 mL). Wash the combined organic extracts with brine, dry over Na₂SO₄, and concentrate to afford the desired product as a light yellow solid. Purify the crude material by MPLC (0% to 25% to 40%

EtOAc/hexanes) to afford Example 22 (0.014 g, 37%) as a yellow oil. ¹H NMR (CD₃OD) δ 7.25 (d, J=8.4 Hz, 2H), 6.80 (d, J=8.4 Hz, 2H), 6.79 (d, J=2.4 Hz, 1H), 6.69 (d, J=8.4 Hz, 1H), 6.56 (dd, J=2.4 Hz, 1H), 5.07 (s, 1H), 3.62 (br s, 1H), 2.77 (m, 1H), 2.09-2.28 (m, 2H), 1.90 (m, 1H), 1.47-1.65 (m, 2H), 1.36 (m, 1H).

Preparation 38

4-Allyl-6-benzyloxy-2-oxo-chroman-3-carboxylic acid ethyl ester

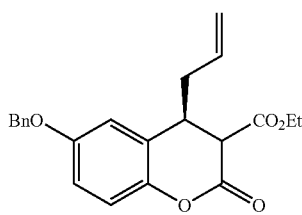

To a 0 C solution of Preparation 27 (10.0 g, 30.8 mmol) in THF (125 mL) add a solution of allyl magnesium chloride in Et₂O (46 mL, 1.0 M, 46 mmol). Maintain the reaction at 0 C for 30 min, then pour the reaction contents into a solution of ½ satd. NaHCO₃ (250 mL). Extract the solution with Et₂O (2×150 mL) and EtOAc (150 mL). Wash the combined organic extracts with H₂O (150 mL) and brine (150 mL), dry the organics over Na₂SO₄, and concentrate to afford a brown oil. Purify the product by MPLC (0% to 15% to 25% EtOAc/hexanes) to afford Preparation 38 (7.72 g, 68%) as a light yellow solid. ¹H NMR (CDCl₃) δ 7.31-7.43 (m, 5H), 7.01 (d, J=8.8 Hz, 1H), 6.87 (dd, J=8.8, 3.0 Hz, 1H), 6.79 (d, J=3.0 Hz, 1H), 5.71 (m, 1H), 5.15 (dd, J=0.8, 9.8 Hz, 1H), 5.10 (dd, J=0.8, 17.6 Hz, 1H), 5.04 (A of AB, J$_{AB}$=14.2 Hz, 1H), 5.03 (B of AB, J$_{AB}$=14.2 Hz, 1H), 4.08 (m, 2H), 3.80 (d, J=2.4 Hz, 1H), 3.41 (m, 1H), 2.35 (m, 2H), 1.08 (t, J=7.2 Hz, 3H).

Preparation 39

4-Allyl-6-benzyloxy-chroman-2-one

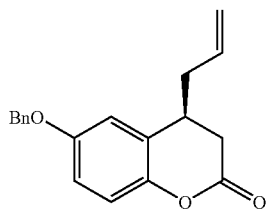

Heat a solution of Preparation 38 (4.8 g, 13.1 mmol) and LiOH (6 g) in a solution of THF (75 mL), EtOH (30 mL), MeOH (20 mL), and H₂O (50 mL) to 60 C for 2 h. Pour the contents into 1 N HCl (250 mL) and extract the mixture with Et₂O (2×200 mL) and EtOAc (2×150 mL). Wash the combined organic extracts with brine (200 mL), dry over Na₂SO₄, and concentrate to afford the crude β-keto acid.

Heat a solution of the crude acid in o-xylenes to reflux for 1.5 h. Remove the solvent in vacuo, and purify the lactone by MPLC (0% to 12% to 20% EtOAc/hexanes) to afford Preparation 39 (3.5 g, 91%) as a white solid. ¹H NMR (CDCl₃) δ 7.31-7.44 (m, 5H), 6.99 (d, J=8.8 Hz, 1H), 6.86 (dd, J=8.8, 3.2 Hz, 1H), 6.81 (d, J=3.2 Hz, 1H), 5.72 (m, 1H), 5.07-5.14 (m, 2H), 5.05 (s, 2H), 3.03 (m, 1H), 2.76 (t, J=8.8 Hz, 2H), 2.43 (m, 1H), 2.30 (m, 1H).

Preparation 40

4-Allyl-6-benzyloxy-3-(2-methoxymethoxy-allyl)-chroman-2-one

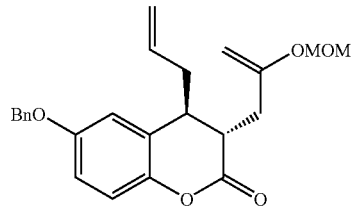

Cool a solution of Preparation 39 (3.65 g, 12.4 mmol) in THF (90 mL) to −78 C. Add a solution of KHMDS (32 mL, 0.5 M in toluene, 16 mmoL) over 5 min, then allow to stir for 15 in at −78 C. Add hexamethylphosphoramide (HMPA) via syringe (2.8 mL, 16.1 mmoL) quickly, and allow to stir for 20 min at −78 C. Add 2-O-methoxylmethyl allyl iodide (4.24 g) over 2 min, and then allow the solution to warm to −50 C over 1.5 h. Pour the contents of the reaction into ½ satd. NaHCO₃ and extract with Et₂O (2×100 mL) and EtOAc (2×100 mL). Wash the combined organic extracts with H₂O (2×150 mL) and brine (150 mL) and then dry over Na₂SO₄—Concentrate the crude product to leave a brown oil, which is purified by MPLC (0% to 12% to 20% EtOAc/hexanes) to afford Preparation 40 (3.72 g, 76%) as a light yellow oil. ¹H NMR (CDCl₃) δ 7.31-7.44 (m, 5H), 6.98 (d, J=8.8 Hz, 1H), 6.87 (dd, J=8.8, 3.2 Hz, 1H), 6.74 (d, J=3.2 Hz, 1H), 5.66 (m, 1H), 5.01-5.09 (m, 4H), 4.93 (A ob AB, J$_{AB}$=6.4 Hz, 1H), 4.90 (B of AB, J$_{AB}$=6.4 Hz, 1H), 4.18 (d, J=2.4 Hz, 1H), 3.87 (d, J=2.4 Hz, 1H), 3.44 (s, 3H), 3.18 (m, 1H), 2.86 (m, 1H), 2.22-2.39 (m, 3H), 2.12 (dd, J=9.4, 14.0 Hz, 1H).

Preparation 41

2-Benzyloxy-8-methoxymethoxy-6a,7,10,10a-tetrahydro-benzo[c]chromen-6-one

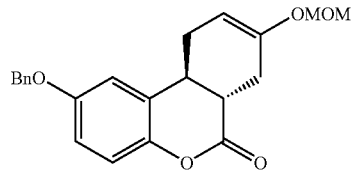

Bubble N2 gas through a solution of Preparation 40 (1.0 g, 2.54 mmol) in CH₂Cl₂ (250 mL) equipped with a reflux condenser for 30 min. Add [1,3-bis-(2,4,6-trimethylphenyl)-2-imidazolidinylidene)dichloro(phenylmethylene)-tricyclohexylphosphine)ruthenium] (0.212 g, 0.25 mmol) and heat the reaction to reflux for 2.5 h. Allow the reaction to cool to room temperature, remove the condenser, and bubble air through the mixture for 10 min. Remove the solvent in vacuo, and purify the residue by MPLC (0% to 12% to 25% EtOAc/hexanes) to afford Preparation 41 (0.72 gm, 78%) as a clear oil. ¹H NMR (CDCl₃) δ 7.32-7.45 (m, 5H), 7.00 (d, J=8.4 Hz, 1H), 6.86 (m, 2H), 5.05 (m, 3H), 5.00 (A of AB, J$_{AB}$=6.4 Hz, 1H), 4.97 (B of AB, J$_{AB}$=6.4 Hz, 1H), 3.45 (s, 3H), 2.94 (m, 1H), 2.83 (m, 1H), 2.56-2.70 (m, 3H), 2.25 (m, 1H).

Preparation 42

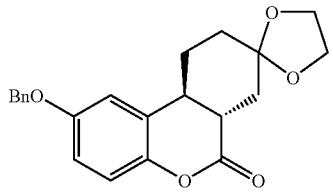

Treat a solution of Preparation 41 (0.72 g, 1.97 mmol) in THF (40 mL) with 3 N HCl (3 mL) for 4 h. Pour the contents into H₂O and extract with Et₂O and EtOAc. Wash the combined organic extracts with satd. NaHCO₃ and brine, dry the combined extracts over Na₂SO₄, and concentrate to afford the crude intermediate ketone. Dissolve the ketone in toluene (40 mL) and add p-toluenesulfonic acid monohydrate (0.038 g), then attach a Dean Stark apparatus and heat the reaction to reflux for 2.5 h. Pour the contents into ½ satd. NaHCO₃ (50 mL) and separate the layers. Further extract the aqueous layer with Et₂O and EtOAc (50 mL each). Wash the combined organic extracts with brine (50 mL), dry the combined organics over Na2SO4, and concentrate to afford Preparation 42 (0.74 g, 100%) as a white solid. ¹H NMR (CDCl₃) δ 7.31-7.44 (m, 5H), 6.98 (d, J=8.4 Hz, 1H), 6.86 (m, 2H), 5.04 (s, 2H), 4.03 (m, 2H), 3.94 (m, 2H), 2.71 (m, 1H), 2.55 (m, 1H), 2.35-2.46 (m, 2H), 1.92 (m, 1H), 1.67-1.79 (m, 3H).

Preparation 43

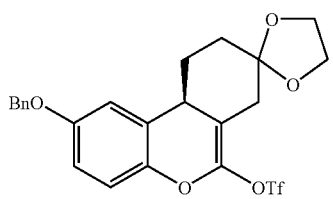

To a –78 C solution of Preparation 42 (0.366 g, 1.0 mmol) in THF (8 mL) add a solution of LDA (1.13 mL, 1.5 M cyclohexane, 1.7 mmol). Stir at –78 C for 15 min, then add HMPA (0.59 mL, 3.4 mmoL) and warm to –50 C. Stir for 15 min, then recool the solution to –78 C. Add a solution of N-phenyl triflamide (0.607 g, 1.7 mmol) in THF (2 mL) dropwise, and stir the resulting solution for 30 min. Pour the reaction contents into ½ satd. NaHCO₃, and extract the mixture with Et₂O (2×30 mL) and EtOAc (40 mL). Wash the combined organic extracts with H₂O (2×50 mL) and brine (50 mL), dry the organic layer over Na₂SO₄, and concentrate to afford the crude product. Purify the material by MPLC (0% to 15% to 25% EtOAc/hexanes) to afford Preparation 43 (0.059 g, 12%) as a yellow oil. ¹H NMR (CDCl₃) δ 7.28-7.43 (m, 5H), 6.81 (m, 2H), 6.75 (d, J=2.4 Hz, 1H), 5.02 (s, 2H), 3.99 (m, 4H), 3.51 (q, J=5.2 Hz, 1H), 2.73 (dd, J=2.8, 14.0 Hz, 1H), 2.17 (m, 2H), 1.83-1.97 (m, 3H).

Preparation 44

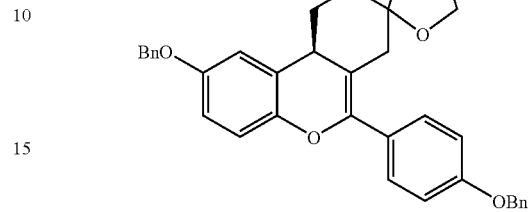

Sparge N₂ (g) through a solution of Preparation 43 (0.059 g, 0.12 mmol), p-benzyloxyphenylboronic acid (0.038 g, 0.165 mmol), and LiCl (0.025 g, 0.60 mmol) in DME (2.5 mL) and aqueous Na₂CO₃ (0.25 mL, 2 M in H₂O, 0.5 mmol) for 15 min. Add palladium tetrakis triphenylphosphine (0.035 g, 0.03 mmoL) and heat the solution to reflux for 24 h. Allow the solution to cool to 23 C, then pour the reaction contents into ½ satd NaHCO₃, and extract with EtOAc (3×25 mL). Combine the organic extracts and wash with brine (25 mL), then dry over Na₂SO₄ and concentrate. Purify the residue by MPLC (0% to 12% to 25% EtOAc/hexanes) to afford Preparation 44 (0.024 g, 38%) as a clear oil. ¹H NMR (CDCl₃) δ 7.31-7.47 (m, 10H), 7.01 (d, J=8.8 Hz, 2H), 6.86 (d, J=8.8 Hz, 2H), 6.79 (s, 1H), 6.75 (d, J=8.8 Hz, 2H), 5.11 (s, 2H), 5.04 (s, 2H), 3.97 (m, 4H), 3.43 (m, 1H), 2.64 (dd, J=2.8, 14.0 Hz, 1H), 2.20 (m, 1H), 2.13 (m, 1H), 1.99 (m, 1H), 1.91 (m, 2H).

Preparation 45

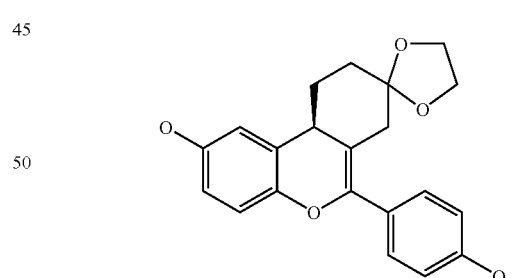

To a mixture of 10 wt % Pd on carbon (0.02 g) in MeOH (25 mL) add a solution of Preparation 44 (0.020 g, 0.04 mmol) in THF (10 mL). Maintain the solution under 60 psi of H₂ (g) for 4 h. Filter the solution and concentrate the filtrate to afford Preparation 45 (0.012 g crude, ~quantitative) as a white solid. TLC R$_f$ 0.4, 60% EtOAc/hexanes.

Example 23

Preparation of (6aR,6S,10aS)-2-Hydroxy-6-(4-hydroxy-phenyl)-6a,9,10,10a-tetrahydro-6H,7H-benzo[c]chromen-8-one

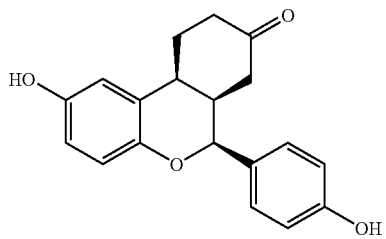

(6aR,6S,10aS)-2-Hydroxy-6-(4-hydroxy-phenyl)-6a,9,10,10a-tetrahydro-6H,7H-benzo[c]chromen-8-one To a solution of Preparation 45 (0.012 g) in THF (20 mL) and H$_2$O (1 mL) add HCl solution (2 mL, 3 N in H$_2$O), and stir the mixture overnight. Pour the mixture into satd. NaHCO$_3$ and extract with Et$_2$O (2×50 mL) and EtOAc (2×50 mL). Wash the combined organic extracts with brine, dry over Na$_2$SO$_4$, and concentrate to afford crude Preparation 27 as a light yellow solid. Purify the crude material by MPLC (0% to 25% to 50% EtOAc/hexanes) to afford Example 23 (0.010 g, 90%) as a white solid. $^1$H NMR (CD$_3$OD) δ 7.22 (d, J=8.0 Hz, 2H), 6.85 (m, 1H), 6.79 (m, 3H), 6.64 (m, 1H), 5.22 (s, 1H), 3.54 (m, 1H), 2.67 (m, 1H), 2.56 (m, 1H), 2.26 (m, 2H), 2.13 (m, 2H), 1.84 (dd, J=3.9, 14.5 Hz, 1H).

Preparation 46

6-Benzyloxy-chromen-2-one

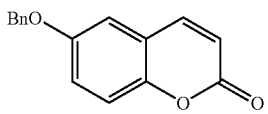

Equip a 5-L, three-neck, round-bottom flask with a large blade mechanical stirrer, thermocouple, an addition funnel, Claisen adapter, reflux condenser, and a sodium hydroxide scrubber. Charge the flask with 2,5-dimethoxycinnamic acid (182.3 g, 865 mmol, 1.0 equiv) and dichloroethane (2.5 L). Add boron tribromide (163.5 mL, 433.2 g, 1.73 mol, 2.0 equiv.) dropwise over 1 h, keeping the temperature below 35° C. Gas evolution can be monitored as the temperature of the reaction is gradually increased to reflux (82° C.). Reflux for 12 h, cool to 5° C., and quench by the careful addition of water (1.0 L). Filter the resulting yellow-red suspension/emulsion through a glass frit and wash with dichloroethane (1.0 L) and heptane (1.0 L) to afford a brown solid. Dry the wet material in a vacuum oven (30 in., 35° C.) for 18 h, to afford the coumarin (180.3 g, 127% theory) as a brown solid: $^1$H NMR (300 MHz, DMSO-d$_6$) δ 7.97 (d, J=9.6 Hz, 1H), 7.22 (d, J=9.9 Hz, 1H), 7.05 (m, 2H), 6.43 (d, J=9.6 Hz, 1H).

Equip a 5-L, three-neck, round-bottom flask with a mechanical stirrer, thermocouple, an addition funnel, and an inlet adapter. Charge the flask with the coumarin prepared above (360.0 g, 2.20 mol, 1.0 equiv) and N,N-dimethylformamide (2.2 L). While keeping the temperature below 30° C., add cesium carbonate [904.2 g, 2.78 mol, 1.25 equiv]. Then add benzyl bromide [475.5 g, 330.2 mL, 2.78 mol, 1.25 equiv] over a period of 1 h, keeping the temperature below 35° C. during the addition. Stir the mixture at ambient temperature (25-30° C.) for 10.5 h. Pour the reaction mixture into ice water (4.5 L), filter, and dry at ambient pressure for 72 h, triturate in heptane (1.5 L) with vigorous stirring, filter, and dry under reduced pressure (30 in., 35° C.) to afford preparation 46 (302.4 g, 1.20 mol, 60%) as a light brown solid: $^1$H NMR (300 MHz, DMSO-d$_6$) δ 7.99 (d, J=9.6 Hz, 1H), 7.50-7.29 (m, 8H), 6.49 (d, J=9.5 Hz, 1H), 5.15 (s, 2H); $^{13}$C NMR (75 MHz, DMSO-d$_6$) δ 160.0, 154.6, 147.9, 143.9, 136.6, 128.4, 127.9, 127.7, 119.9, 119.1, 117.3, 116.6, 111.9, 69.8; IR (KBr) 3052 (w), 1708 (s), 1568 (m), 1492 (w), 1444 (w), 1383 (w), 1272 (m), 1168 (w), 1110 (m), 1020 (m), 927 (w), 814 (w), 762 (w), 709 (w) cm$^{-1}$; HPLC analysis 95.9% (AUC), Phenomenex Luna C18(2) column; ESI MS m/z 253 [C$_{16}$H$_{12}$O$_3$+H]$^+$

Preparation 47

8-Benzyloxy-2-methylene-2,3,3a,9b-tetrahydro-1H-cyclopenta[c]chromen-4-one

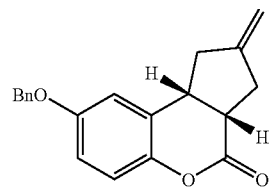

Starting from preparation 46 this compound can be prepared in a manner substantially similar to that described in preparation 13. $^1$H NMR (400 MHz, CDCl$_3$) δ 7.44-7.32 (m, 5H), 6.98 (d, J=8.8 Hz, 1H), 6.86 (dd, J=3.1, 8.8 Hz, 1H), 6.82 (d, J=3.1 Hz, 1H), 5.04 (s, 2H), 4.98-4.95 (m, 2H), 3.40 (dt, J=7.5, 16.3 Hz, 1H), 3.15 (ddd, J=4.4, 7.9, 11.9 1H), 3.06-3.01 (m, 1H), 2.82-2.72 (m, 2H), 2.47-2.40 (m, 1H).

Preparation 48

8-Benzyloxy-4-(4-benzyloxy-phenyl)-2-methylene-1,2,3,9b-tetrahydro-cyclopenta[c]chromene

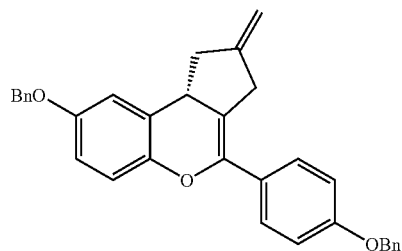

Add p-benzyloxybromobenzene (20 g, 76 mmol) to magnesium metal (1.85 g, 76 mmol). Flush with nitrogen and add 76 mL of THF followed by a small crystal of I$_2$. Heat to reflux to initiate Grignard formation and then let stir at room temperature overnight. Add the resulting aryl Grignard via cannula to a solution of ZnCl$_2$ (76 mL of a 1 M solution in Et$_2$O, 76 mmol) in 152 mL of THF. Stir for 30 min and then let the precipitate settle to give a solution of the aryl zinc.

Cool a solution of preparation 47 (9.43 g, 30.8 mmol) in 312 mL of THF to −78° C. Add KHMDS (74 mL of a 0.5 M solution in toluene, 37 mmol). Stir for 20 min. Add via cannula a solution of N-phenyl bis(trifluoromethanesulphonamide) (13.22 g, 37 mmol) in 47 mL of THF. Stir for 2 hrs and then quench with saturated aqueous NH$_4$Cl. Partition the solution between 250 mL of 1:1 water:brine and 250 mL of EtOAc. Separate and wash the organic solution with brine, dry over Na$_2$SO$_4$, filter, and concentrate. Adsorb the material to silica gel and purify by silica gel chromatography eluting with a linear gradient of 0-100% CH$_2$Cl$_2$ in hexanes to afford 9.77 g (22.3 mmol, 72%) of the enol triflate of preparation 46.

Add via cannula the solution of the aryl zinc described above to a solution of the enol triflate described above and Pd(PPh$_3$) (2.57 g, 2.22 mmol) in 36 mL of THF under N$_2$. Heat the solution to 50° C. for 30 min. Cool the solution to room temperature and quench with saturated aqueous sodium bicarbonate and extract with EtOAc. Wash the combined organic solutions with brine, dry over Na$_2$SO$_4$, filter and concentrate. To remove the catalyst, dissolve the residue in 1:1 hexanes:CH$_2$Cl$_2$ and filter through celite. Further purify the product by filtration through silica gel using 1:1 hexanes: CH$_2$Cl$_2$-Further purify by re-crystallization from EtOAc and hexanes to afford 5.96 g (12.6 mmol, 57%) of preparation 48. $^1$H NMR (400 MHz, CDCl$_3$) δ 7.58-7.38 (m, 12H), 7.06-7.03 (m, 3H), 6.87 (dd, J=2.6, 8.8 Hz, 1H), 6.79 (d, J=3.1 Hz, 1H), 5.15 (s, 2H), 5.09 (s, 2H), 5.06 (s, 1H), 5.00 (s, 1H), 3.95 (t, J=9.7 Hz, 1H), 3.48 (d, J=20 Hz, 1H), 3.33 (d, J=20 Hz, 1H), 3.12 (dd, J=8.4, 15.4 Hz, 1H), 2.50 (t, J=12.8 Hz, 1H).

Preparation 49

8-Benzyloxy-4-(4-benzyloxy-phenyl)-2-methylene-1,2,3,3a,4,9b-hexahydro-cyclopenta [c]chromene

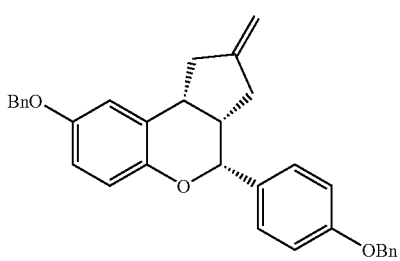

Add TFA (3.2 mL, 41.6 mmol) to a solution of preparation 48 (5.94 g, 12.6 mmol) and Et$_3$SiH (20.1 mL, 126 mmol) in 101 mL of CH$_2$Cl$_2$ at 0° C. Stir for 5 min and then pour into a solution of saturated aqueous sodium bicarbonate. Wash the organic solution two times with saturated aqueous sodium bicarbonate, dry over Na$_2$SO$_4$, filter, and concentrate. Purify the product by silica gel chromatography eluting with 10-60% CH$_2$Cl$_2$ in hexanes to afford 3.67 g (7.73 mmol, 62%) of preparation 49. $^1$H NMR (400 MHz, CDCl$_3$) δ 7.50-7.35 (m, 12H), 7.29-7.02 (m, 2H), 6.88 (d, J=9.2 Hz, 1H), 6.83-6.79 (m, 2H), 5.14 (d, J=1.8 Hz, 1H), 5.12 (s, 2H), 5.05 (s, 2H), 4.78 (m, 2H), 3.60 (t, J=7.5 Hz, 1H), 2.92 (m, 1H), 2.73 (m, 1H), 2.65 (d, J=16.7 Hz, 1H), 2.46 (m, 1H), 2.13 (dd, J=7.9, 16.7 Hz, 1H).

Preparation 50

8-Benzyloxy-4-(4-benzyloxy-phenyl)-1,3a,4,9b-tetrahydro-3H-cyclopenta [c]chromen-2-one

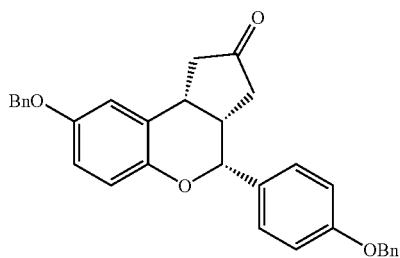

Add osmium tetroxide (4.8 mL of a 2.5 wt % solution in t-BuOH, 0.38 mmol) to a solution of preparation 49 (3.62 g, 7.63 mmol), N-methylmorpholine (0.84 mL, 7.6 mmol), and N-methylmorpholine-N-oxide (1.79 g, 15.3 mmol) in 55 mL of THF and 21 mL of water. Stir for 6.5 hrs and then add 88 mL of THF, 106 mL of water and sodium periodate (8.16 g, 38.2 mmol). Stir overnight. Quench with an 1:1 solution of saturated aqueous Na$_2$SO$_3$ and saturated aqueous NaHCO$_3$. Separate the organic solution and wash with brine, dry over Na$_2$SO$_4$, filter and concentrate. Dissolve in 1:1 EtOAc: CH$_2$Cl$_2$ and wash with water, dry over Na$_2$SO$_4$, filter and concentrate to afford 3.35 g (7.03 mmol, 92%) of preparation 50. $^1$H NMR (400 MHz, CDCl$_3$) δ 7.49-7.34 (m, 12H), 7.04-7.02 (m, 2H), 6.92 (d, J=8.8 Hz, 1H), 6.85 (dd, J=2.6, 8.8 Hz, 1H), 6.77 (d, J=2.6H), 5.16 (s, 1H), 5.12 (s, 2H), 5.04 (s, 2H), 3.90 (t, J=7.5 Hz, 1H), 2.96 (dt, J=3.0, 13.7 Hz, 1H), 2.80 (dd, J=8.4, 18.5 Hz, 1H), 2.63 (d, J=18.1 Hz, 1H), 2.37 (dd, J=11.9, 18.9 Hz, 1H), 2.08 (dd, J=7.9, 18.5 Hz, 1H).

Preparation 51

8-benzyloxy-4-(4-benzyloxy-phenyl)-1,2,3,3a,4,9b-hexahydro-cyclopenta[c]chromen-2-ol

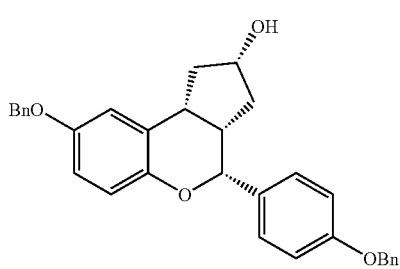

Add sodium borohydride (240 mg, 6.3 mmol) to a solution of preparation 50 (1.5 g, 3.15 mmol) in 30 mL of THF and 30 mL of methanol. Let stir for 30 min. Quench with saturated aqueous ammonium chloride, separate, back extract the aqueous solution two times with EtOAc. Combine the organic solutions and wash with 1:1 brine:water, dry over Na$_2$SO$_4$, filter, and concentrate to give 1.5 g (3.13 mmol, 99%) of preparation 51. $^1$H NMR (400 MHz, CDCl$_3$): δ 7.56-7.33 (m, 12H), 7.05-7.01 (m, 2H), 6.92 (d, J=8.8 Hz, 1H), 6.83-6.80 (m, 2H), 5.12 (s, 2H), 5.07 (s, 1H), 5.06 (s, 2H), 4.27 (d, J=6.6, 11.0 Hz, 1H), 3.53 (m, 1H), 2.63 (m, 1H), 2.51 (dt, J=7.5, 13.6 Hz, 1H), 1.92-1.86 (m, 2H), 1.72 (dddd, J=6.6, 11.0, 13.6, 17.1 Hz, 1H). HRMS (ES+) calc: 496.2488; found: 496.2485 [M+NH$_4$]$^+$.

Preparation 52

8-Benzyloxy-4-(4-benzyloxy-phenyl)-1,2,3,3a,4,9b-hexahydro-cyclopenta[c]chromene-2-carbonitrile

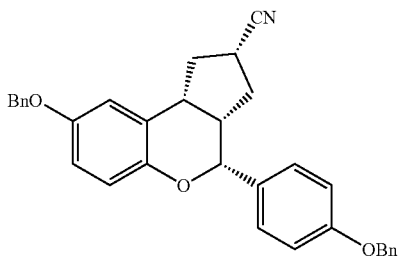

To a solution of preparation 51 (50 mg, 0.104 mmol), acetone cyanohydrin (48 µL, 0.52 mmol), and triphenyl phosphine (137 mg, 0.52 mmol), in 2.5 mL of THF at 0° C. add diisopropylazodicarboxylate (103 µL, 0.52 mmol). Stir the solution and allow it to warm slowly to room temperature overnight. Add 1 g of silica gel and concentrate. Purify by silica gel chromatography eluting with 10-30% EtOAc in hexanes to afford 30 mg (0.62 mmol, 59%) of preparation 52. $^1$H NMR (400 MHz, CDCl$_3$): δ 7.63-7.33 (m, 12H), 7.06-7.02 (m, 2H), 6.90 (d, J=8.8 Hz, 1H), 6.83 (dd, J=3.1, 8.8 Hz, 1H), 6.77 (d, J=3.1 Hz, 1H), 5.13 (s, 2H), 5.07 (d, J=2.2 Hz, 1H), 5.06 (s, 2H), 3.70 (t, J=6.6 Hz, 1H), 2.97 (ddt, J=2.2, 9.2, 18.9 Hz, 1H), 2.68 (m, 1H), 2.43 (m, 1H), 2.28 (ddd, J=1.8, 7.0, 8.8 Hz, 1H), 2.15 (dt, J=9.2, 13.6 Hz, 1H), 1.80 (ddd, J=6.2, 9.3, 13.6 Hz, 1H); HRMS (FAB) calcd. for C$_{33}$H$_{29}$NO$_3$: 487.2147; found: 487.2124 (M+).

Example 24

(2R,3aR,4S,9bS)- and (2S,3aS,4R,9bR)-8-Hydroxy-4-(4-hydroxy-phenyl)-1,2,3,3a,4,9b-hexahydro-cyclopenta[c]chromene-2-carbonitrile

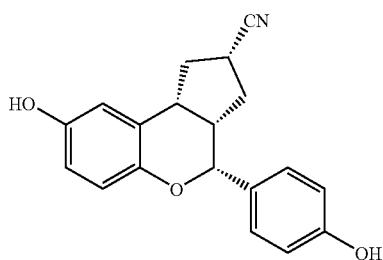

Dissolve preparation 52 (24 mg, 0.050 mmol) in 1 mL of THF. Add a slurry of 10% Pd/C (10 mg) in 1 mL of iPrOH. Add another 1 mL of THF, warm to redissolve preparation 52, then stir under an atmosphere of hydrogen gas at ambient pressure for 6 hrs. Filter the solution through a 0.2 µm HPLC filter, wash with methanol and concentrate. Purify by silica gel chromatography eluting with 5-50% (9:1 EtOAc:MeOH) in hexanes to afford 11.2 mg (0.036, 73%) of example 26. $^1$H NMR (400 MHz, CDCl$_3$): δ 7.32-7.30 (m, 2H), 6.85-6.82 (m, 2H), 6.76 (d, J=8.4 Hz, 1H), 6.65 (d, J=2.6 Hz, 1H), 6.61 (dd, J=3.0, 8.7 Hz, 1H), 5.00 (d, J=2.5 Hz, 1H), 3.67 (t, J=6.6 Hz, 1H), 2.99 (dt, J=2.2, 9.7 Hz, 1H), 2.72 (ddd, J=7.0, 9.7, 13.6 Hz, 1H), 2.41 (ddd, J=7.0, 9.7, 12.7 Hz, 1H), 2.29 (ddd, J=1.6, 6.6, 8.8 Hz, 1H), 2.11 (ddd, J=9.2, 13.6, 18.0 Hz, 1H), 1.68 (ddd, J=6.6, 9.2, 13.2 Hz, 1H). HPLC (Zorbax C18 column; 10 to 100% CH$_3$CN/H$_2$O for 10 min then 100% CH$_3$CN for 5 min; 1 mL/min; t$_r$ 9.064 min). HRMS (ES−) calcd. for C$_{19}$H$_{16}$NO$_3$: 306.1130; found: 306.1155 (M−1).

Preparation 53

8-Benzyloxy-4-(4-benzyloxy-phenyl)-1,2,3,3a,4,9b-hexahydro-cyclopenta[c]chromene-2-carbonitrile

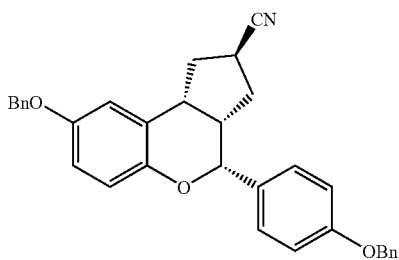

Place preparation 51 (0.2619 g, 0.5472 mmol) and triphenylphosphine (0.29 g, 1.1 mmol) in a flask and flush with N$_2$. Add THF (5.5 mL) and p-nitrobenzoic acid (0.27 g 1.6 mmol) and cool to 0° C. Add diisopropylazodicarboxylate (0.22 mL, 1.1 mmol) dropwise to the reaction mixture keeping it below 5° C. Let the reaction mixture warm slowly to room temperature overnight. Dilute the solution with EtOAc (100 mL), wash with saturated aqueous sodium bicarbonate (2×50 mL), brine (50 mL), dry over Na$_2$SO$_4$, filter and concentrate. Purify by silica gel chromatography (10-25% of 9:1 CH$_2$Cl$_2$:EtOAc in hexanes over 30 min) to afford 0.1876 g (0.2989 mmol, 55%) of a yellow solid. $^1$H NMR (400 MHz, CDCl$_3$): δ 8.30 (d, 2H, J=8.8 Hz), 8.71 (d, 2H, J=8.8 Hz), 7.35-7.49 (m, 10H), 7.41 (d, 2H, J=8.8 Hz), 7.03 (d, 2H, J=8.4 Hz), 6.91 (d, 1H, J=8.8 Hz), 6.81-6.85 (m, 2H), 5.41 (m, 1H), 5.14 (m, 1H), 5.11 (s, 2H), 5.06 (s, 2H), 3.74-3.77 (m, 1H), 2.95-3.02 (m, 1H), 2.49-2.55 (m, 1H), 2.36-2.42 (m, 1H), 2.16-2.24 (m, 1H), 1.73 (dd, 1H, J=7.5 Hz, J=14 Hz). HRMS (CI+) calcd. for C$_{39}$H$_{33}$NO$_7$: 627.2257; found: 627.2263 (M+).

Dissolve the yellow solid (0.1839 g, 0.2930 mmol) in 2.9 mL of THF and add an aqueous solution of LiOH (0.035 g, 1.5 mmol) in 1.1 mL of water. Stir at room temperature overnight. Add 1.0 M aqueous NaH$_2$PO$_4$ (1.5 mL, 1.5 mmol). Dilute with EtOAc (100 mL), wash with saturated aqueous NaHCO$_3$ (2×50 mL), wash with brine (50 mL), dry over Na$_2$SO$_4$, filter and concentrate to afford a white solid (0.1398 g, 0.2921 mmol, 99%). $^1$H NMR (400 MHz, CDCl$_3$): δ 7.36-7.49 (m, 12H), 7.03 (d, 2H, J=8.8 Hz), 6.87-6.89 (m, 1H), 6.78-6.80 (m, 2H), 5.12 (s, 2H), 5.10-5.11 (m, 1H), 5.05 (s, 2H), 4.34 (m, 1H), 3.65-3.70 (m, 1H), 2.98-3.06 (m, 1H), 2.26-2.32 (m, 1H), 2.04-2.10 (m, 1H), 1.87-1.95 (m, 1H), 1.44 (dd, 1H, J=7.9 Hz, J=14 Hz), 1.30 (m, 1H). HRMS (CI+) calcd. for C$_{32}$H$_{30}$O$_4$: 478.2144; found: 478.2154 (M+).

Dissolve the white solid (0.1092 g, 0.2282 mmol) and PPh$_3$ (0.30 g, 1.1 mmol) in THF (5.5 mL). Add acetone cyanohydrin (0.42 mL, 4.6 mmol) and cool to 0° C. Add diisopropyl azodicarboxylate (0.22 mL, 1.1 mmol) dropwise keeping the solution below 5° C. Let the solution warm slowly to room temperature overnight. Add silica gel and concentrate. Purify by silica gel chromatography eluting with $CH_2Cl_2$ in EtOAc to afford 0.0432 g (0.0886 mmol, 39%) of preparation 53. $^1H$ NMR (400 MHz, $CDCl_3$): δ 7.35-7.50 (m, 12H), 7.04 (d, 2H, J=8.8 Hz), 6.92 (d, 1H, J=8.8 Hz), 6.84 (dd, 1H, J=8.8 Hz, J=3.1 Hz), 6.76 (d, 1H, J=3.1 Hz), 5.13 (s, 2H), 5.06 (s, 2H), 5.05 (m, 1H), 3.59-3.65 (m, 1H), 2.70-2.80 (m, 2H), 2.59-2.67 (m, 1H), 2.00-2.10 (m, 2H), 1.84-1.91 (m, 1H). HRMS calcd. for $C_{33}H_{29}NO_3$: 487.2147; found: 487.2134 (M+).

Example 25

(2S,3aR,4S,9bS)- and (2R,3aS,4R,9bR)-8-Hydroxy-4-(4-hydroxy-phenyl)-1,2,3,3a,4,9b-hexahydro-cyclopenta[c]chromene-2-carbonitrile

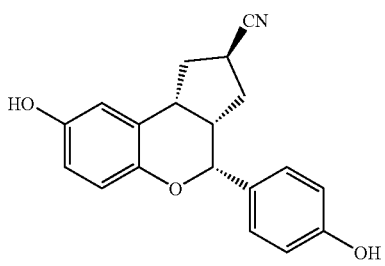

Example 27 can be prepared in a manner substantially similar to Example 26 except starting from Preparation 53. The hydrogenation is carried out under a 60 psi atmosphere of hydrogen for several days. $^1H$ NMR (δ, 400 MHz, $CDCl_3$): 7.30 (d, 2H, J=8.4 Hz), 6.83 (d, 2H, J=8.8 Hz), 6.78 (d, 2H, J=8.8 Hz), 6.64-6.56 (m, 1H), 6.62 (dd, 1H, J=8.4, 2.6 Hz), 4.99 (m, 1H), 3.55-3.62 (m, 1H), 2.90-3.00 (m, 1H), 2.67-2.76 (m, 2H), 1.94-2.04 (m, 2H), 1.78-1.94 (m, 2H). HPLC (Zorbax C18 column; 10 to 100% $CH_3CN/H_2O$ for 10 min then 100% $CH_3CN$ for 5 min; 1 mL/min; $t_r$ 8.873 min). HRMS (CI+) calcd. for $C_{19}H_{17}NO_3$: 307.1208; found: 307.1212 [M+].

Preparation 54

8-(tert-Butyl-dimethyl-silanyloxy)-4-[4-(tert-butyl-dimethyl-silanyloxy)-phenyl]-1,3a,4,9b-tetrahydro-3H-cyclopenta[c]chromen-2-one

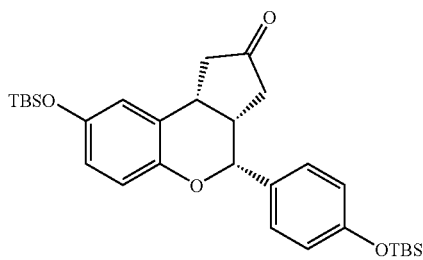

Dissolve Preparation 50 (1.59 g, 3.33 mmol) in 50 mL of THF. Add a slurry of 10% Pd/C (570 mg) in isopropyl alcohol. Stir the solution under 60 psi of hydrogen gas overnight. Filter the solution through celite and wash with isopropyl alcohol and THF. Combine and concentrate the organic solutions to afford a tan solid. Dissolve the solid 17 mL of DMF. Add imidazole (1.36 g, 20 mmol) and DMAP (42 mg, 0.34 mmol) followed by TBSCl (1.10 g, 7.3 mmol). Let the solution stir overnight. Dilute with EtOAc and wash with saturated aqueous sodium bicarbonate, water, brine, dry over $Na_2SO_4$, filter, and concentrate. Purify by silica gel chromatography eluting with 0-10% EtOAc in hexanes to afford 1.15 g (2.19, 66%) of preparation 54. $^1H$ NMR (400 MHz, MeOD): δ 7.33-7.30 (m, 2H), 6.90-6.87 (m, 2H), 6.85 (d, J=8.8 Hz, 1H), 6.68 (dd, J=2.2, 8.8 Hz, 1H), 6.63 (d, J=2.2 Hz, 1H), 5.15 (d, J=1.8 Hz, 1H), 3.87 (t, J=7.5 Hz, 1H), 2.93 (m, 1H), 2.81 (dd, J=7.6, 17.6 Hz, 1H), 2.62 (d, J=18.5 Hz, 1H), 2.36 (dd, J=12.3, 18.8 Hz, 1H), 2.04 (dd, J=7.9, 18.8 Hz, 1H), 1.02 (s, 9H), 1.01 (s, 9H), 0.24 (s, 6H), 0.21 (s, 6H).

Example 26

(3aR,4S,9bS)- and (3aS,4R,9bR)-4-(4-Hydroxy-phenyl)-2-methylene-1,2,3,3a,4,9b-hexahydro-cyclopenta [c]chromen-8-ol

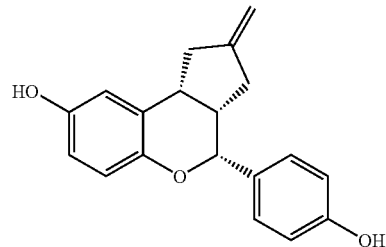

Add KHMDS (5.7 mL of 0.5 M solution in toluene, 2.85 mmol) to a solution of methyltriphenylphosphonium bromide (1.2 g, 3.36 mmol) in 30 mL of THF at −78° C. Stir for 30 min and then add via cannula a solution of preparation 54 (500 mg, 0.95 mmol) in 10 mL of THF followed by 2×5 mL THF washes. Remove cooling bath and let stir overnight. Quench with saturated aqueous ammonium chloride. Dilute with EtOAc wash with 1:1 brine:water, brine, dry over $Na_2SO_4$, filter and concentrate. Adsorb to silica gel and purify by silica gel chromatography eluting with 0-100% EtOAc in hexanes to afford the title compound in addition to mono and di-TBS protected material. Repeat the procedure starting with 250 mg of preparation 54 except stir for only 3 hrs. Combine the di-TBS protected material (219 mg, 0.42 mmol) and dissolve in 5 mL of THF. Add TBAF (0.88 mL of a 1 M solution in THF, 0.88 mmol). Let stir for 15 min and quench with saturated aqueous sodium carbonate. Dilute with water and EtOAc. Separate and extract the aqueous solution with EtOAc. Combine the organic solutions, add a little methanol, and wash with brine, dry over $Na_2SO_4$, filter and concentrate. Repeat the same procedure with the combined mono-TBS protected material. Combine all the deprotected material and adsorb to 5 g of silica gel. Purify by silica gel flash chromatography eluting with 10-40% (9:1 EtOAc:MeOH) in hexanes to afford 255 mg (0.87 mmol, 75%) of example 28. The two enantiomers can be separated by chiral preparative HPLC (Chiralpak AD, MeOH). $^1H$ NMR (400 MHz, MeOD): δ 7.32-7.29 (m, 2H), 6.84-6.80 (m, 2H), 6.72 (d, J=8.8 Hz, 1H), 6.64 (d, J=3.1 Hz, 1H), 6.58 (d, J=3.1, 8.8 Hz, 1H), 5.05 (d, J=1.8 Hz, 1H), 4.74 (d, J=13.2 Hz, 2H), 3.54 (t, J=7.5 Hz, 1H), 2.95-2.88 (m, 1H), 2.77-2.69 (m, 1H), 2.61 (d, J=16.3 Hz, 1H), 2.40-2.32 (m, 1H), 2.05 (dd, J=8.8, 16.7 Hz, 1H); HPLC (Zorbax C18 column; 10 to 100% $CH_3CN/H_2O$ for 10 min then 100% $CH_3CN$ for 5 min; 1 mL/min; $t_r$ 9.838 min; HRMS (ES−) calcd. for $C_{19}H_{17}O_3$: 293.1178; found:

Preparation 55

8-(tert-Butyl-dimethyl-silanyloxy)-4-[4-(tert-butyl-dimethyl-silanyloxy)-phenyl]-2-difluoromethylene-1,2,3,3a,4,9b-hexahydro-cyclopenta[c]chromene

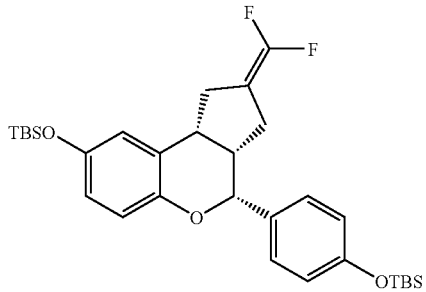

Dissolve diisopropylamine (67 µL, 0.48 mmol) in 2 mL of THF, cool to −50° C. and add n-butyllithium (238 µL of a 1.6 M solution in hexanes, 0.38 mmol). Then add a solution of (Difluoromethyl)diphenylphosphine oxide (prepared according to Edwards, M. L.; Stemerick, D. M.; Jarvi, E. T.; Matthews, D. P.; McCarthy, J. R. *Tetrahedron Lett.* 1990, 31, 5571-5574) in 0.5 mL of THF via cannula followed by a 0.5 mL wash. Let stir for 30 min and then add preparation 54 (100 mg, 0.19 mmol) as a solution in 0.5 mL of THF via syringe followed by a 0.5 mL wash. Let stir and allow to warm slowly to 0° C. over 2 hrs. Remove the cooling bath and let warm to room temperature and then warm to reflux for 1 hr. Cool the solution to room temperature and quench with saturated aqueous ammonium chloride. Dilute the solution with EtOAc, wash with brine, dry over $Na_2SO_4$, filter and concentrate. Adsorb to 1 g of silica gel and purify by silica gel chromatography eluting with 5-20% EtOAc to afford 41 mg (0.073 mmol, 39%) preparation 55. $^1$H NMR (400 MHz, MeOD): δ 7.35-7.30 (m, 2H), 6.91-6.88 (m, 2H), 6.83 (d, J=8.3 Hz, 1H), 6.69-6.65 (m, 2H), 5.14 (s, 1H), 3.60 (m, 1H), 2.82 (m, 1H), 2.74-2.64 (m, 2H), 2.42 (m, 1H), 2.09 (dd, J=8.3, 15.8 Hz, 1H), 1.03 (s, 9H), 1.02 (s, 9H), 0.24 (s, 6H), 0.22 (s, 6H).

Example 27

(3aR,4S,9bS)- and (3aS,4R,9bR)-2-Difluoromethyl-ene-4-(4-hydroxy-phenyl)-1,2,3,3a,4,9b-hexahydro-cyclopenta[c]chromen-8-ol

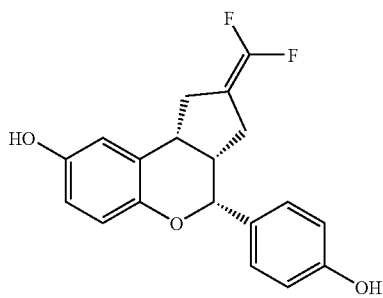

Add TBAF (135 µL of a 1M solution in THF, 0.135 mmol) to a solution of preparation 55 (38 mg, 0.068 mmol) in 1 mL of THF. Let stir for 5 min, add one more drop of TBAF and then quench with aqueous sodium bicarbonate. Dilute with EtOAc, wash with water, brine, dry over $Na_2SO_4$, filter and concentrate. Adsorb to 0.5 g of silica gel and purify by silica gel chromatography eluting with 5-50% (9:1 EtOAc:MeOH) in hexanes to afford 20 mg (0.061 mmol, 89%) of example 29. $^1$H NMR (400 MHz, MeOD): δ 7.31 (m, 2H), 6.83 (m, 2H), 6.74 (d, J=8.8 Hz, 1H), 6.67 (d, J=2.6 Hz, 1H), 6.61 (dd, J=2.6, 8.8 Hz, 1H), 5.07 (s, 1H), 3.60 (m, 1H), 2.86-2.73 (m, 2H), 2.64 (d, J=15.4 Hz, 1H), 2.34 (m, 1H), 2.04 (m, 1H); HPLC (Zorbax C18 column; 10 to 100% $CH_3CN/H_2O$ for 10 min then 100% $CH_3CN$ for 5 min; 1 mL/min; $t_r$ 10.094 min; HRMS (ES−) calcd. for $C_{19}H_{15}F_2O_3$: 329.0989; found: 329.0999 [M−1].

Preparation 56

8-(tert-Butyl-dimethyl-silanyloxy)-4-[4-(tert-butyl-dimethyl-silanyloxy)-phenyl]-2-trimethylsilanylethynyl-1,2,3,3a,4,9b-hexahydro-cyclopenta[c]chromene

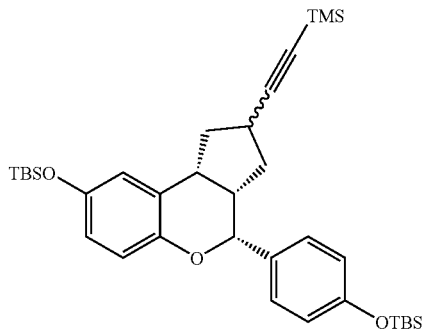

Add 1 mL of dry THF to dry cerium trichloride (120 mg, 0.22 mmol, prepared from cerium trichloride heptahydrate according to cerium (III) chloride in the Encyclopedia of Reagents for Organic Synthesis, Wiley Interscience), stir for 1 hr, and then cool to 0° C. In a separate flask add n-butyl-lithium (0.286 mL of a 1.6 M solution in hexanes, 0.46 mmol) to a solution of trimethylsilylacetylene (80 CL, 0.57 mmol) in 1 mL of THF cooled to −78° C. Add this solution to the cerium trichloride via cannula. Then add via cannula a solution of preparation 54 (120 mg, 0.22 mmol) in 1 mL of THF followed by 2×0.5 mL THF washes. Let stir for 3 hrs. Prepare another solution of lithiated trimethylsilylacetylene as described above and add it to the reaction flask via cannula. Let stir for 1 hr. Quench the reaction with saturated aqueous ammonium chloride, dilute with EtOAc, separate and extract the aqueous solution with EtOAc. Combine the organic solutions and wash with water, brine, dry over $Na_2SO_4$, filter and concentrate.

Dissolve the material in 2 mL of $CH_2Cl_2$. Add DMAP (3 mg, 0.024 mmol), triethylamine (0.096 mL, 0.69 mmol), and then add methylchlorooxoacetate (0.032 mL, 0.34 mmol). Let stir for 1 hr. Quench with saturated sodium bicarbonate and separate. Wash the organic solution with 1 M aqueous $NaH_2PO_4$, saturated aqueous sodium bicarbonate, brine, dry over $Na_2SO_4$, filter and concentrate. Adsorb to 1 g of silica gel and purify by silica gel flash chromatography eluting with 0-15% EtOAc in hexanes.

Dissolve the material in 1.5 mL of toluene. Add triphenyl-tin hydride (163 mg, 0.464 mmol) and AIBN (4 mg, 0.024 mmol). Warm the solution to 80° C. Let stir for 1 hr. Remove heat and let sit for 3 hrs. Filter through a glass frit and wash precipitate with ether. Combine the filtrates and concentrate. Adsorb to 1.2 g of silica gel and purify by silica gel chromatography eluting with 0-50% CH$_2$Cl$_2$ in hexanes to afford 56 mg (0.092 mmol) of preparation 56 as a 5:1 diastereomeric mixture of products. $^1$H NMR (400 MHz, CDCl$_3$) of major diastereomer: δ 7.37-7.27 (m, 2H), 6.89-6.85 (m, 2H), 6.81 (d, J=8.4 Hz, 1H), 6.65-6.60 (m, 2H), 4.98 (d, J=2.2 Hz, 1H), 3.49 (m, 1H), 2.75-2.50 (m, 3H), 1.81-1.66 (m, 3H), 1.03 (s, 9H), 1.02 (s, 9H), 0.24 (s, 6H), 0.22 (s, 6H), 0.10 (s, 9H).

Example 28

(3aR,4S,9bS)- and (3aS,4R,9bR)-2-Ethynyl-4-(4-hydroxy-phenyl)-1,2,3,3a,4,9b-hexahydro-cyclopenta [c]chromen-8-ol

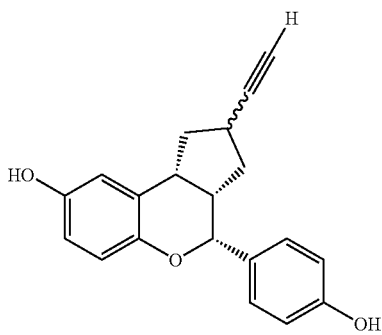

Add TBAF (0.28 mL of a 1 M solution in THF, 0.28 mmol) to a solution of preparation 56 (56 mg, 0.092 mmol) in 2 mL of THF. Let stir for 10 min. Quench with saturate sodium bicarbonate and dilute with EtOAc. Separate and wash the organic solution with water, brine, dry over Na$_2$SO$_4$, filter and concentrate. Adsorb to 0.5 g silica gel. Purify by silica gel chromatography eluting with 0-50% (9:1 EtOAc:MeOH) in hexanes to afford 11.3 mg (0.037 mmol) of example 30 as a 5:1 mixture of diastereomers. $^1$H NMR (400 MHz, MeOD) of major diastereomer: δ 7.27 (m, 2H), 6.83-6.81 (m, 2H), 6.74 (d, J=8.0 Hz, 1H), 6.64-6.56 (m, 2H), 4.89 (d, J=3.1 Hz, 1H), 3.48 (dt, J=8.8, 5.7 Hz, 1H), 2.74-2.57 (m, 3H), 2.22 (d, J=2.6 Hz), 1.64-1.57 (m, 3H); HPLC (Zorbax C18 column; 10 to 100% CH$_3$CN/H$_2$O for 10 min then 100% CH$_3$CN for 5 min; 1 mL/min; t$_r$ 9.683 min (major), 9.805 (minor); HRMS (ES−) calcd. for C$_{20}$H$_{17}$O$_3$: 305.1178; found: 305.1170 [M−1].

Preparation 57

8-Benzyloxy-4-(4-benzyloxy-phenyl)-2-ethylidene-1,2,3,3a,4,9b-hexahydro-cyclopenta [c]chromene

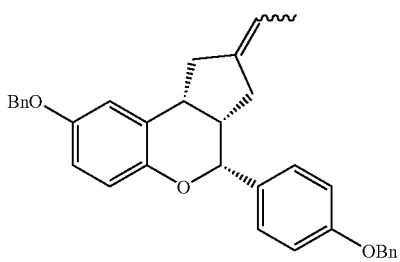

Heat a solution of preparation 50, (0.1562 g, 0.3278 mmol) in dry THF (6 mL) to dissolve. Cool a solution of ethyltriphenylphosphonium bromide (0.49 g, 1.3 mmol) in dry THF (10 mL) to −78° C. and then add KHMDS (2.2 mL of a 0.5 M solution in toluene, 1.1 mmol). After stirring at −78° C. for 15 min, add the solution of preparation 50 dropwise via cannula. Allow the solution to warm to RT for 2 h, then quench with saturated aqueous ammonium chloride (25 mL) and water (25 mL) and extract with EtOAc (3×50 mL). Wash the combined organic solutions with brine (50 mL), dry over Na$_2$SO$_4$, filter and concentrate. Purify by silica gel flash chromatography eluting with 0-50% CH$_2$Cl$_2$ in hexanes to afford 0.1552 g (0.3179 mmol, 97%) of preparation 57 as mixture of E and Z isomers. $^1$H NMR (400 MHz, CDCl$_3$): δ 7.36-7.50 (m, 12H, 2 isomers), 7.02-7.06 (m, 2H, 2 isomers), 6.78-6.89 (m, 4H, 2 isomers), 5.22 (m, 1H, 2 isomers), 5.17 (d, 1H, J=1.8 Hz, 1 isomer), 5.15 (d, 1H, J=1.3 Hz, 1 isomer), 5.13 (s, 2H, 1 isomer), 5.12 (s, 2H, 1 isomer), 5.06 (s, 2H, 1 isomer), 5.05 (s, 2H, 1 isomer), 3.63 (t, 1H, J=7.9 Hz, 1 isomer), 3.54 (t, 1H, J=7.0 Hz, 1 isomer), 2.60-2.85 (m, 3H, 2 isomers), 2.41-2.48 (m, 1H, 1 isomer), 2.25-2.32 (m, 1H, 1 isomer), 2.03-2.12 (m, 1H, 2 isomers), 1.52 (d, 3H, J=6.6 Hz, 1 isomer), 1.47 (d, 3H, J=7.0 Hz, 1 isomer). HRMS (CI+) calcd. for C$_{34}$H$_{33}$O$_3$: 489.6241; found: 489.2411 (M+1).

Preparation 58

8-Benzyloxy-4-(4-benzyloxy-phenyl)-2-propylidene-1,2,3,3a,4,9b-hexahydro-cyclopenta [c]chromene

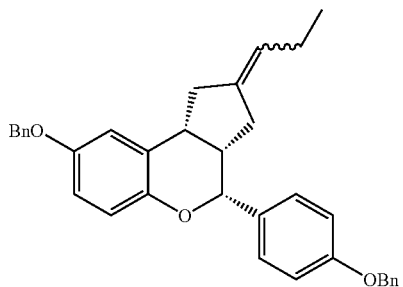

Preparation 58 can be prepared in a manner substantially similar to preparation 57 starting with preparation 50 (0.2041 g, 0.4283 mmol) and propyltriphenyl-phosphonium bromide to obtain 0.1927 g (0.3834 mmol, 90%) of a mixture of E and Z isomers. $^1$H NMR (400 MHz, CDCl$_3$): δ 7.36-7.50 (m, 12H, 2 isomers), 7.02-7.06 (m, 2H, 2 isomers), 6.79-6.89 (m, 4H, 2 isomers), 5.16 (m, 1H, 1 isomer), 5.145 (m, 1H, 1 isomer), 5.13 (s, 2H, 1 isomer), 5.12 (s, 2H, 1 isomer), 5.06 (s, 2H, 1 isomer), 5.05 (s, 2H, 1 isomer), 3.62 (t, 1H, J=7.5 Hz), 3.54 (t, 1H, J=7.0 Hz, 1 isomer), 2.58-2.92 (m, 3H, 2 isomers), 2.41-2.48 (m, 1H, 1 isomer), 2.25-2.32 (m, 1H, 1 isomer), 1.85-2.11 (m, 3H, 2 isomer), 0.896 (t, 3H, J=7.5 Hz, 1-isomer), 0.863 (t, 3H, J=7.5 Hz, 1 isomer). HRMS (CI+) calcd. for C$_{35}$H$_{35}$O$_3$: 503.2586; found: 503.2563 (M+1).

Preparation 59

8-Benzyloxy-4-(4-benzyloxy-phenyl)-2-butylidene-1,2,3,3a,4,9b-hexahydro-cyclopenta[c]chromene

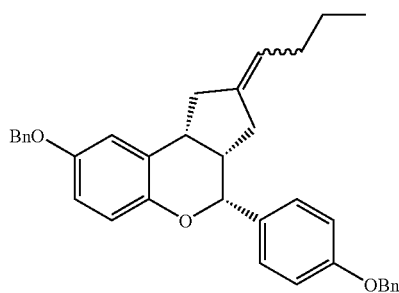

Preparation 59 can be prepared in a manner substantially similar to preparation 57 starting with preparation 50 (0.203 g, 0.427 mmol) and butyltriphenyl-phosphonium to obtain (0.1894 g, 0.3665 mmol, 86%) of a mixture of E and Z isomers. $^1$H NMR (400 MHz, CDCl$_3$): δ 7.34-7.50 (m, 12H, 2 isomers), 7.02-7.06 (m, 2H, 2 isomers), 6.78-6.88 (m, 4H, 2 isomers), 5.14-5.17 (m, 2H, 2 isomers), 5.13 (s, 2H, 1 isomer), 5.12 (s, 2H, 1 isomer), 5.06 (s, 2H, 1 isomer), 5.05 (s, 2H, 1 isomer), 3.61 (t, 1H, J=7.5 Hz, 1 isomer), 3.54 (t, 1H, J=6.6 Hz), 2.59-2.86 (m, 3H, 2 isomers), 2.42-2.49 (m, 1H, 1 isomer), 2.24-2.31 (m, 1H, 1 isomer), 2.03-2.11 (m, 1H, 2 isomers), 1.80-1.89 (m, 2H, 2 isomers), 1.22-1.35 (m, 2H, 2 isomers), 0.856 (t, 3H, J=7.5 Hz, 1 isomer), 0.804 (t, 3H, J=7.0 Hz, 1 isomer).

Preparation 60

2-Benzylidene-8-benzyloxy-4-(4-benzyloxy-phenyl)-1,2,3,3a,4,9b-hexahydro-cyclopenta[c]chromene

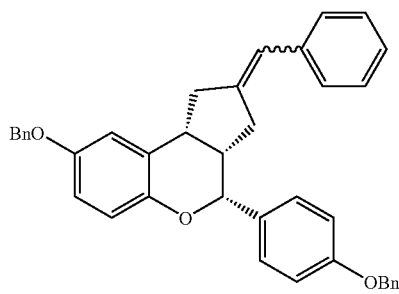

Preparation 60 can be prepared in a manner substantially similar to preparation 57 except the reaction mixture was heated to reflux overnight. Starting with preparation 50 (0.203 g, 0.427 mmol) using two addition of the Wittig reagent formed from benzyltriphenyl-phosphonium chloride affords 0.0922 g (0.167 mmol, 39%) of a mixture of E and Z isomers. $^1$H NMR (400 MHz, CDCl$_3$): δ, 7.20-7.51 (m, 17H, 2 isomers), 7.06 (d, 2H, J=8.6 Hz, 2 isomers), 6.82-6.90 (m, 4H, 2 isomers), 6.26 (s, 1H, major isomer), 5.20 (s, 1H, minor isomer), 5.18 (s, 2H, minor isomer), 5.14 (s, 2H, major isomer), 5.06 (s, 2H, minor isomer), 5.03 (s, 2H, major isomer), 3.70-3.78 (m, 1H, major isomer), 3.56-3.64 (m, 1H, minor isomer), 3.12-3.25 (m, 1H, 2 isomers), 2.24-3.00 (m, 3H, 2 isomers).

Example 29

2-Butyl-4-(4-hydroxy-phenyl)-1,2,3,3a,4,9b-hexahydro-cyclopenta[c]chromen-8-ol

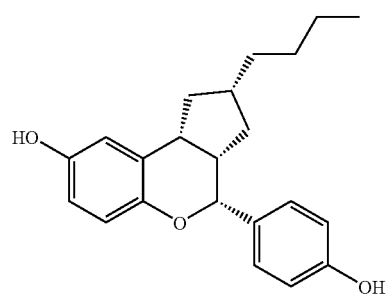

Dissolve preparation 59 (0.1829 g, 0.3540 mmol) in 11 mL of THF. Add a slurry of 10% Pd/C (0.0619 g) in 11 mL of isopropyl alcohol. Stir the solution under an atmosphere of hydrogen at ambient pressure and temperature overnight. Filter the solution through Celite and wash the filter cake with isopropyl alcohol and THF. Combine and concentrate the filtrate and washings and concentrate. Adsorb to 2 g of silica gel. Purify by silica gel flash chromatography eluting with 10-50% (1:9 MeOH/EtOAc) in hexanes to afford 0.0823 g (0.2432 mmol, 69%) of example 31. $^1$H NMR (400 MHz, MeOD): δ 7.27 (d, 2H, J=8.8 Hz), 6.81 (d, 2H, J=8.4 Hz), 6.71 (d, 1H, J=8.4 Hz), 6.58 (d, 1H, J=3.1 Hz), 6.54 (dd, 1H, J=3.1 Hz, J=8.8 Hz), 3.41-3.47 (m, 1H), 2.48-2.63 (m, 2H), 1.77-1.90 (m, 1H), 1.40-1.46 (m, 1H), 1.14-1.26 (m, 8H), 0.863 (t, 3H, J=6.6 Hz). HPLC (Zorbax C18 column; 10 to 100% CH$_3$CN/H$_2$O for 10 min then 100% CH$_3$CN for 5 min; 1 mL/min; t$_r$ 11.575 min). LRMS (ES−): 337.2 (M−1).

The two enantiomers can be separated by chiral preparative HPLC (Chiralpak AD, 15% EtOH/Heptane).

Enantiomer A: $^1$H NMR (400 MHz, MeOD): δ 7.27 (d, 2H, J=8.8 Hz), 6.81 (d, 2H, J=8.4 Hz), 6.71 (d, 1H, J=8.4 Hz), 6.58 (d, 1H, J=3.1 Hz), 6.54 (dd, 1H, J=3.1 Hz, J=8.8 Hz), 3.41-3.47 (m, 1H), 2.48-2.63 (m, 2H), 1.77-1.90 (m, 1H), 1.40-1.46 (m, 1H), 1.14-1.26 (m, 8H), 0.863 (t, 3H, J=6.6 Hz). HPLC (Zorbax C18 column; 10 to 100% CH$_3$CN/H$_2$O for 10 min then 100% CH$_3$CN for 5 min; 1 mL/min; t$_r$ 11.568 min). HPLC (Chiralpak AD, 15% EtOH/Heptane; 1 mL/min; t$_R$=3.213 min).

LRMS (ES−): 337.2 (M−1).

Enantiomer B: $^1$H NMR (400 MHz, MeOD): δ 7.27 (d, 2H, J=8.8 Hz), 6.81 (d, 2H, J=8.4 Hz), 6.71 (d, 1H, J=8.4 Hz), 6.58 (d, 1H, J=3.1 Hz), 6.54 (dd, 1H, J=3.1 Hz, J=8.8 Hz), 3.41-3.47 (m, 1H), 2.48-2.63 (m, 2H), 1.77-1.90 (m, 1H), 1.40-1.46 (m, 1H), 1.14-1.26 (m, 8H), 0.863 (t, 3H, J=6.6 Hz). HPLC (Zorbax C18 column; 10 to 100% CH$_3$CN/H$_2$O for 10 min then 100% CH$_3$CN for 5 min; 1 mL/min; t$_r$ 11.578 min). HPLC (Chiralpak AD, 15% EtOH/Heptane; 1 mL/min; t$_R$=5.877 min).

LRMS (ES−): 337.2 (M−1).

Example 30

4-(4-Hydroxy-phenyl)-2-propyl-1,2,3,3a,4,9b-hexahydro-cyclopenta[c]chromen-8-ol

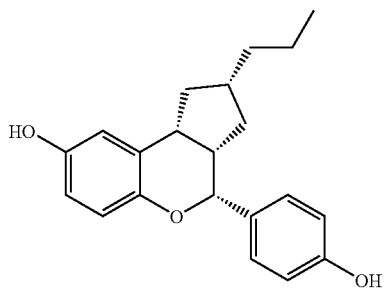

Example 32 can be prepared in a manner substantially similar to that described for example 31 starting from preparation 58 (0.1842 g, 0.3665 mmol) to afford 0.108 g (0.331 mmol, 90%). $^1$H NMR (400 MHz, MeOD): δ 7.27 (d, 2H, J=8.8 Hz), 6.81 (d, 2H, J=8.8 Hz), 6.71 (d, 1H, J=8.8 Hz), 6.58 (d, 1H, J=3.1 Hz), 6.54 (dd, 1H, J=3.1 Hz, J=8.8 Hz), 3.41-3.47 (m, 1H), 2.48-2.63 (m, 2H), 1.80-1.92 (m, 1H), 1.38-1.46 (m, 1H), 1.14-1.30 (m, 6H), 0.849 (t, 3H, J=7.0 Hz). HPLC (Zorbax C18 column; 10 to 100% $CH_3CN/H_2O$ for 10 min then 100% $CH_3CN$ for 5 min; 1 mL/min; $t_r$ 11.137 min). LRMS (ES−): 323.2 (M−1).

The two enantiomers can be separated by chiral preparative HPLC (Chiralpak AD, IPA/Heptane).

Enantiomer A: $^1$H NMR (400 MHz, MeOD): δ 7.27 (d, 2H, J=8.8 Hz), 6.81 (d, 2H, J=8.8 Hz), 6.71 (d, 1H, J=8.8 Hz), 6.58 (d, 1H, J=3.1 Hz), 6.54 (dd, 1H, J=3.1 Hz, J=8.8 Hz), 3.41-3.47 (m, 1H), 2.48-2.63 (m, 2H), 1.80-1.92 (m, 1H), 1.38-1.46 (m, 1H), 1.14-1.30 (m, 6H), 0.849 (t, 3H, J=7.0 Hz). HPLC (Zorbax C18 column; 10 to 100% $CH_3CN/H_2O$ for 10 min then 100% $CH_3CN$ for 5 min; 1 mL/min; $t_r$ 11.125 min). HPLC (Chiralpak AD, 15% EtOH/Heptane; 1 mL/min; $t_R$=3.477 min).

LRMS (ES−): 323.2 (M−1).

Enantiomer B: $^1$H NMR (400 MHz, MeOD): δ 7.27 (d, 2H, J=8.8 Hz), 6.81 (d, 2H, J=8.8 Hz), 6.71 (d, 1H, J=8.8 Hz), 6.58 (d, 1H, J=3.1 Hz), 6.54 (dd, 1H, J=3.1 Hz, J=8.8 Hz), 3.41-3.47 (m, 1H), 2.48-2.63 (m, 2H), 1.80-1.92 (m, 1H), 1.38-1.46 (m, 1H), 1.14-1.30 (m, 6H), 0.849 (t, 3H, J=7.0 Hz). HPLC (Zorbax C18 column; 10 to 100% $CH_3CN/H_2O$ for 10 min then 100% $CH_3CN$ for 5 min; 1 mL/min; $t_r$ 11.127 min). HPLC (Chiralpak AD, 15% EtOH/Heptane; 1 mL/min; $t_R$=6.997 min).

LRMS (ES−): 323.2 (M−1).

Example 31

2-Ethyl-4-(4-hydroxy-phenyl)-1,2,3,3a,4,9b-hexahydro-cyclopenta[c]chromen-8-ol

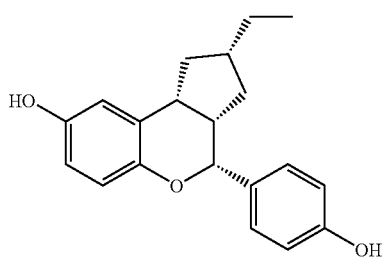

Example 33 can be prepared in a manner substantially similar to that described for example 31 starting from preparation 57. $^1$H NMR (400 MHz, MeOD): δ 7.27 (d, 2H, J=8.8 Hz), 6.81 (d, 2H, J=8.4 Hz), 6.71 (d, 1H, J=8.8 Hz), 6.59 (d, 1H, J=3.1 Hz), 6.54 (dd, 1H, J=3.1 Hz, J=8.8 Hz), 3.42-3.48 (m, 1H), 2.49-2.63 (m, 2H), 1.71-1.83 (m, 1H), 1.40-1.47 (m, 1H), 1.15-1.26 (m, 4H), 0.829 (t, 3H, J=7.5 Hz). HPLC (Zorbax C18 column; 10 to 100% $CH_3CN/H_2O$ for 10 min then 100% $CH_3CN$ for 5 min; 1 mL/min; $t_r$ 10.681 min) LRMS (ES−): 309.2 (M−1).

The two enantiomers can be separated by chiral preparative HPLC (Chiralpak AD, 15% EtOH/Heptane).

Enantiomer A: $^1$H NMR (400 MHz, MeOD): □ 7.27 (d, 2H, J=8.8 Hz), 6.81 (d, 2H, J=8.4 Hz), 6.71 (d, 1H, J=8.8 Hz), 6.59 (d, 1H, J=3.1 Hz), 6.54 (dd, 1H, J=3.1 Hz, J=8.8 Hz), 3.42-3.48 (m, 1H), 2.49-2.63 (m, 2H), 1.71-1.83 (m, 1H), 1.40-1.47 (m, 1H), 1.15-1.26 (m, 4H), 0.829 (t, 3H, J=7.5 Hz). HPLC (Zorbax C18 column; 10 to 100% $CH_3CN/H_2O$ for 10 min then 100% $CH_3CN$ for 5 min; 1 mL/min; $t_r$ 10.703 min). HPLC (Chiralpak AD, 15% EtOH/Heptane; 1 mL/min; $t_R$=3.687 min).

LRMS (ES−) 309.2.

Enantiomer B: $^1$H NMR (400 MHz, MeOD): □ 7.27 (d, 2H, J=8.8 Hz), 6.81 (d, 2H, J=8.4 Hz), 6.71 (d, 1H, J=8.8 Hz), 6.59 (d, 1H, J=3.1 Hz), 6.54 (dd, 1H, J=3.1 Hz, J=8.8 Hz), 3.42-3.48 (m, 1H), 2.49-2.63 (m, 2H), 1.71-1.83 (m, 1H), 1.40-1.47 (m, 1H), 1.15-1.26 (m, 4H), 0.829 (t, 3H, J=7.5 Hz). HPLC (Zorbax C18 column; 10 to 100% $CH_3CN/H_2O$ for 10 min then 100% $CH_3CN$ for 5 min; 1 mL/min; $t_r$ 10.663 min). HPLC (Chiralpak AD, 15% EtOH/Heptane; 1 mL/min; $t_R$=8.264 min).

LRMS (ES−) 309.2 (M−1).

Example 32

2-Benzyl-4-(4-hydroxy-phenyl)-1,2,3,3a,4,9b-hexahydro-cyclopenta[c]chromen-8-ol

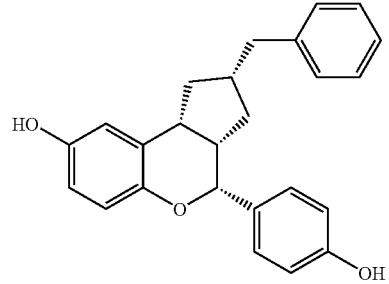

Example 34 can be prepared in a manner substantially similar to that described for example 31 starting from preparation 60 except under an atmosphere of hydrogen at 60 psi of $H_2$. $^1$H NMR (400 MHz, MeOD): □ 7.05 (m, 7H), 6.79 (d, 2H, J=8.8 Hz), 6.74 (d, 1H, J=8.4 Hz), 6.56-6.58 (m, 2H), 4.90-4.92 (m, 1H), 3.40-3.46 (m, 1H), 2.58-2.66 (m, 1H), 2.46-2.56 (m, 1H), 2.32-2.43 (m, 2H), 2.10-2.22 (m, 1H), 1.28-1.45 (m, 3H). HPLC (Zorbax C18 column; 10 to 100% $CH_3CN/H_2O$ for 10 min then 100% $CH_3CN$ for 5 min; 1 mL/min; $t_r$ 11.269 min). LRMS (ES−): 371.2 (M−1).

Test Procedures

ER Binding Assay

The competition ER binding assay was run in a buffer containing 50 mM N-[2-hydroxyethyl]piperazine-N'-[2- ethanesulfonic acid (Hepes) pH 7.5, 1.5 mM EDTA, 150 mM NaCl, 10% glycerol, 1 mg/mL ovalbumin, 5 mM DTT, 0.025 µCi per well of $^3$H-Estradiol (NEN #NET517 at 118 Ci/mmol, 1 mCi/mL), and 10 ng/well ERAlpha or ERbeta Receptor (PanVera). Competing compounds were added at 10 different concentrations. Non-specific binding was determined in the presence of 1 µM of E2 (17-β Estradiol, Sigma, St. Louis, Mo.). The binding reaction (140 µL) was incubated for 4 hours at room temperature, then 70 µL of cold dextran coated charcoal (DCC) buffer was added to each reaction (DCC buffer was prepared by adding 0.75 g of charcoal [Sigma] and 0.25 g of dextran [Pharmacia] per 50 mL of assay buffer). The incubation plates were mixed for 8 minutes on an orbital shaker at 4° C. and then centrifuged at 3,000 rpm for 10 minutes at 4° C. An aliquot of 120 µl of the mix was transferred to another 96-well, white flat bottom plate (Costar) and 175 µl of Wallac Optiphase Hisafe 3 scintillation fluid was added to each well. The plates were sealed and then shaken vigorously on an orbital shaker. After an incubation of 2.5 hrs, the radioactivity was counted in a Wallac Microbeta counter. The $IC_{50}$ and percent inhibition at 10 µM were calculated. The $K_d$ for $^3$H-Estradiol was determined by saturation binding to ERα and ERβ receptors. The $IC_{50}$ values for compounds were converted to $K_i$ values using the Cheng-Prusoff equation and the $K_d$ values were determined by saturation binding assay. Compounds of Examples 1-19 and 22-25 are active in the assay as described. Preferred compounds bind to the ER beta receptor with a $K_i$ of less than 20 nM. More preferred compounds bind to the ER beta receptor with a $K_i$ of less than 1 nM. Compounds that are selective to binding to the ER beta receptor compared to the ER alpha receptor bind to the ER beta receptor with a lower $K_i$ compared to the $K_i$ for the ER alpha receptor.

As determined by the above assay, the compounds of examples 1-32 exhibit binding affinities (Kis) at the ER Alpha subtype in the range 5.0→10,000 nM and to the ER beta subtype in the range of 0.20-429 nM.

LNCaP Human PCa Xenograft Assay

ERbeta agonists are evaluated for their effects on the growth of androgen-sensitive LNCaP human prostatic cancer (PCa) xenografts grown in intact sexually mature (5-6 weeks old) Hsd: Athymic Nude-nu (Athymic Nude) male mice. $2.0 \times 10^6$ LNCaP tumor cells are injected bilaterally by the subcutaneous route into the pre-tracheal region of testicular intact male mice. Mice are castrated via the scrotal route to serve as the positive control group. Test compounds are administered once per day by subcutaneous or gavage administration at multiple dose levels in a volume of 0.2 ml to xenograft-bearing mice starting on the day following tumor injection. Test compounds are reformulated weekly based on average group mean body weights. The vehicle for these studies is 1% carboxymethyl cellulose (CMC) with 0.25% Tween 80. Body weights and tumor measurements are recorded on a weekly basis and entered directly into a JMP™ (SAS; Cary, N.C.) spreadsheet from electronic caliper measurement. Tumor volumes in mm$^3$ are calculated in JMP using the following formula: L×W×H×0.5236. Tumor and body weight responses for individual mice are recorded on a weekly basis. When LNCaP tumor volumes enter log-phase expansion, lesions are measured every 3-4 days. Growth rates are determined using linear modeling of the log tumor values and time to treatment failure (tumor vol=1300-1500 mm$^3$) are determined using a linear extrapolation model (SAS; Cary, N.C.). Because of humane animal use considerations, animals are sacrificed when their tumor volumes approach 1200-1400 mm$^3$. At necropsy, final tumor measurement and body weights are recorded and whole blood is obtained via cardiac puncture and allowed to clot on ice. Serum is transferred to appropriately labeled 0.5 ml Eppendorf micro tubes, and samples are stored at −80° C. for biomarker analysis.

General Rat Preparation Procedure

Seventy-five day old (unless otherwise indicated) female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room was 12 hours light and 12 hours dark.

Dosing Regimen Tissue Collection: After a one week acclimation period (therefore, two weeks post-OVX) daily dosing with a compound of formula (I) ("F-I") is initiated. 17α-ethynyl estradiol or F-I is given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: Xylazine (2:1, v:v) mixture and a blood sample is collected by cardiac puncture. The animals are then sacrificed by asphyxiation with $CO_2$, the uterus is removed through a midline incision, and a wet uterine weight is determined. 17α-ethynyl estradiol is obtained from Sigma Chemical Co., St. Louis, Mo.

Cardiovascular Disease/Hyperlipidemia

The blood samples from above are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay

The uteri from above are kept at 4° C. until time of enzymatic analysis. The uteri are then homogenized in 50 volumes of 50 mM Tris buffer (pH 8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosinophils in the uterus is an indication of estrogenic activity of a compound. The maximal velocity of a 15 second interval is determined over the initial, linear portion of the reaction curve.

Inhibition of Bone Loss (Osteoporosis) Test Procedure

Following the general preparation procedure described above, the rats are treated daily for thirty-five days (6 rats per treatment group) and sacrificed by carbon dioxide asphyxiation on the 36th day. The thirty-five day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized X-rays generated and analyzed by an image analysis program (NIH image) at the distal metaphysis. The proximal aspect of the tibiae from these animals are also scanned by quantitative computed tomography. In accordance with the above procedures, F-I or ethynyl estradiol ($EE_2$) in 20% hydroxypropyl β-cyclodextrin are orally administered to test animals.

Therapeutic Methods of Use and Dosages

Various diseases and conditions described to be treated herein, are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of formula (I).

As used herein, the term "patient" refers to a warm blooded animal such as a mammal that is afflicted with a particular estrogen receptor-beta mediated disease. It is understood that guinea pigs, dogs, cats, rats, mice, horses, cattle, sheep, and humans are examples of animals within the scope of the meaning of the term.

As used herein, the term "therapeutically effective amount" of a compound of formula (I) refers to an amount which is effective in controlling diseases and conditions associated with estrogen receptor-beta mediated diseases such as prostate cancer, benign prostatic hyperplasia, testicular cancer, cardiovascular diseases, neurodegenerative disorders, urinary incontinence, CNS disorders, GI tract disorders, and osteoporosis. The term "controlling" is intended to refer to all processes wherein there may be a slowing, interrupting, arresting, or stopping of the progression of the diseases and conditions described herein, but does not necessarily indicate a total elimination of all disease and condition symptoms, but does include prophylactic treatment of the diseases and conditions associated with estrogen receptor-beta mediated diseases such as prostate cancer, benign prostatic hyperplasia, testicular cancer, cardiovascular diseases, neurodegenerative disorders, urinary incontinence, CNS, GI tract disorders, and osteoporosis.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (I) is expected to vary from about 0.001 milligram per kilogram of body weight per day (mg/kg/day) to about 100 mg/kg/day. Preferred amounts can be determined by one skilled in the art.

In effecting treatment of a patient afflicted with the diseases and conditions described above, a compound of formula (I) can be administered in any form or mode which makes the compound bioavailable in a therapeutically effective amount, including oral, inhalation, and parenteral routes. For example, compounds of formula (I) can be administered orally, by inhalation of an aerosol or dry powder, subcutaneously, intramuscularly, intravenously, transdermally, intranasally, rectally, topically, and the like. Oral or inhalation administration is generally preferred for treatment of respiratory diseases, e.g. asthma. One skilled in the art of preparing formulations can readily select the proper form and mode of administration depending upon the particular characteristics of the compound selected, the disease or condition state to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility and the like.

In another embodiment, the present invention provides pharmaceutical compositions comprising a therapeutically effective amount of a compound of formula (I) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material, which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of formula (I) present in such compositions is such that a suitable dosage will be obtained. Preferred compositions and preparations are able to be determined by one skilled in the art.

The compounds of the present invention may also be administered by inhalation, such as by aerosol or dry powder. Delivery may be by a liquefied or compressed gas or by a suitable pump system that dispenses the compounds of the present invention or a formulation thereof. Formulations for administration by inhalation of compounds of formula (I) may be delivered in single phase, bi-phasic, or tri-phasic systems. A variety of systems are available for the administration by aerosols of the compounds of formula (I). Dry powder formulations are prepared by either pelletizing or milling the compound of formula (I) to a suitable particle size or by admixing the pelletized or milled compound of formula (I) with a suitable carrier material, such as lactose and the like. Delivery by inhalation includes the necessary container, activators, valves, subcontainers, and the like. Preferred aerosols and dry powder formulations for administration by inhalation are able to be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (I) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerin, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The invention claimed is:

1. A compound selected from:
   a. (6S,6aR,10aS)-2-Hydroxy-6-(4-hydroxy-phenyl)-6,6a,7,8,10,10a-hexahydro-benzo[c]chromen-9-one;
   b. (6aR,6S,10aS)-6-(4-Hydroxy-phenyl)-9-methylene-6a,7,8,9,10,10a-hexahydro-6H-benzo[c]chromen-2-ol;
   e. (6aR,6S,10aS)-9,9-Difluoro-6-(4-hydroxy-phenyl)-6a,7,8,9,10,10a-hexahydro-6H-benzo[c]chromen-2-ol;
   f. (6aR,6S,10aS)-2-Hydroxy-6-(4-hydroxy-phenyl)-6a,9,10,10a-tetrahydro-6H,7H-benzo[c]chromen-8-one;
or a pharmaceutically acceptable salt thereof.

2. A compound according to claim 1 wherein the compound is of the formula:

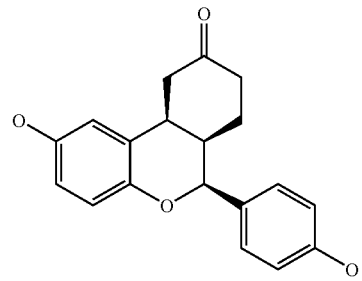

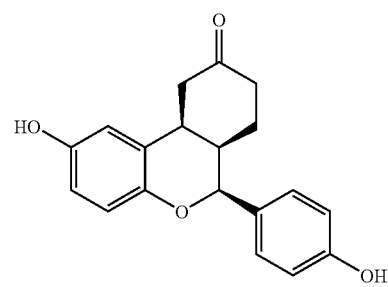

or a pharmaceutically acceptable salt thereof.

3. A compound according to claim 1 wherein the compound is of the formula:

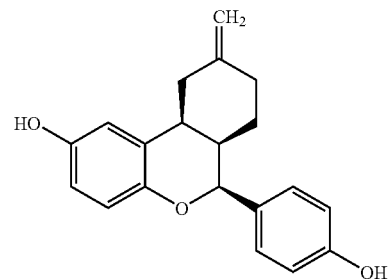

or a pharmaceutically acceptable salt thereof.

4. A compound according to claim 1 wherein the compound is of the formula:

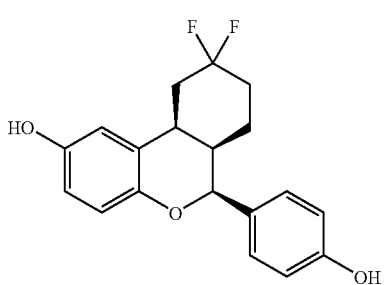

or a pharmaceutically acceptable salt thereof.

5. A compound according to claim 1 wherein the compound is of the formula:

or a pharmaceutically acceptable salt thereof.

6. A pharmaceutical composition comprising a compound of claim 1 or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 7,585,985 B2  Page 1 of 1
APPLICATION NO. : 12/184507
DATED : September 8, 2009
INVENTOR(S) : Norman et al.

It is certified that error appears in the above-identified patent and that said Letters Patent is hereby corrected as shown below:

Title page, under Item [60] "Related U.S. Application Data," after "10/552,504 filed," insert -- Oct. 6, 2005 --.

At Column 100, lines 5-16, in Claim 2, after the word "formula:" delete the first structure

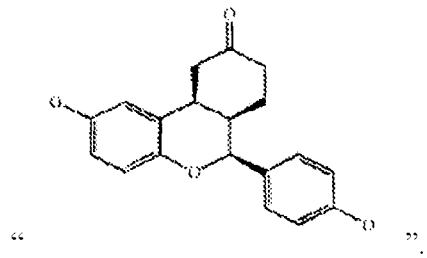

Signed and Sealed this

Twenty-fourth Day of August, 2010

David J. Kappos
*Director of the United States Patent and Trademark Office*